United States Patent
Slusher et al.

(10) Patent No.: US 11,110,104 B2
(45) Date of Patent: Sep. 7, 2021

(54) GLUTAMINE ANTAGONISTS FOR THE TREATMENT OF COGNITIVE DEFICITS AND PSYCHIATRIC DISORDERS

(71) Applicants: THE JOHNS HOPKINS UNIVERSITY, Baltimore, MD (US); ICAHN SCHOOL OF MEDICINE AT MOUNT SINAI, New York, NY (US)

(72) Inventors: Barbara Slusher, Kingsville, MD (US); David Volsky, Scarsdale, NY (US); Mike Nedelcovych, Richmond, VA (US); Kristen Hollinger, Parkton, MD (US); Atsushi Kamiya, Pikesville, MD (US)

(73) Assignees: The Johns Hopkins University, Baltimore, MD (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/884,974

(22) Filed: Jan. 31, 2018

(65) Prior Publication Data
US 2018/0193362 A1    Jul. 12, 2018

Related U.S. Application Data

(63) Continuation-in-part of application No. PCT/US2016/044825, filed on Jul. 29, 2016.

(60) Provisional application No. 62/199,317, filed on Jul. 31, 2015, provisional application No. 62/199,566, filed on Jul. 31, 2015.

(51) Int. Cl.
| *A61K 31/655* | (2006.01) |
| *A61K 31/42*  | (2006.01) |
| *A61K 31/223* | (2006.01) |
| *A61K 31/198* | (2006.01) |
| *A61P 25/28*  | (2006.01) |

(52) U.S. Cl.
CPC .......... *A61K 31/655* (2013.01); *A61K 31/198* (2013.01); *A61K 31/223* (2013.01); *A61K 31/42* (2013.01); *A61P 25/28* (2018.01)

(58) Field of Classification Search
CPC ............................. A61K 31/655; A61P 25/28
See application file for complete search history.

(56) References Cited

U.S. PATENT DOCUMENTS

| 3,773,919 | A  | 11/1973 | Boswell et al. |
| 4,485,045 | A  | 11/1984 | Regen |
| 4,544,545 | A  | 10/1985 | Ryan et al. |
| 4,767,628 | A  | 8/1988  | Hutchinson |
| 5,695,751 | A  | 12/1997 | Friedman et al. |
| 6,362,226 | B2 | 3/2002  | Phillips, III et al. |
| 2004/0192645 | A1 |  9/2004 | Hollingsworth et al. |
| 2007/0010507 | A1 |  1/2007 | Bombardelli |
| 2015/0119327 | A1 |  4/2015 | Muotri et al. |
| 2016/0008380 | A1 |  1/2016 | Raabe et al. |
| 2018/0221337 | A1* | 8/2018 | Slusher .............. A61K 31/7076 |
| 2018/0222930 | A1* | 8/2018 | Slusher ................ C07F 9/65616 |

FOREIGN PATENT DOCUMENTS

| EP | 0102324 A2 | 3/1984 |
| EP | 0133988 A2 | 3/1985 |
| WO | WO 2014/138391 | 9/2014 |
| WO | 2017023774 A1 | 2/2017 |
| WO | 2017023791 A1 | 2/2017 |
| WO | WO 2017/023774 * | 2/2017 |
| WO | WO 2017/023787 * | 2/2017 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995 (Year: 1985).*
McArthur (Ann. Neurol. (2010) 67:699-714,) (Year: 2010).*
Mak et. al. (Parkinsonian and Related Disorders (2015)). (Year: 2015).*
Thakurathi et. al. (Expert Opin. Investig. Drugs (2013) 22:259-265). (Year: 2013).*
Patti (Expert Opin. Investig. Drugs (2012) 21:1679-1699) . (Year: 2012).*
Thomson et al., "Systemic administration of lipopolysaccharide and interleukin-1beta have different effects on memory consolidation," Brain Res Bull, 2005, 67:24-9.
Varoqui et al., "Cloning and Functional Identification of a Neuronal Glutamine Transporter," J. Biol. Chem., 2000, 275 (6):4049-4054.
"Wook Koo et al., ""Essential Role of Mesolimbic Brain-Derived NeurotrophicFactor in Chronic Social Stress-Induced Depressive Behaviors,"" Biological Psychiatry, 2016, 80(6): p. 469-478.".
Wyatt et al., "Tenofovir alafenamide for HIV infection: is less more?," Lancet, 2015, 385(9987):2559-60.

(Continued)

Primary Examiner — Marcos L Sznaidman
(74) Attorney, Agent, or Firm — Casimir Jones, S.C.

(57) ABSTRACT

The disclosure provides compounds having formula (I):

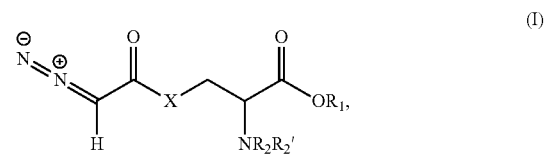

and the pharmaceutically acceptable salts thereof, wherein $R_1$, $R_2$, $R_2'$, and X are as defined as set forth in the specification, for use in treating cognitive deficits and/or psychiatric disorders, such as those associated with neurological or neurodegenerative disorders, psychiatric or mood disorders, and HIV-associated neurocognitive disorders (HAND). Compounds having formula (I) are prodrugs that release glutamine analogs, e.g., 6-diazo-5-oxo-L-norleucine (DON).

13 Claims, 22 Drawing Sheets

(56) References Cited

OTHER PUBLICATIONS

Zgòdka et al., "A diffusible analogue of N 3-(4-methoxyfumaroyl)-I-2,3-diaminopropanoic acid with antifungal activity," Microbiology, 2001, 147:1955-1959.
"Zink, ""Translational research models and novel adjunctive therapies forneuroAIDS,""" J Neuroimmune Pharmacol, 2007, 2(1): p. 14-9.".
Acevedo et al., "Synthesis and Analysis of the Sterically Constrained L-Glutamine Analogues (3S,4R)-3,4-Dimethyl-L-glutamine and (3S,4R)-3,4-Dimethyl-L-pyroglutamic Acid," Tetrahedron., 2001, 57:6353-6359.
Anacker et al., "Neuroanatomic Differences Associated With Stress Susceptibility and Resilience," Biological psychiatry, 2016, 79(10): p. 840-49.
Antinori et al., "Updated research nosology for HIV-associated neurocognitive disorders," Neurology, 2007, 69(18): p. 1789-1799.
Ausubel et al., "Current Protocols in Molecular Biology," John Wiley & Sons, N.Y., edition as of Dec. 2008.
Borjabad et al., "Significant effects of antiretroviral therapy on global gene expression in brain tissues of patients with HIV-1-associated neurocognitive disorders," PLoS Pathog., 2011, 7(9): p. e1002213.
Cao et al., "Astrocyte-derived ATP modulates depressive-like behaviors," Nature medicine, 2013, 19(6): p. 773-777.
Chapman, "PEGylated antibodies and antibody fragments for improved therapy: a review," Adv. Drug Deliv. Rev., 2002, 54(4):531-545.
Cunningham-Rundles et.al., "Biological activities of polyethyleneglycol immunoglobulin conjugates resistance to enzymatic degradation," J. Immunol. Meth., 1992, 152(2):177-190.
Darmaun et al., "Phenylbutyrateinduce glutamine depletion in humans: effect on leucine metabolism," Am. Physiol. Soc., 1998, 274(5):E801-E807.
Dickens et al., "CSF Metabolomics Implicate Bioenergetic Adaptation as a Neural Mechanism Regulating Shifts in the Cognitive States of HIV-Infected Subjects," AIDS, 2015, 29(5):559-569.
Ellis et al., "HIV and antiretroviral therapy in the brain: neuronal injury and repair," Nat. Rev. Neurosci., 2007, 8(1): p. 33-44.
Eppstein et al., "Biological activity of liposome-encapsulated murine interferon gamma is mediated by a cell membrane receptor," Proc. Natl. Acad. Sci. U.S.A., 1985, 82(11):3688-3692.
Everall et al., "Cliniconeuropathologic correlates of human immunodeficiency virus in the era of antiretroviral therapy," J. Neurovirol., 2009, 15(5-6): p. 360-370.
Freshney, R. I., "Culture of Animal Cells, A Manual of Basic Technique", 5th ed., John Wiley & Sons, Hoboken, N.J., 2005.
Gelman et al., "The National NeuroAIDS Tissue Consortium brain gene array: two types of HIV-associated neurocognitive impairment," PLoS One, 2012, 7(9): p. e46178.
Harezlak et al., "Persistence of HIV-associated cognitive impairment, inflammation, and neuronal injury in era of highly active antiretroviral treatment," AIDS, 2011, 25(5): p. 625-633.
Harlow et al., "Antibodies—A Laboratory Manual," Cold Spring Harbor Laboratory Press, Cold Spring Harbor, 1988.
Hart et al., "Neuroprotection trials in Parkinson's disease: systematic review," Mov. Disord., 2009, 24(5):647-54.
Heaton et al., "HIV-associated neurocognitive disorders before and during the era of combination antiretroviral therapy: differences in rates, nature, and predictors," J. Neurovirol., 2011, 17(1): p. 3-16.
Heaton et al., "HIV-associated neurocognitive disorders persist in the era of potent antiretroviral therapy: CHARTER Study," Neurology, 2010, 75(23): p. 2087-96.
Hodes et al., "Individual differences in the peripheral immune system promote resilience versus susceptibility to social stress," Proceedings of the National Academy of Sciences of the United States of America, 2014, 111(45): p. 16136-41.
Hollinger et al., "Dose-dependent inhibition of GCPII to prevent and treat cognitive impairment in the EAE model of multiple sclerosis," Brain Res., 2016, 1635:105-12.

Darmaun et al., "Phenylbutyrateinduce glutamine depletion in humans: effect on leucine metabolism," Am. Physiol. Soc., 1990, 274(5):E801-E807.
Heaton et al., "HIV-associated neurocognitive disorders persist in the era of potent antiretroviral therapy: CHARTER Study," Neurology, 2010, 75(23): p. 2087-06.
Hollinger et al., "Dose-dependent inhibitionrof GCPII to prevent and treat cognitive impairment in the EAE model of multiple sclerosis," Brain Res., 2016, 1635:105-12.
Hwang et al. "Hepatic uptake and degradation of unilamellar sphingomyelin/cholesterol liposomes: a kinetic study," Proc. Natl. Acad. Sci. U.S.A., 1980, 77(7):4030-4034.
International Search Report and Written Opinion for Application No. PCT/US2016/044825 dated Nov. 4, 2016 (12 pages).
Kaul et al., "HIV-1 infection and AIDS: consequences for the central nervous system," Cell Death Differ., 2005, 12 Suppl 1: p. 878-892.
Krishnan et al., "Molecular adaptations underlying susceptibility and resistance to social defeat in brain reward regions," Cell, 2007, 131(2): p. 391-404.
Kull et al., "Mixtures of Quaternary Ammonium Compounds and Long-chain Fatty Acids as Antifungal Agents," Applied Microbiology, 1961, 9(6):538-541.
Langer, "Controlled release of macromolecules," Chem. Tech., 1982, 12:98-105.
Lee et al., "Preventing Allograft Rejection by Targeting Immune Metabolism," Cell Rep, 2015, 13:760-70.
Lentz et al., "Changes in MRS neuronal markers and T cell phenotypes observed during early HIV infection," Neurology, 2009, 72(17): p. 1465-1472.
Li et al., "Learning and reconsolidation implicate different synaptic mechanisms," Proc Natl Acad Sci U S A, 2013, 110:4798-803.
Mak et al. "Neuroimaging correlates of cognitive impairment and dementia in Parkinson's disease," Parkinsonism Relat Disord 2015, 21(8):862-70.
Marvel et al., "Cognitive and neurological impairment in mood disorders," Psychiatr Clin North Am, 2004; 27(1):19-viii.
McArthur et al., "Human immunodeficiency virus-associated neurocognitive disorders: Mind the gap," Ann. Neurol., 2010, 67(6): p. 699-714.
McGaugh, "Memory—a century of consolidation," Science, 2000, 287:248-51.
Pawlik et al., "Hepatic glutamine transporter activation in burn injury: role of amino acids and phosphatidylinositol-3-kinase," Am. J. Physiol. Gastrointest. Liver Physiol., 2000, 278(4):G532-G541.
Potter et al., "Neurological sequelae induced by alphavirus infection of the CNS are attenuated by treatment with the glutamine antagonist 6-diazo-5-oxo-l-norleucine," J. Neurovirol., 2015, 21(2):159-73.
Potter et al., "Targeting the glutamatergic system for the treatment of HIV-associated neurocognitive disorders," J Neuroimmune Pharmacol, 2013, 8:594-607.
Pugh et al., "Selective effects of peripheral lipopolysaccharide administration on contextual and auditory-cue fear conditioning," Brain Behav Immun, 1998, 12:212-29.
Rahn et al., "Inhibition of glutamate carboxypeptidase II (GCPII) activity as a treatment for cognitive impairment in multiple sclerosis," PNAS, 2012, 109(49):20101-6.
Robertson et al., "The prevalence and incidence of neurocognitive impairment in the HAART era," AIDS, 2007, 21(14): p. 1915-1921.
Roybal et al., "Mania-like behavior induced by disruption of Clock," Proceedings of the National Academy of Sciences of the United states of America, 2007, 104(15): p. 6106-6411.
Saenz et al., "Atteinte de la mémoire épisodique verbale dans la sclérose en plaques : revue critique des processus cognitifs concernés et de leur exploration," Rev Neurol (Paris), 2015, 171:624-645.
Sailasuta, N., et al., "Change in brain magnetic resonance spectroscopy after treatment during acute HIV infection," PLoS One, 2012, 7(11): p. e49272.
Sambrook et al., "Molecular Cloning. A Laboratory Manual," 3rd ed., Cold Spring Harbor Laboratory Press, Cold Spring Harbor, 2001.

(56) References Cited

OTHER PUBLICATIONS

Shijie J et al., "Blockade of glutamate release from microglia attenuates experimental autoimmune encephalomyelitis in mice," Tohoku J. Exp. Med., 2009, 217:87-92.

Sidman et al., "Controlled release of macromolecules and pharmaceuticals from synthetic polypeptides based on glutamic acid," Biopolymers, 1983, 22:547-556.

Simioni et al., "Cognitive dysfunction in HIV patients despite long-standing suppression of viremia," AIDS, 2010, 24(9): p. 1243-1250.

Srikanth et al., "Synthesis, screening and quantitative structure—activity relationship (QSAR) studies of some glutamine analogues for possible anticancer activity," Bioorganic and Medicinal Chemistry, 2002, 10(7):2119-2131.

Suzuki et al., "Memory reconsolidation and extinction have distinct temporal and biochemical signatures," J Neurosci, 2004, 24:4787-95.

Extended European Search Report issued in corresponding European Application No. 16833636.0, dated Feb. 12, 2019, 8 pages.

Abo-Ghalia M, et al., "Synthesis of inhibitors of the meso-diaminopimelate-adding enzyme from *Escherichia coli*", International Journal of Peptide and Protein Resea, Munksgaard, Coppenhagen, DK, vol. 32(No. 3), Sep. 1, 1998, pp. 208-222.

\* cited by examiner

GLUTAMINE ANTAGONISTS FOR THE TREATMENT OF COGNITIVE DEFICITS AND PSYCHIATRIC DISORDERS

CROSS-REFERENCE TO RELATED APPLICATIONS

This application is a continuation-in-part of PCT/US2016/044825, filed Jul. 29, 2016, that claims the benefit of U.S. Provisional Application Nos. 62/199,317 and 62/199,566, both filed Jul. 31, 2015, the contents of which are incorporated herein by reference in their entirety.

FEDERALLY SPONSORED RESEARCH OR DEVELOPMENT

This invention was made with government support under OD017877 and DA037611 awarded by the National Institutes of Health (NIH). The government has certain rights in the invention.

BACKGROUND

Cognitive deficits are implicated in various disorders, such as neurodegenerative, neurological, psychiatric disorders, and viral diseases, such as human immunodeficiency virus (HIV) or acquired immunodeficiency syndrome (AIDS).

Parkinson's disease (PD) is a neurodegenerative condition that affects multiple cognitive aspects. For example, mild cognitive impairment (PD-MCI) is a comorbidity often found in PD and is associated with a progression toward dementia (PDD) (Mak et al. *Parkinsonism Relat Disord*, 2015. 21(8):862-70).

Multiple sclerosis (MS) is similarly fraught with cognitive deficits, such as memory impairments, particularly impairment of verbal episodic memory (VEM) (Saenz et al. *Rev Neurol (Paris)*, 2015. pii: S0035-3787(15)00688-8).

Mood disorders are common psychiatric illnesses that cause significant disability and mortality worldwide. Neurocognitive changes, such as quantifiable decreases in attention, executive function, and recall memory, have been reported in patients with mood disorders (Marvel and Paradiso. *Psychiatr Clin North Am.* 2004; 27(1):19-viii). For example, in major depression, cognitive impairment can be severe and widespread, at times meeting the definition for dementia. Similarly, the acute phase of bipolar disorder can result in cognitive impairment that progresses to a stuporous state.

Human immunodeficiency virus-1 (HIV-1) affects more than 30 million people worldwide. The effects of HIV-1 worsen when it results either directly or indirectly in one or more neurological disorders. HIV-associated neurocognitive disorders (HAND) remains a prevalent disorder and one of the central health issues in patients with chronic HIV infection on cART (Zink, J Neuroimmune Pharmacol, 2007. 2(1): p. 14-9). HAND encompasses a hierarchy of progressive neurocognitive impairments including asymptomatic neurocognitive impairment (ANI), mild neurocognitive disorder (MND), and severe HIV-associated dementia (HAD), the latter characterized by cognitive, motor and behavioral abnormalities (McArthur, et al., Ann. Neurol., 2010. 67(6): p. 699-714; Antinori, et al., Neurology, 2007. 69(18): p. 1789-1799; Kaul, et al., Cell Death Differ., 2005. 12 Suppl 1: p. 878-892). In a recent study examining HIV-infected adults recruited from six university clinics across the United States, nearly half of HIV-infected individuals without confounding conditions had some form of HAND (Heaton, et al., Neurology, 2008. 75(23): p. 2087-96). Clinical symptoms associated with HAND include, but are not limited to, impaired short-term memory, reduced mental concentration, weakness, slowness of hand and leg movement, all of which can be accompanied by behavioral disorders, such as depression, personality disorders, lethargy, and social withdrawal.

Broad use of cART has markedly reduced the prevalence of HIV-associated dementia (HAD) but it has had limited effect on milder forms of HAND, which now constitute the majority of new cases of HIV neurological disease (Harezlak, et al., AIDS, 2011. 25(5): p. 625-633; Heaton, et al., J. Neurovirol., 2011. 17(1): p. 3-16; Robertson, et al., AIDS, 2007. 21(14): p. 1915-1921). Mild HAND presents clinically as a range of neurocognitive impairments (NCI) that do not meet the diagnostic criteria of HAD (Antinori, et al., Neurology, 2007. 69(18): p. 1789-1799) and we refer to this entity here as HIV-NCI. The biological basis of HIV-NCI is largely unknown and there is currently no treatment. The impairments are often diagnosed in treated individuals with high CD4 levels, sustained HIV suppression in plasma, and low or undetectable virus in the cerebrospinal fluid (Harezlak, et al., AIDS, 2011. 25(5): p. 625-633; Simioni, et al., AIDS, 2010. 24(9): p. 1243-1250). Consistent with this mild peripheral disease profile, analyses of autopsy brain tissues from patients who died with HIV-NCI indicate minimal pathological changes, low virus burdens, and mildly dysregulated gene expression in the brain compared to HAD/HIVE (Borjabad, et al., PLoS Pathog., 2011. 7(9): p. e1002213; Everall, et al., J. Neurovirol., 2009. 15(5-6): p. 360-370; Gelman, et al., PLoS One, 2012. 7(9): p. e46178). Brain imaging by $^1$H-MRS suggests low-level brain inflammation and metabolic changes in neurons consistent with dysfunction rather than neuronal apoptosis (Chang, et al., Antivir. Ther., 2003. 8(1): p. 17-26; Lentz, et al., Neurology, 2009. 72(17): p. 1465-1472; Sailasuta, et al., PLoS One, 2012. 7(11): p. e49272). Recent metabolomic analysis of cerebrospinal fluid from patients with mild HAND indicates a link between dysregulation of energy metabolism in the brain and extent of cognitive impairment (Dickens, et al., AIDS, 2015. 29(5):559-569). The neuropsychological symptoms of mild HAND suggest diffuse synaptodendritic injury spanning large regions of the brain from cortex to striatum to thalamus (Ellis, et al., Nat. Rev. Neurosci., 2007. 8(1): p. 33-44); however, there is little direct documentation of such injury as brain autopsies are rare. It is presently unclear why cART is largely ineffective in preventing or reversing HIV-NCI.

Accordingly, a need exists for methods of treating cognitive deficits, including those associated with neurodegenerative disorders, neurological diseases, psychiatric disorders, and viral disorders, including HAND, and in particular HIV-NCI.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology. Current Protocols in Immunology. Current Protocols in Protein Science, and Current Protocols in Cell Biology*, all John Wiley & Sons, N.Y., edition as of December 2008; Sambrook, Russell, and Sambrook, *Molecular Cloning. A Laboratory Manual*. 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact-.shtml.

In some aspects, the presently disclosed subject matter provides the use of glutamine antagonists, such as DON, LDONV, azaserine, and acivicin, and prodrugs and analogs thereof at doses less than that used for their anticancer efficacy to selectively abrogate cognitive deficits resulting from HIV infection including those defining HIV-associated neurocognitive disorders without dementia and those included in the definition of HIV dementia.

Accordingly, in some aspects, the presently disclosed subject matter provides a method for treating a subject having a cognitive deficit, the method comprising administering to the subject at least one glutamine antagonist in an amount effective to treat the cognitive deficit.

In some aspects, the presently disclosed subject matter involves the use of at least one glutamine antagonist for treating a cognitive deficit in a subject in need thereof.

In some aspects, the presently disclosed subject matter relates to the use of at least one glutamine antagonists for preparation of a medicament for the treatment of a cognitive deficit in a subject in need thereof.

In some aspects, the presently disclosed subject matter provides a pharmaceutical composition comprising at least one glutamine antagonist in an amount effective to treat a cognitive deficit, and a pharmaceutically acceptable carrier, diluent, or excipient.

In some aspects, the presently disclosed subject matter provides a method for treating a subject having a mood or anxiety disorder, the method comprising administering to the subject at least one glutamine antagonist in an amount effective to treat the mood or anxiety disorder.

In particular aspects, the glutamine antagonist is selected from the group consisting of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV) and prodrugs or analogs thereof.

In particular aspects, the glutamine antagonist is a compounds of the disclosure having formula (I), formula (IIA), formula (IIB), and formula (III), and the pharmaceutically acceptable salts thereof.

In more particular aspects, the cognitive deficit is due to the human immunodeficiency virus (HIV) infection. In such aspects, the cognitive deficit defines HIV-associated neurocognitive disorders occurring without dementia, or those in association with HIV dementia.

In more particular aspects, the cognitive deficits may be due to other distal mechanisms than HIV infection, such as accumulation of beta-amyloid in patients at early stages of Alzheimer's disease or inflammation in multiple sclerosis, but are proximally mechanistically similar to cognitive deficits induced by HIV.

Applicant has found that compounds of the disclosure having formula (I), formula (IIA), formula (IIB), and formula (III) are stable in plasma, liver microsomes, liver tissue, and gastrointestinal tissue, yet these compounds are cleaved in certain tissue cells to liberate DON. The unexpected properties of compounds having formula (I), formula (IIA), formula (IIB), and formula (III) result in a surprising improvement in therapeutic index for treating a condition, disease, or disorder with DON and provide the maximum therapeutic benefit to a subject in need of such treatment.

Applicant has also found unexpectedly that compounds of the disclosure having formula (I), formula (IIA), formula (IIB), and formula (III) exhibit unexpected enhanced CSF to plasma partitioning after administration, making them uniquely useful for the treatment a condition, disease, or disorder where central nervous system (CNS) penetration is required.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
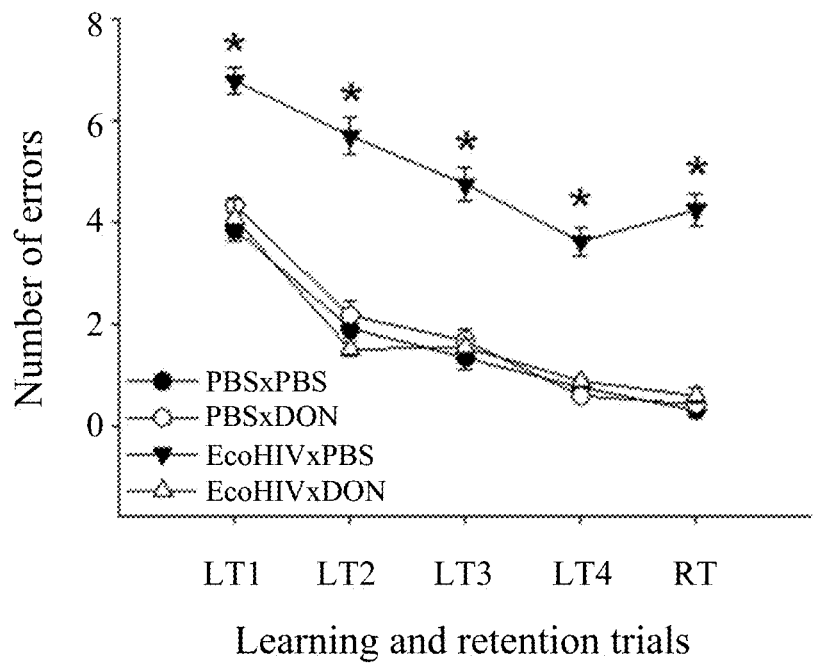
Figure 1B:
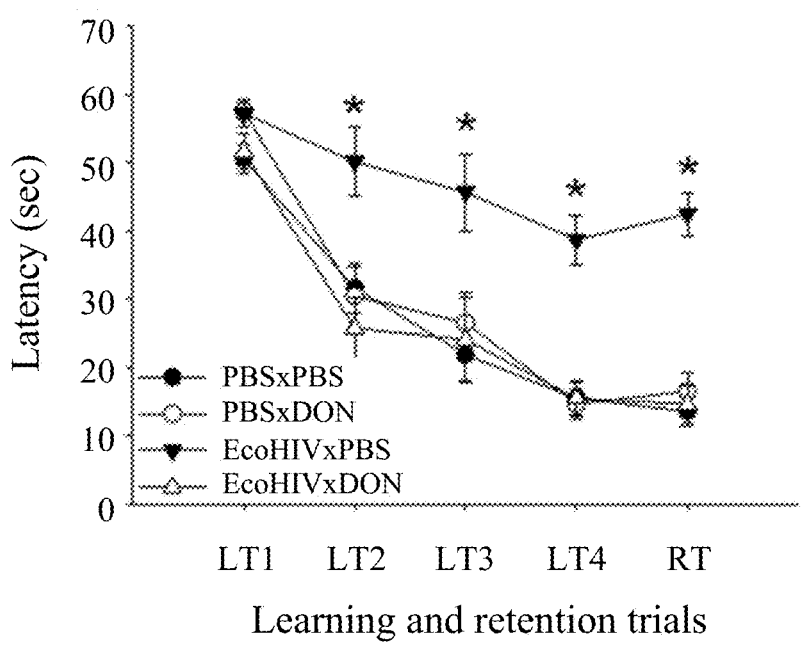
Figure 1C:
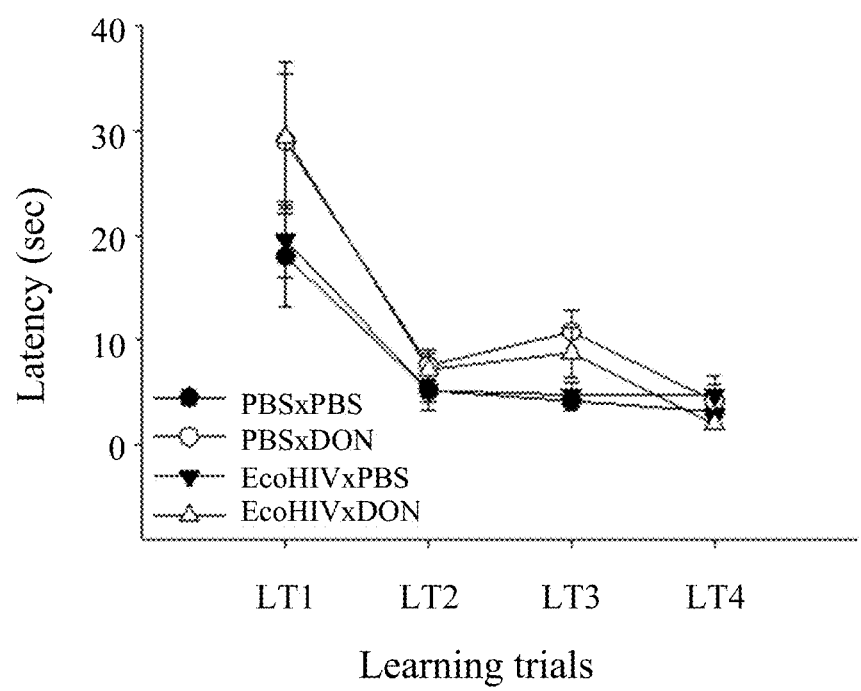
Figure 2A:
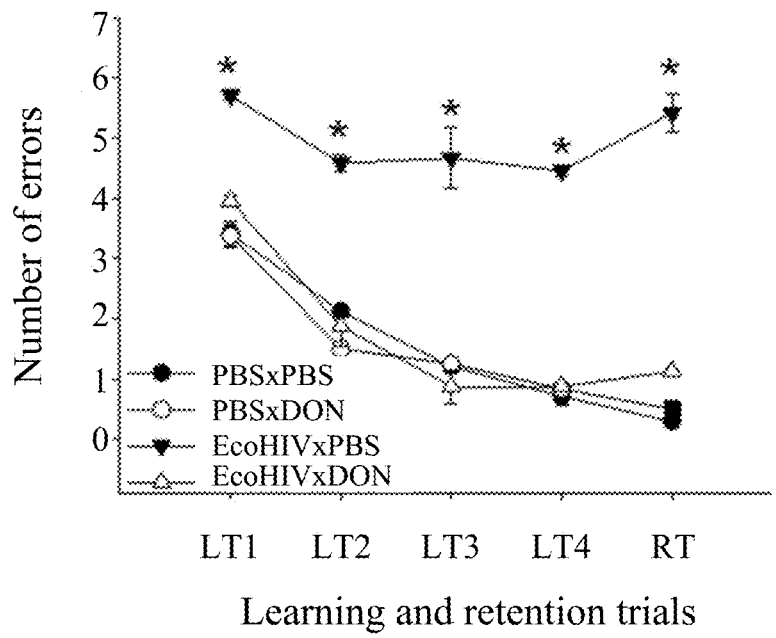
Figure 2B:
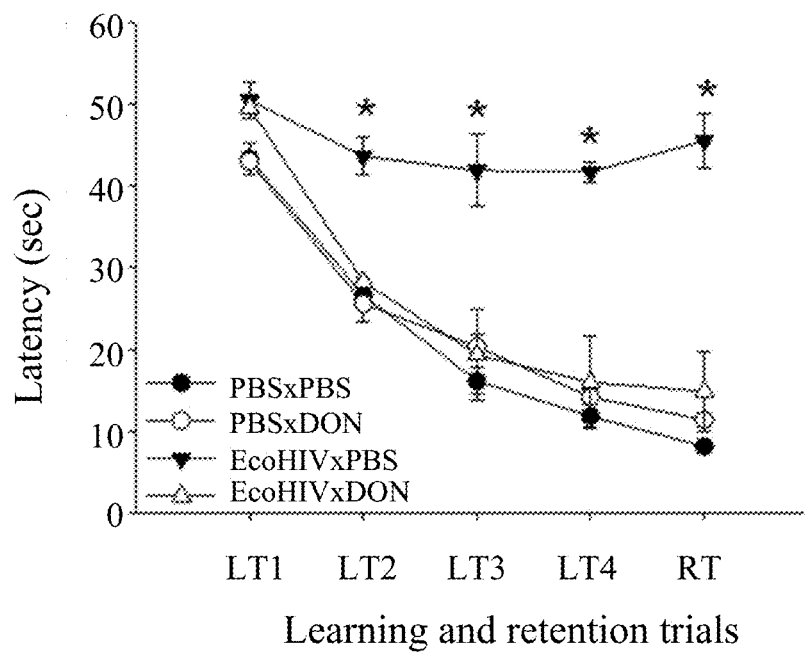
Figure 2C:
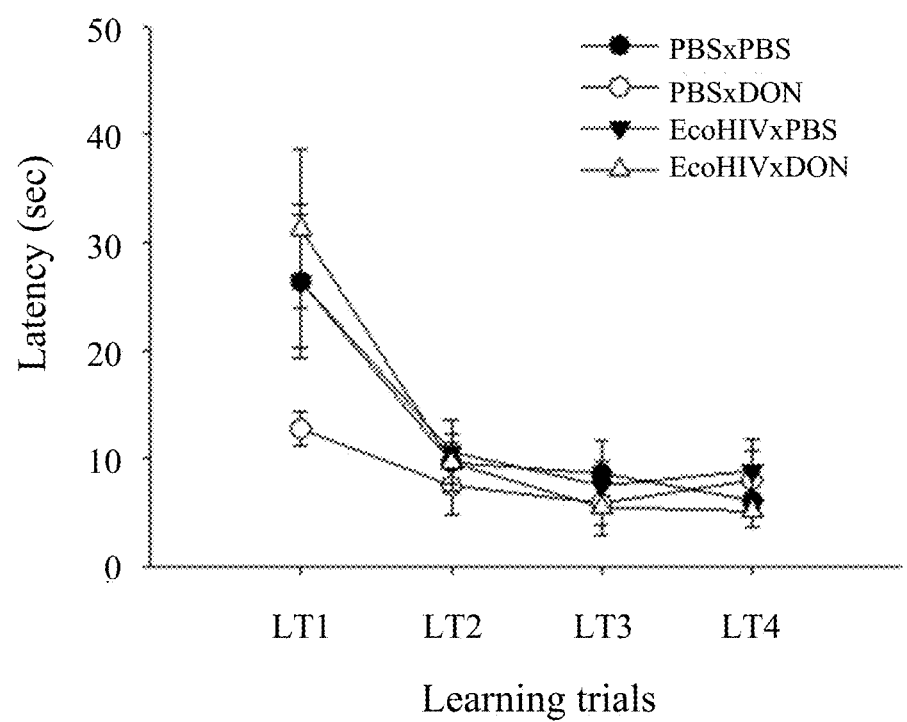

Having thus described the presently disclosed subject matter in general terms, reference will now be made to the accompanying Figures, which are not necessarily drawn to scale, and wherein:

FIG. 1A, FIG. 1B, and FIG. 1C are graphs showing that prophylactic treatment of mice with DON prevents development of HIV-induced cognitive impairment. Six-week old C57Bl mice were treated with DON (1 mg/kg) or saline; treatment was continued on alternate days until the end of the experiment. 24 h after the first DON administration, groups of mice (n=8) were infected with EcoHIV ($2 \times 10^6$ pg p24/mouse) or treated with saline by intraperitoneal inoculation. Thirty days after infection, all mice were subjected to behavioral testing in a radial arm water test measuring learning and memory. The data shown represent means+/− SD of the consecutive last 3 days of water maze testing for the indicated groups of mice measuring (FIG. 1A) the number of errors made by each animal in finding the hidden platform; (FIG. 1B) the time (latency) it took each animal to find the hidden platform; and (FIG. 1C) the time it took each animal to find the visible platform, as control for visual and motor acuity of treated and untreated animals. LT1-LT4: consecutive one-minute learning trials; RT: retention (memory) trial (the ability of an animal to recall location of platform after a rest period). (*): $p \leq 0.05$ for pair-wise comparison by student t-test between infected/untreated mice and individual other groups;

FIG. 2A, FIG. 2B, and FIG. 2C are graphs showing DON treatment of EcoHIV infected mice with demonstrable cognitive impairment completely abrogates cognitive disease.

Figure 3A:
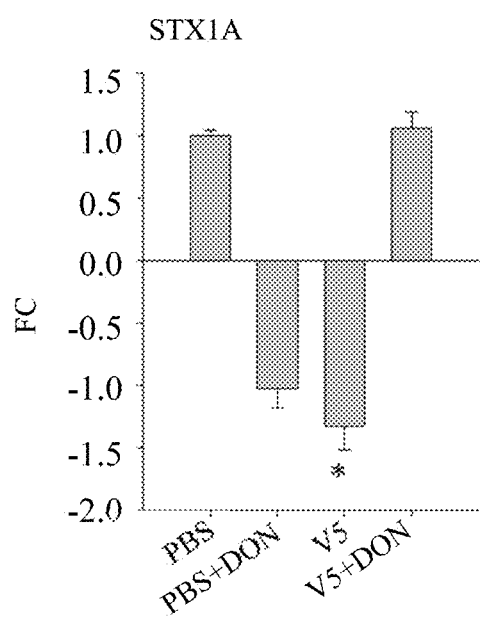
Figure 3B:
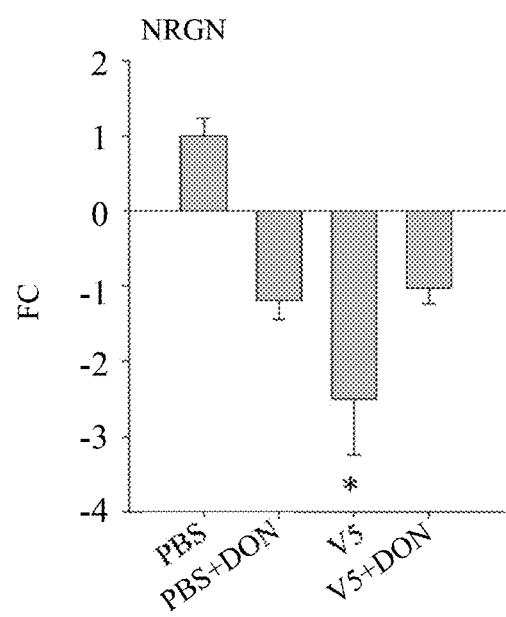
Figure 4A:
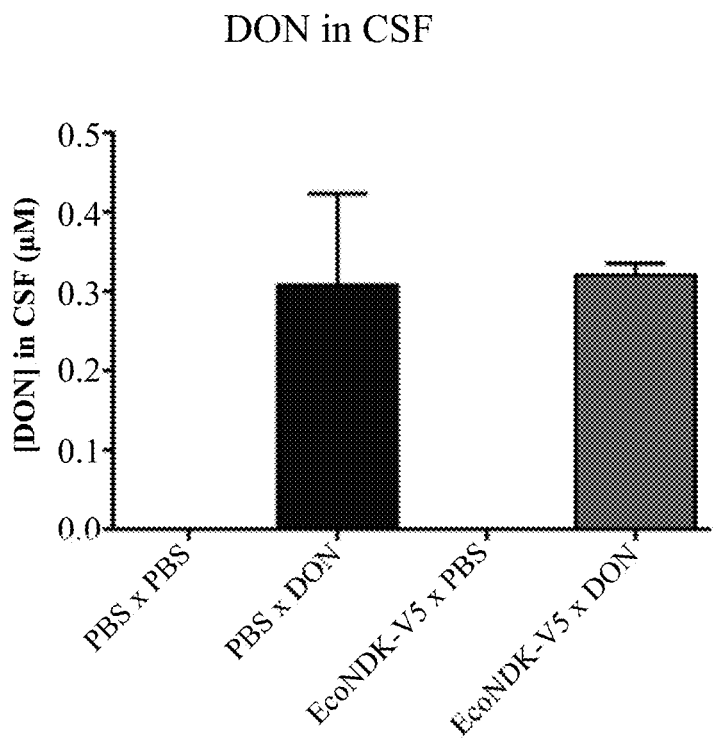
Figure 4B:
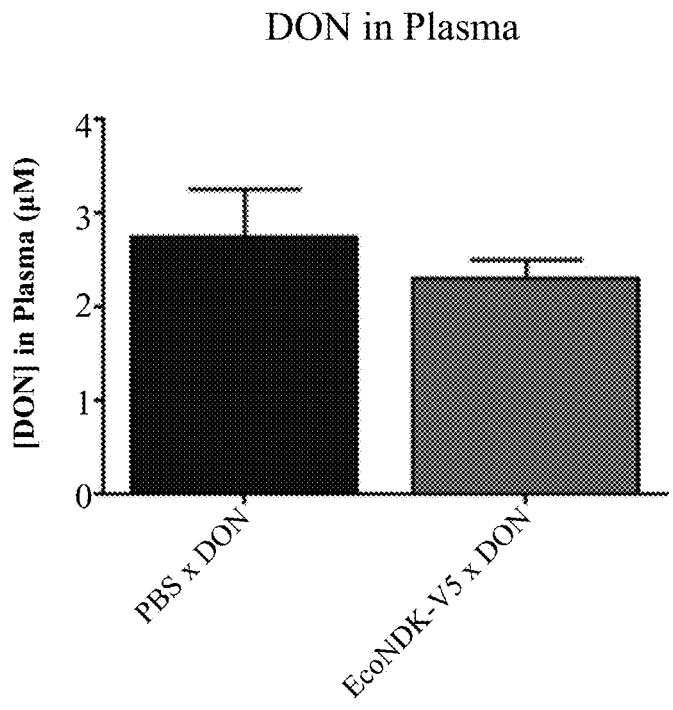
Figure 4C:
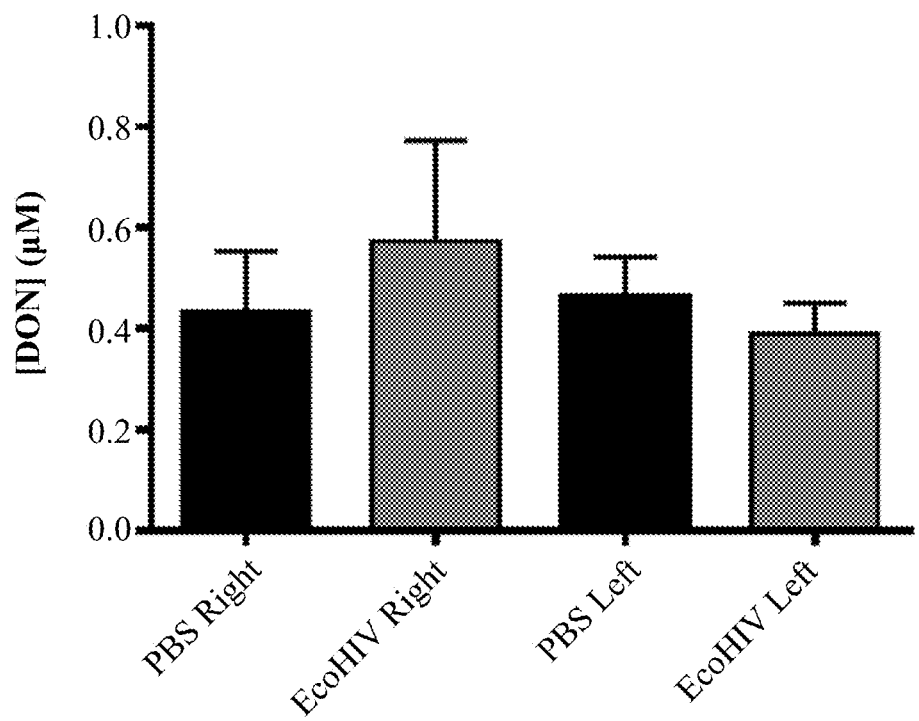
Figure 5A:
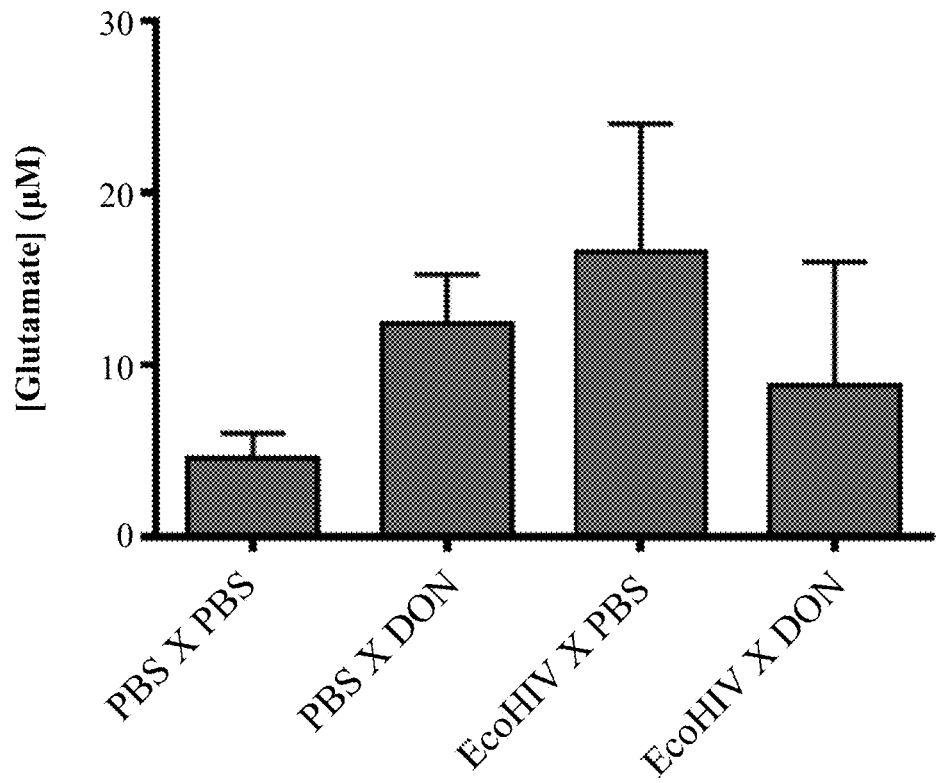

Mice, EcoHIV and DON doses, and experimental procedures were as described in the DON prophylaxis experiment shown in FIG. 1A, FIG. 1B, and FIG. 1C, except that DON administration started 26 days after infection and was continued on alternate days until completion of behavioral testing. Water maze tests were initiated 30 days after infection. FIG. 2A shows the number of errors made by each animal in finding the hidden platform; FIG. 2B shows the time (latency) it took each animal to find the hidden platform; and FIG. 2C shows the time it took each animal to find the visible platform, as control for visual and motor acuity of treated and untreated animals. LT1-LT4: consecutive one-minute learning trials; RT: retention (memory) trial (the ability of an animal to recall location of platform after a rest period). (*): p≤0.05 for pair-wise comparison by student t-test between infected/untreated mice and individual other groups;

FIG. 3A and FIG. 3B are graphs showing that DON treatment reversed HIV-mediated down-modulation of STX1A and NRGN in correlation with abrogation of cognitive defect of EcoHIV-infected mice. Relative extent of gene expression tested by QPCR in basal ganglia brain tissues obtained from mice tested in DON treatment reversal experiment shown in FIG. 2A, FIG. 2B, and FIG. 2C. The tissues were collected 15 min after the last DON treatment;

FIG. 4A, FIG. 4B, and FIG. 4C are graphs showing that micromolar DON levels were observed in plasma, CSF and basal ganglia in mice treated in the behavioral experiments. Mouse samples were analyzed for DON using LC-MS/MS 15 minutes post administration. DON was quantifiable in all samples provided. Fifteen minutes after dosing, the concentration of DON averaged from about 2.5 μM to 3 μM in plasma, and from about 0.3 μM to about 0.5 μM in brain tissue and CSF. No significant difference was observed between mice infected with PBS and EcoHIV; and FIG. 5A is a graph showing glutamate in CSF from mice treated with DON. Glutamate was quantified via LC/MS. Glutamate levels tended to be higher in EcoHIV mice versus PBS mice. In addition, DON tended to decrease the glutamate in the EcoHIV mice; however, no significant differences were found among the treatment groups by one-way ANOVA analysis.

Figure 5B:
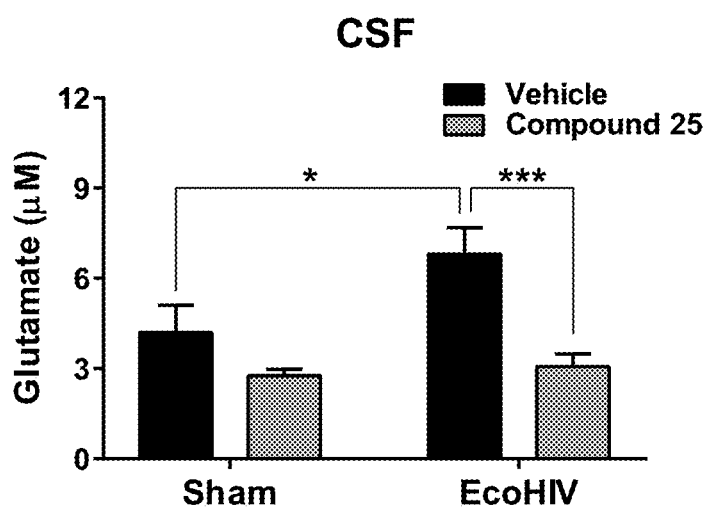

FIG. 5B is a graph showing that compound 25 reversed EcoHIV-induced increases in CSF glutamate concentration.

Figure 6:
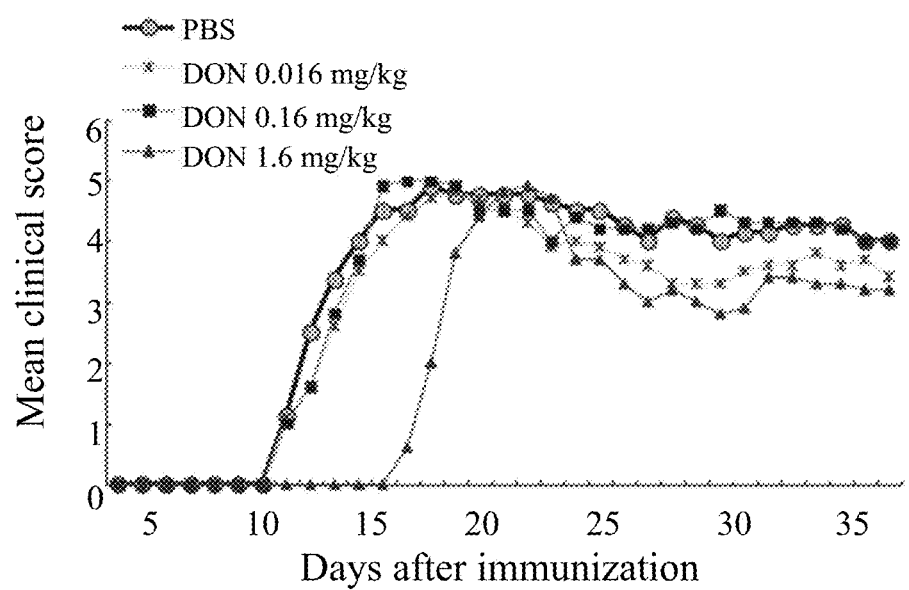

FIG. 6 is a graph showing a previous study demonstrated that DON administered i.p. q.a.d at a dose of 1.6 mg/kg from the time of immunization attenuates EAE (Shijie, et al., 2009), but lower doses were ineffective. No other studies on DON in EAE have been reported.

Figure 7:
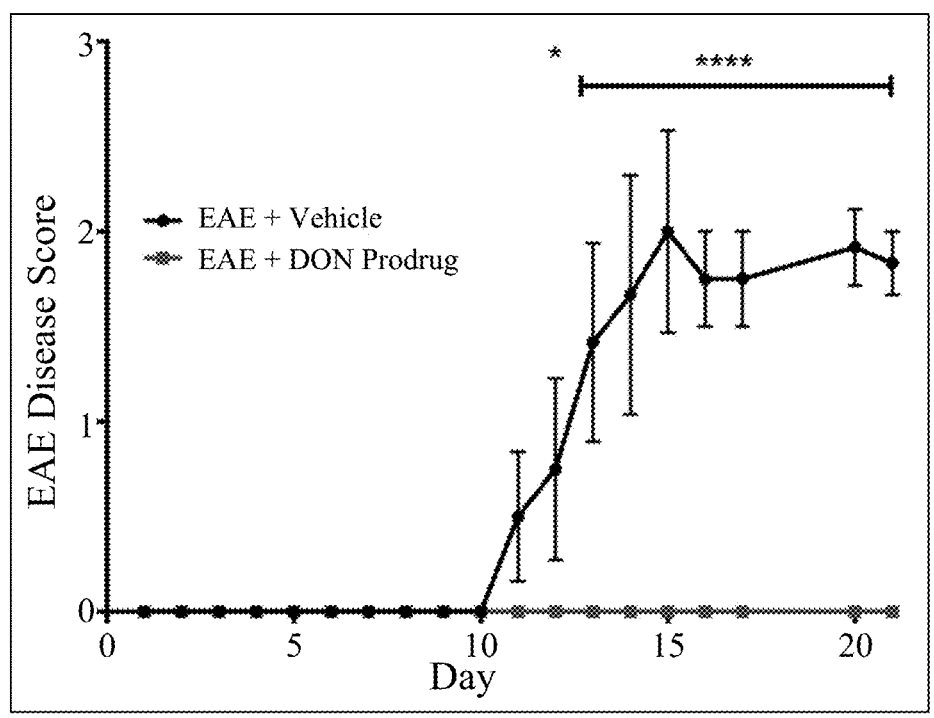

FIG. 7 is a graph showing the effect of an exemplary DON prodrug on EAE disease score when administered from the time of immunization. The DON prodrug completely prevents the development of physical signs of EAE. Significantly different from EAE+Vehicle at *P<0.05, ****P<0.0001. 2-way ANOVA treatment effect P=0.0001, n=6-8.

Figure 8A:
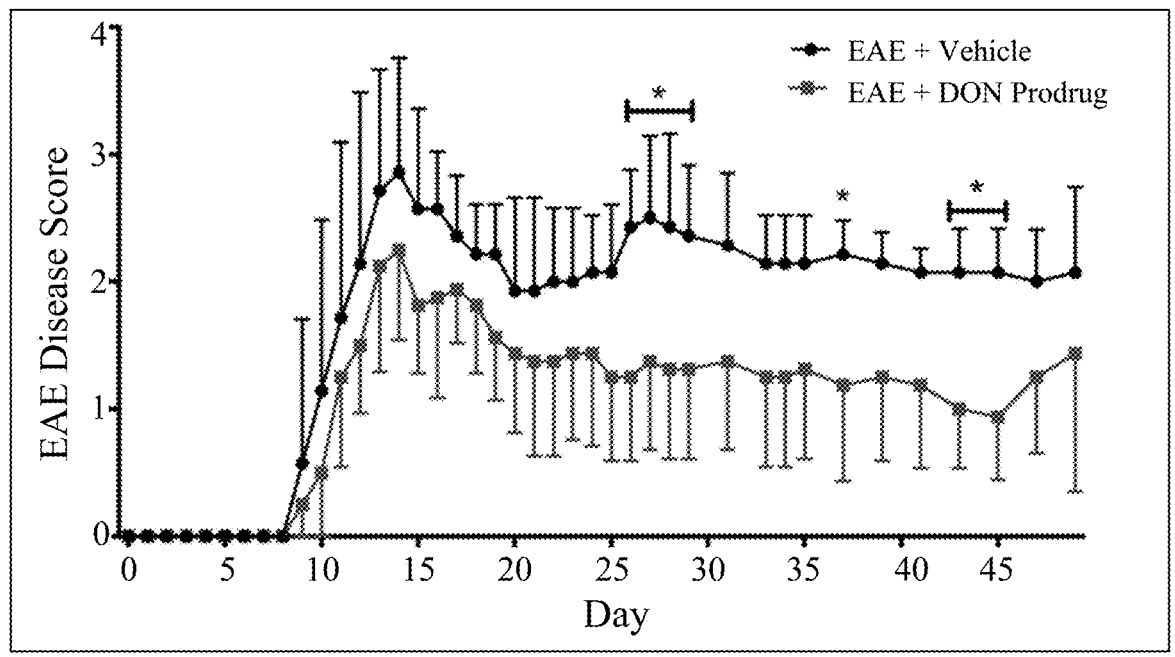
Figure 8B:
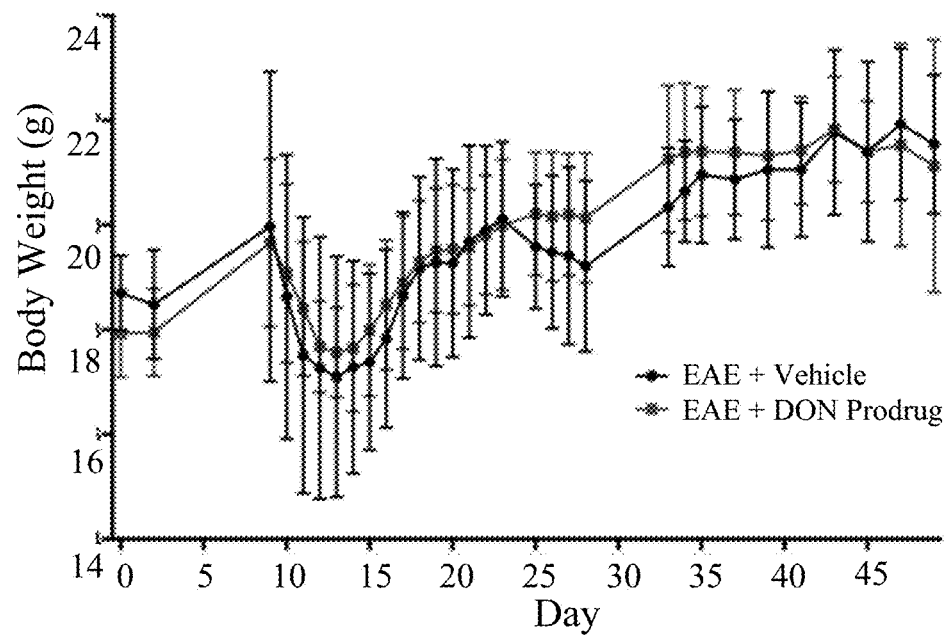

FIG. 8A and FIG. 8B are graphs showing the effects of an exemplary DON prodrug on EAE disease score and body weight when administered from the time of disease onset (i.e. EAE score ≥1). FIG. 8A shows the exemplary DON prodrug significantly improves disease severity as measured by EAE disease score. FIG. 8B shows the exemplary DON prodrug has no effect on body weight as compared to vehicle-treated EAE mice. Significantly different from EAE+Vehicle at *P<0.05, 2-way ANOVA treatment effect on EAE Disease Score P<0.05, n=7-8.

Figure 9:
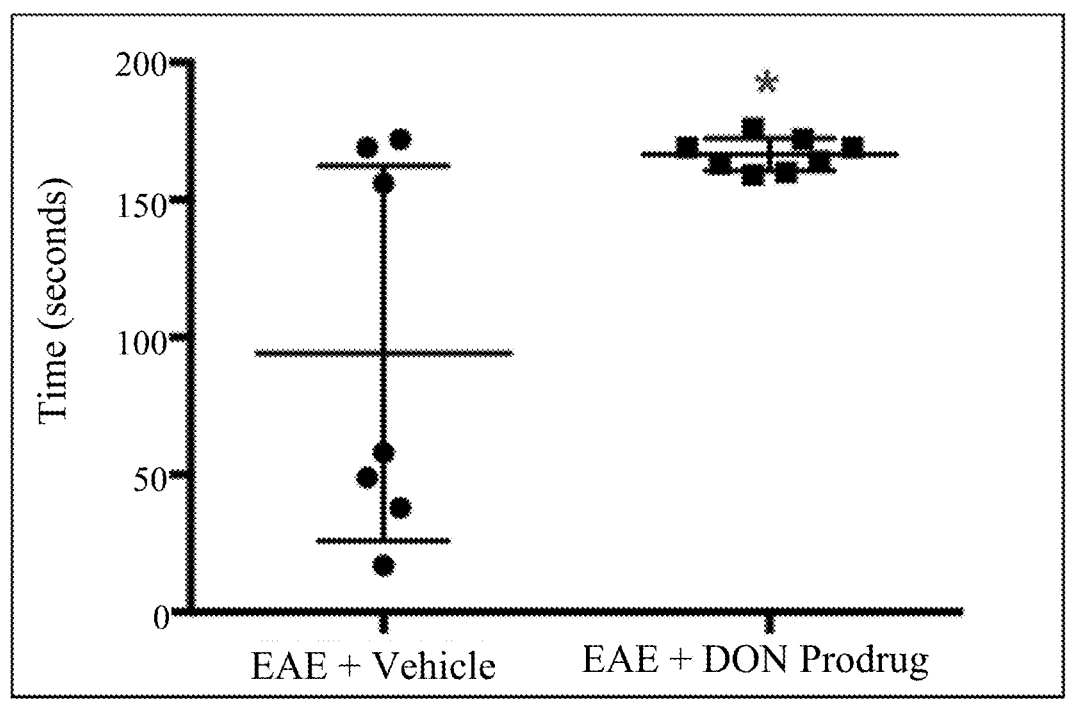

FIG. 9 is a graph showing the effects of an exemplary DON prodrug on cognition as measured by Barnes maze primary latency in EAE treatment paradigm. EAE mice administered the exemplary DON prodrug for >8 wks from the time of disease onset with equivalent EAE disease scores to EAE+Vehicle mice (P<0.99) demonstrated superior long term memory with significantly increased primary latency deltas in the Barnes maze (Day 1 Trial 1-Day 4 Trial 1). Significantly different from EAE+Vehicle at *P<0.05, n=7-8.

Figure 10A:
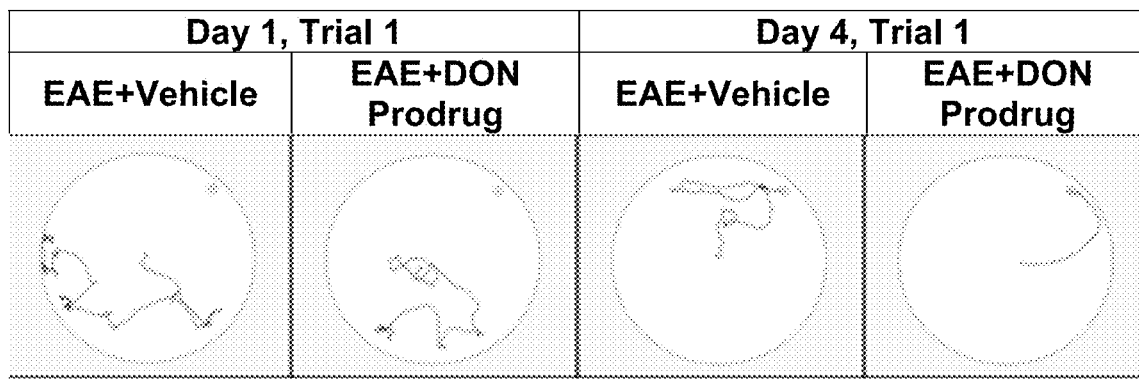
Figure 10B:
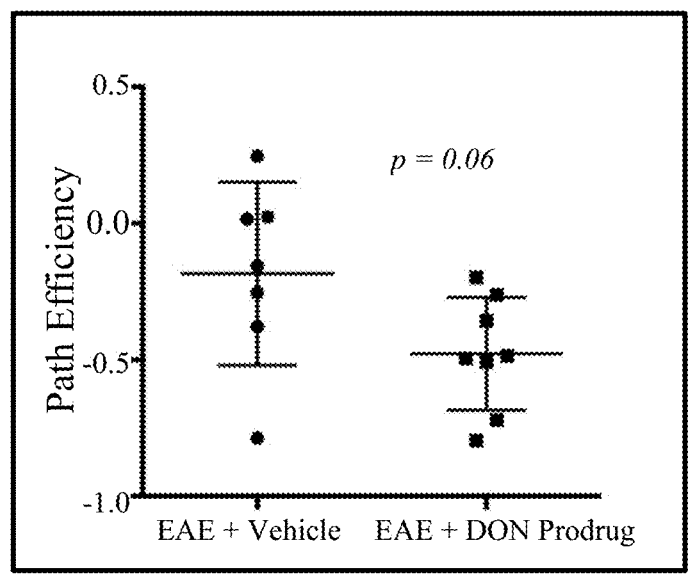

FIG. 10A and FIG. 10B are Barnesmaze paths and a graph, respectively, showing the effects of an exemplary DON prodrug on cognition as measured by Barnes maze path efficiency in EAE treated mice. EAE mice administered the exemplary DON prodrug from the time of disease onset for >8 weeks until equivalent EAE disease scores to EAE+Vehicle mice was achieved (P<0.99), demonstrated improved Barnes maze performance. FIG. 10A shows sample representative Barnes maze paths tracked by ANY-maze software of the first trial of Day 1 or Day 4 of Barnes maze testing. FIG. 10B shows decreased path efficiency delta (Day 1 Trial 1-Day 4 Trial 1) in mice treated with the exemplary DON prodrug versus vehicle suggesting superior learning abilities in EAE+DON prodrug mice. n=7-8.

Figure 11A:
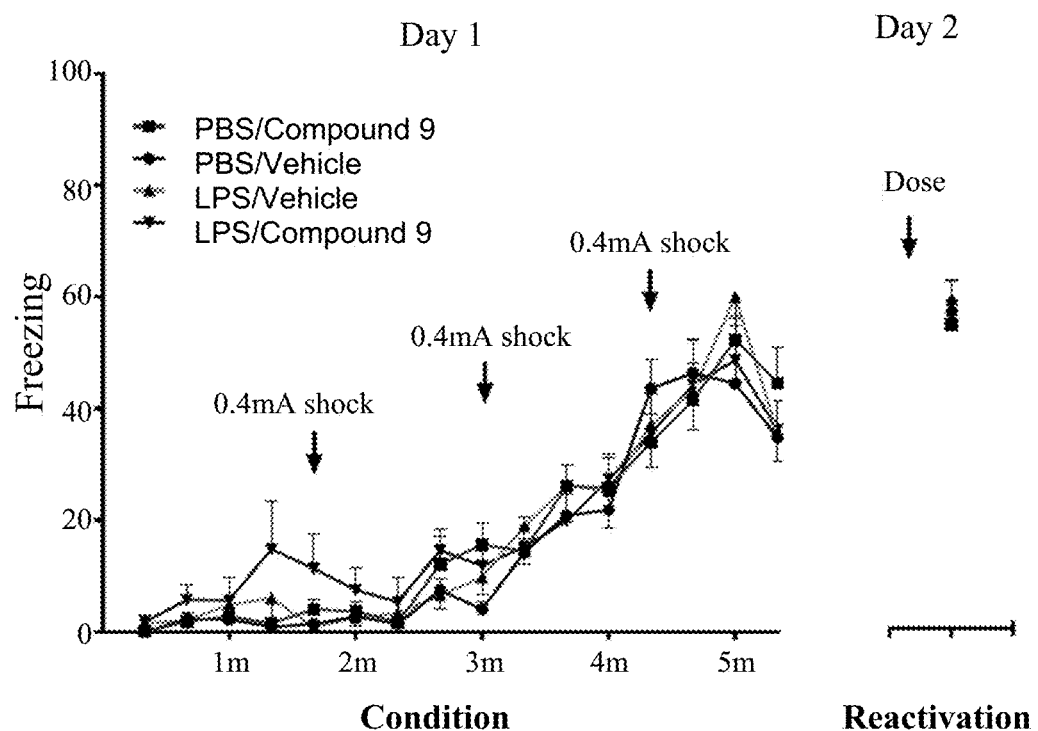
Figure 11B:
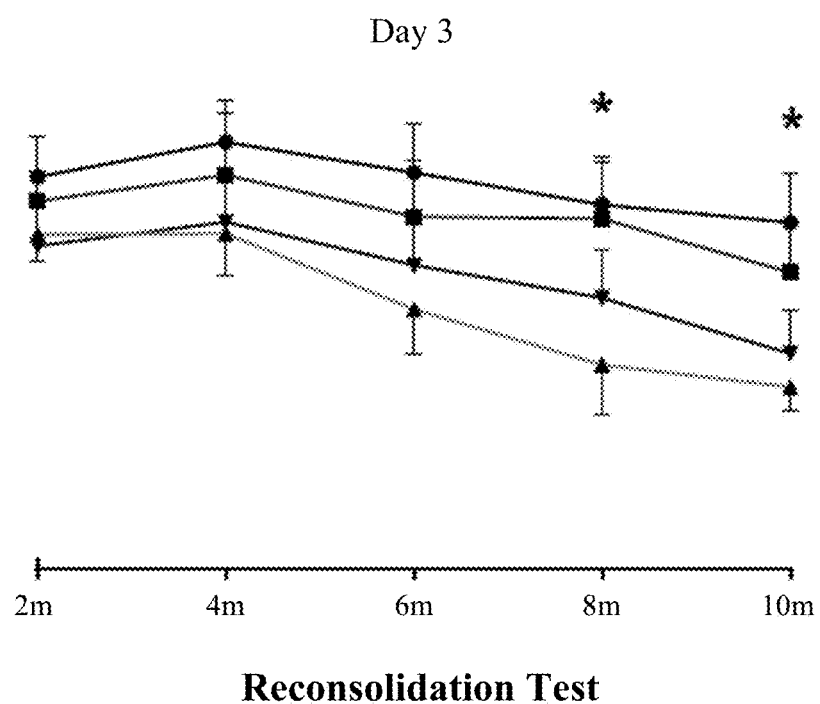

FIG. 11A and FIG. 11B are graphs showing DON prodrug (9) attenuated LPS-induced deficits in reconsolidation memory. All mice exhibited normal conditioning (Day 1) and reactivation (Day 2) of contextual fear. However mice that received LPS (0.3 mg/kg, i.p.) on Day 2 exhibited reduced freezing during the reconsolidation test (Day 3) indicating memory impairment. *p<0.05 LPS/Vehicle vs. PBS/Vehicle. Co-administration of 9 (1.9 mg/kg, i.p.) with LPS on Day 2 attenuated the LPS-induced deficits in reconsolidation memory. Mice that received LPS and 9 were indistinguishable from PBS/Veh mice on Day 3.

Figure 12A:
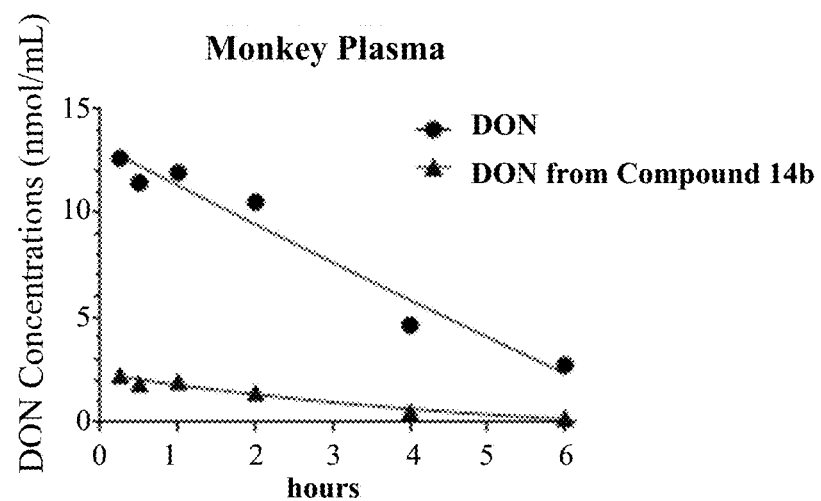

FIG. 12A is a graph demonstrating different DON plasma profiles in Monkey for DON and compound 14b.

Figure 12B:
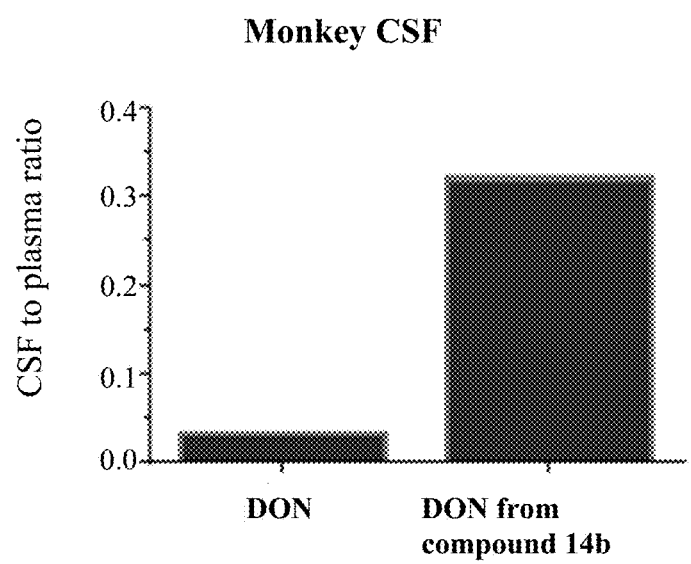

FIG. 12B is a graph showing that compound 14b exhibited enhanced CSF:plasma ratio of DON in Monkey.

Figure 13A:
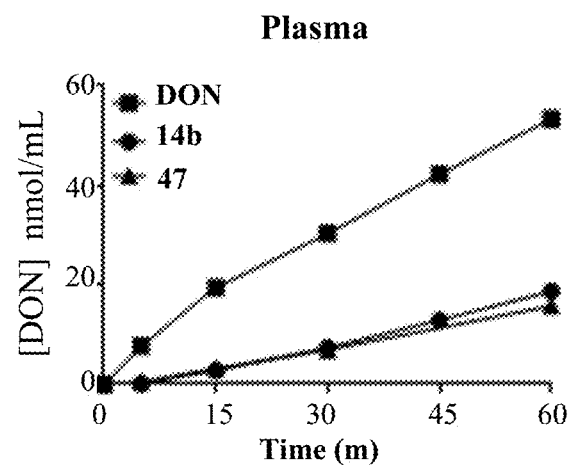

FIG. 13A is a graph demonstrating different DON plasma profiles in swine for DON, compound 14b and compound 47.

Figure 13B:
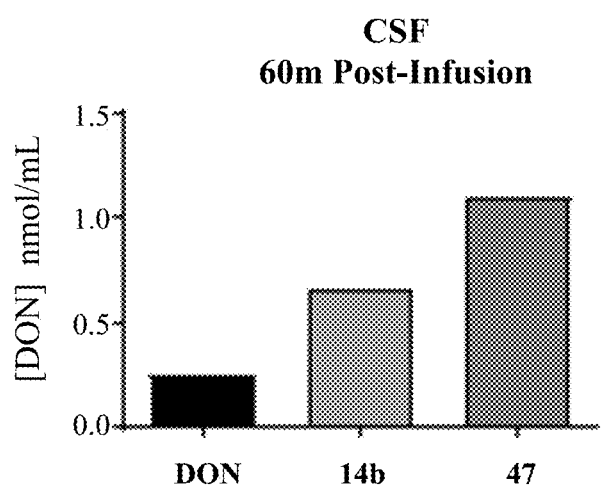
Figure 13C:
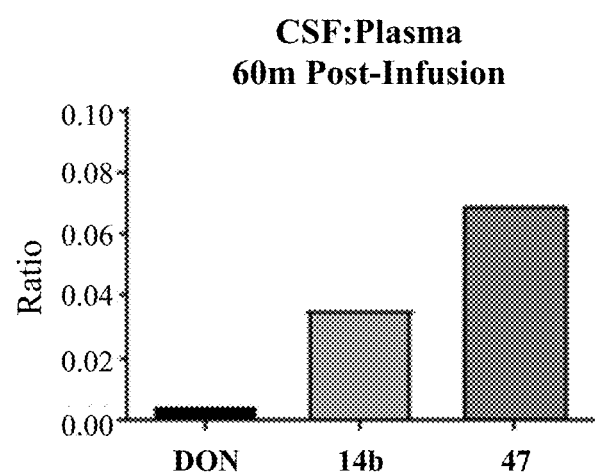

FIG. 13B is a graph showing that compounds 14b and 47 exhibited enhanced CSF delivery of DON at 60 min post-administration in swine FIG. 13C is a graph showing that compounds 14b and 47 exhibited enhanced CSF:plasma ratio of DON at 60 min post-administration in swine.

Figure 14A:
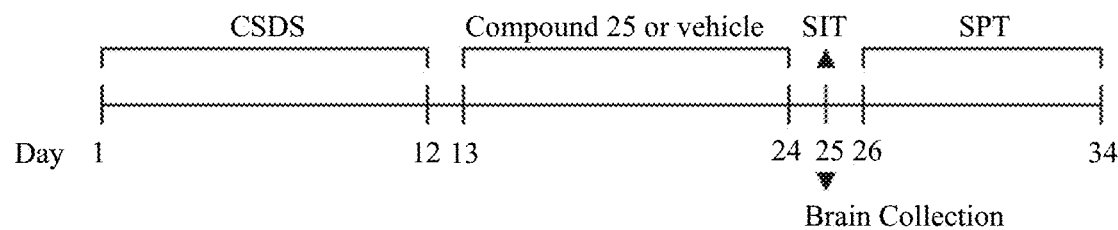

FIG. 14A is an experimental timeline showing Chronic Social Defeat Stress (CSDS) followed by chronic administration of compound 25.

Figure 14B:
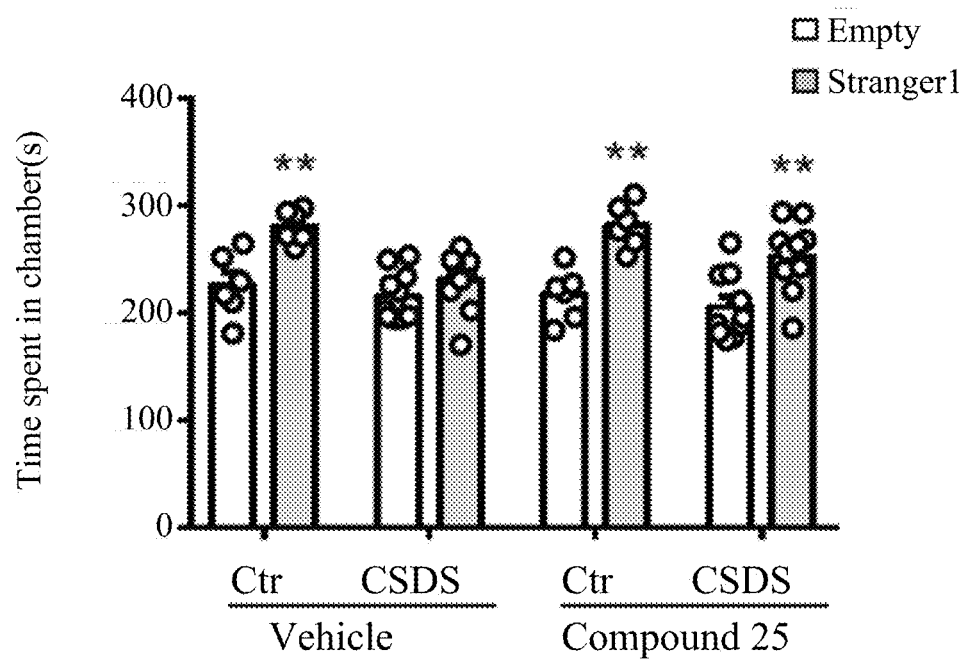
Figure 14C:
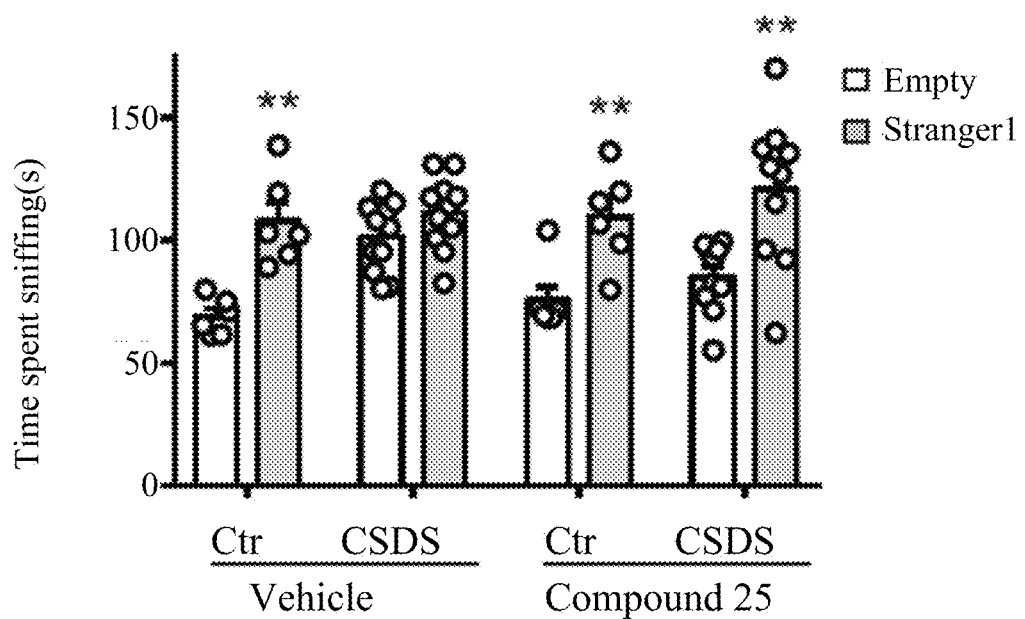

FIG. 14B and FIG. 14C are graphs showing that compound 25 treatment ameliorated deficits in social behaviors induced by CSDS.

FIG. 15A, FIG. 15B, FIG. 15C, and FIG. 15D are graphs showing that DON prevented cognitive decline in the EcoHIV-infected mouse model of HAND.

Figure 16:
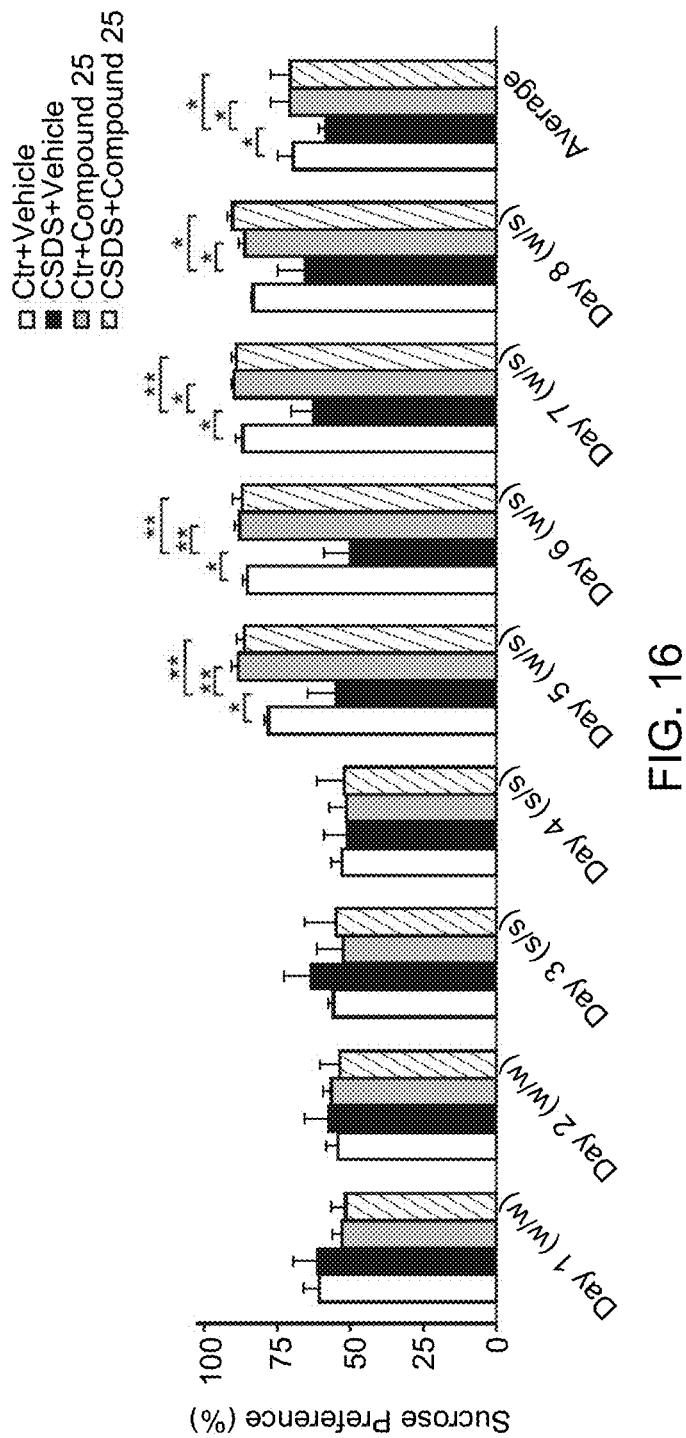

FIG. 16 is a graph showing that compound 25 reversed CSDS-induced reduction in sucrose preference test (SPT), a measure of anhedonia-like behavior.

DETAILED DESCRIPTION

The presently disclosed subject matter now will be described more fully hereinafter with reference to the accompanying Figures, in which some, but not all embodiments of the presently disclosed subject matter are shown.

Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Methods of Treatment for Cognitive Deficits

Glutamine antagonists, such as 6-diazo-5-oxo-L-norleucine (DON), azaserine, and acivicin, have been shown to have anti-cancer activities in multiple preclinical and clinical studies. The toxicity of such glutamine antagonists at doses necessary for their anticancer effects, however, has hampered their clinical development for cancer and other indications. The presently disclosed subject matter provides the use of glutamine antagonists, or prodrugs and analogs thereof, at doses less than that used for their anticancer efficacy, for treating cognitive deficits, including HIV-NCI (e.g., ANI, MND, etc., as well as those included as part of the diagnostic criteria of HIV-associated dementia, also known as AIDS dementia complex. In some aspects, the presently disclosed subject matter provides the use of glutamine antagonists, or prodrugs and analogs thereof, at doses less than that used for their anticancer efficacy, for treating cognitive deficits due to, or associated with, neurodegenerative disorders, such as multiple sclerosis, Parkinson's disease, schizophrenia, Alzheimer's disease (AD), autism, or cognitive deficits due to neuroinflammation such as cerebral malaria or encephalitis.

In one embodiment, the presently disclosed subject matter provides a method for treating a subject having a cognitive deficit, the method comprising administering to the subject at least one glutamine antagonist, or prodrug or analog thereof, in an amount effective to treat the cognitive deficit.

In another embodiment, the presently disclosed subject matter involves the use of at least one glutamine antagonist, or prodrug or analog thereof, for treating a cognitive deficit in a subject in need thereof.

In yet other embodiments, the presently disclosed subject matter provides a pharmaceutical composition comprising at least one glutamine antagonist, or a prodrug or analog thereof, in an amount effective to treat a cognitive deficit, and a pharmaceutically acceptable carrier, diluent, or excipient.

As used herein, a "cognitive deficit" refers to a disease, disorder, or condition that is characterized by impairment of the mental processes of perception, learning, memory, judgment, and/or reasoning. In some embodiments, the cognitive deficit is selected from the group consisting of dementia, and mild to moderate cognitive decline (the latter resulting in gradual incapacitation of daily activities).

As used herein, the term "dementia" refers to a terminal disease or disorder that involves inability to think, learn, and remember such that a person's daily functioning is affected among other disabilities such as seizures and motor detects. As used herein, the term "cognitive decline" refers to a gradual decrease in a person's mental processes of perception, learning, memory, judgment, and reasoning. A "mild cognitive decline" refers to a decrease in a person's mental processes of perception, memory, judgment, and reasoning that is less than a 40% decrease, less than a 30% decrease, less than a 20% decrease, or less than a 10% decrease as compared to the person's cognitive ability before the cognitive decline occurred.

In some embodiments, the cognitive deficit is due to a viral infection. In some embodiments, the cognitive deficit is due to the human immunodeficiency virus (HIV) infection. In some embodiments, the subject is infected with HIV that is latent in T lymphocytes, other viruses that may be latent (e.g., JCV, Herpes) and the subject shows few or no symptoms of the infection except cognitive deficits. In such embodiments, the methods of treating and/or preventing may include administering to the subject an effective amount of an anti-viral agent.

In an aspect, the presently disclosed subject matter provides a method for treating a cognitive deficit in a subject due to a viral infection, the method comprising administering to the subject at least one glutamine antagonist, or prodrug or analog thereof, in an amount effective to treat the cognitive deficit.

In another aspect, the presently disclosed subject matter involves the use of at least one glutamine antagonist, or prodrug or analog thereof, for treating a cognitive deficit in a subject due to a viral infection.

In yet other aspects, the presently disclosed subject matter provides a pharmaceutical composition comprising at least one glutamine antagonist, or a prodrug or analog thereof, in an amount effective to treat a cognitive deficit due to a viral infection in a subject, and a pharmaceutically acceptable carrier, diluent, or excipient.

In an aspect, the presently disclosed subject matter provides a method of preventing a cognitive deficit in a subject having a viral infection, the method comprising administering to the subject at least one glutamine antagonist, or prodrug or analog thereof, in an amount effective to prevent the cognitive deficit.

In another aspect, the presently disclosed subject matter involves the use of at least one glutamine antagonist, or prodrug or analog thereof, for preventing a cognitive deficit in a subject having a viral infection.

In yet other aspects, the presently disclosed subject matter provides a pharmaceutical composition comprising at least one glutamine antagonist, or a prodrug or analog thereof, in an amount effective to prevent a cognitive deficit in a subject having a viral infection, and a pharmaceutically acceptable carrier, diluent, or excipient.

In an aspect, the presently disclosed subject matter provides a method for treating HIV-induced cognitive impairment in a subject in need thereof, the method comprising administering to the subject at least one glutamine antagonist, or prodrug or analog thereof, in an amount effective to treat the HIV-induced cognitive impairment in the subject.

In another aspect, the presently disclosed subject matter involves the use of at least one glutamine antagonist, or prodrug or analog thereof, for treating HIV-induced cognitive impairment in a subject in need thereof.

In yet other aspects, the presently disclosed subject matter provides a pharmaceutical composition comprising at least one glutamine antagonist, or a prodrug or analog thereof, in an amount effective to treat HIV-induced cognitive impairment in a subject in need thereof, and a pharmaceutically acceptable carrier, diluent, or excipient.

In an aspect, the presently disclosed subject matter provides a method of preventing HIV-induced cognitive impairment in a subject in need thereof, the method comprising administering to the subject at least one glutamine antagonist, or prodrug or analog thereof, in an amount effective to prevent the cognitive deficit.

In another aspect, the presently disclosed subject matter involves the use of at least one glutamine antagonist, or prodrug or analog thereof, for preventing HIV-induced cognitive impairment in a subject in need thereof.

In yet other aspects, the presently disclosed subject matter provides a pharmaceutical composition comprising at least one glutamine antagonist, or a prodrug or analog thereof, in an amount effective to prevent HIV-induced cognitive impairment in a subject in need thereof, and a pharmaceutically acceptable carrier, diluent, or excipient.

In some embodiments, the cognitive deficit is part of but not complete clinical definition HIV-associated dementia, also known as AIDS dementia complex. In some embodiments, the cognitive deficit is ACI. In some embodiments, the cognitive deficit is MND. In some embodiments, the cognitive deficit is HIV-NCI.

Generally, HIV can affect any part of the nervous system, such as the brain, spinal cord, or peripheral nerves. Depending on which part of the nervous system is involved, symptoms of neurologic disease in HIV-infected individuals may include memory loss, headache, dizziness, weakness, numbness, pain, vision changes, or trouble walking.

It should be appreciated that some neurologic disorders, such as opportunistic infections, primary central nervous system lymphoma (PCNSL), and HIV-associated dementia (HAD) occur only in patients with advanced AIDS. Other neurologic conditions, however, such as HIV-associated neuropathy and HIV-associated asymptomatic neurocognitive impairment (ANI), and HIV-associated mild neurocognitive disorder (MND), occur even in patients with well-controlled HIV.

More particularly, neurologic conditions associated with HIV include, but are not limited to, cerebral toxoplasmosis, cryptococcal meningitis, cytomegalovirus (CMV) encephalitis, distal symmetric polyneuropathy (DSP), HIV-associated dementia (HAD), HIV-associated myelopathy, HIV-associated myopathy, immune reconstitution inflammatory syndrome, inflammatory demyelinating polyneuropathy, mononeuropathy multiplex, primary CNS lymphoma (PCNSL), progressive multifocal leukoencephalopathy (PML), and progressive polyradiculopathy.

HIV-associated dementia (HAD) occurs primarily in subjects with more advanced HIV infection (AIDS). Symptoms include, behavioral changes, and a gradual decline in cognitive function, including trouble with concentration, memory, and attention. Subjects with HAD also show progressive slowing of motor function and loss of dexterity and coordination. When left untreated, HAD can be fatal. It is rare when anti-retroviral therapy is used.

In some embodiments, cognitive deficits that may respond to DON or DON derivatives are not caused by virus infection but may be distally related to (caused by) factors believed to cause neurologic diseases, such as AD, MS, PD and schizophrenia.

In some embodiments, the cognitive deficit is due to, or associated with, a neurodegenerative disorder. A "neurodegenerative disorder" is a disease, disorder, or condition that is characterized by the progressive loss of the structure or function of neurons (e.g., degeneration or dysfunction of neurons or other neural cells). Some aspects of the presently disclosed subject matter relate to correcting cognitive defects associated with neurodegenerative diseases, disorders, or conditions including, but not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, porphyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, and epilepsy.

In particular embodiments, the cognitive deficit is due to, or associated with, multiple sclerosis.

In an aspect, the presently disclosed subject matter provides a method of treating a cognitive deficit in a subject having multiple sclerosis, the method comprising administering to the subject at least one glutamine antagonist, or prodrug or analog thereof, in an amount effective to treat the cognitive deficit.

In another aspect, the presently disclosed subject matter involves the use of at least one glutamine antagonist, or prodrug or analog thereof, for treating a cognitive deficit in a subject having multiple sclerosis.

In yet other aspects, the presently disclosed subject matter provides a pharmaceutical composition comprising at least one glutamine antagonist, or a prodrug or analog thereof, in an amount effective to treat a cognitive deficit in a subject having multiple sclerosis, and a pharmaceutically acceptable carrier, diluent, or excipient.

In an aspect, the presently disclosed subject matter provides a method of preventing a cognitive deficit in a subject having multiple sclerosis, the method comprising administering to the subject at least one glutamine antagonist, or prodrug or analog thereof, in an amount effective to prevent the cognitive deficit.

In another aspect, the presently disclosed subject matter involves the use of at least one glutamine antagonist, or prodrug or analog thereof, for preventing a cognitive deficit in a subject having multiple sclerosis.

In yet other aspects, the presently disclosed subject matter provides a pharmaceutical composition comprising at least one glutamine antagonist, or a prodrug or analog thereof, in an amount effective to prevent a cognitive deficit in a subject having multiple sclerosis, and a pharmaceutically acceptable carrier, diluent, or excipient.

In an aspect, the presently disclosed subject matter provides a method of treating a cognitive deficit in a subject having multiple sclerosis, the method comprising administering to the subject a prodrug of at least one glutamine antagonist in an amount effective to treat the cognitive deficit.

In another aspect, the presently disclosed subject matter involves the use of a prodrug of at least one glutamine antagonist for treating a cognitive deficit in a subject having multiple sclerosis.

In yet other aspects, the presently disclosed subject matter provides a pharmaceutical composition comprising at least one glutamine antagonist, or a prodrug or analog thereof, in an amount effective to treat a cognitive deficit in a subject having multiple sclerosis, and a pharmaceutically acceptable carrier, diluent, or excipient.

Some aspects of the presently disclosed subject matter relate to correcting cognitive defects associated other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Some aspects of the presently disclosed subject matter relate to correcting cognitive defects associated with a wide range of genetic brain diseases. For example, genetic brain diseases may include but are not limited to Adrenoleukodystrophy, Agenesis of the Corpus Callosum, Aicardi Syndrome, Alpers' Disease. Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly.

Some aspects of the presently disclosed subject matter relate to correcting cognitive defects associated with one or more conditions that are secondary to a disease, disorder, condition, or therapy having a primary effect outside of the nervous system selected from the group consisting of: peripheral neuropathy or neuralgia caused by diabetes, cancer, hepatitis, hepatic encephalopathy, kidney dysfunction, Colorado tick fever, diphtheria, leprosy, Lyme disease, polyarteritis nodosa, rheumatoid arthritis, sarcoidosis, Sjogren syndrome, syphilis, systemic lupus erythematosus, viral encephalitis, and amyloidosis. In some embodiments, the cognitive deficit is associated with hepatic encephalopathy. In some embodiments, the cognitive deficit is associated with viral encephalitis.

Some aspects of the presently disclosed subject matter relate to correcting cognitive defects associated with a neurodegenerative disease, disorder, or condition associated with pain selected from the group consisting of chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a tom ligament, and diabetes.

Some aspects of the presently disclosed subject matter relate to correcting cognitive defects associated with a neurodegenerative disease, disorder, or condition that is associated with one or more injuries to the nervous system. In particular embodiments, the one or more injuries to the nervous system is related to nerve damage caused by exposure to one or more agents selected from the group consisting of toxic compounds, heavy metals, industrial solvents, drugs, chemotherapeutic agents, dapsone, cholesterol lowering drugs, heart or blood pressure medications, and metronidazole.

In more particular embodiments, the one or more injuries to the nervous system is related to nerve damage caused by one or more conditions selected from the group consisting of burn, wound, surgery, accidents, ischemia, prolonged exposure to cold temperature, stroke, intracranial hemorrhage, and cerebral hemorrhage.

Some aspects of the presently disclosed subject matter relate to correcting cognitive defects associated with a psychiatric disorder. In particular embodiments, the psychiatric disorder is selected from the group consisting of schizophrenia, delusional disorder, schizoaffective disorder, schizophreniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

In another embodiment, the disclosure provides a method for treating a subject having a cognitive deficit or psychiatric disorder, the method comprising administering to the subject a compound, or a pharmaceutically acceptable salt thereof, having formula (I):

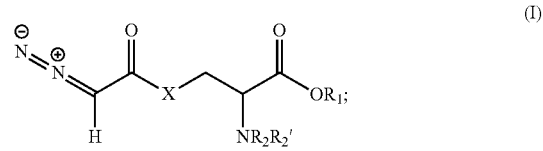

wherein:

X is selected from the group consisting of a bond, —O—, and —(CH$_2$)$_n$—, wherein n is an integer selected from the group consisting of 1, 2, 3, 4, 5, 6, 7, and 8;

R$_1$ is selected from the group consisting of C$_{1-6}$ alkyl and substituted C$_{1-6}$ alkyl;

R$_2$ is —C(=O)—O—(CR$_3$R$_4$)$_m$—O—C(=O)—R$_{10}$;

R$_2$' is selected from the group consisting of H, C$_1$-C$_6$ alkyl, and substituted C$_1$-C$_6$ alkyl;

each R$_3$ and R$_4$ is independently H, C$_1$-C$_6$ alkyl, substituted C$_1$-C$_6$ alkyl, aryl, substituted aryl, —(CR$_3$R$_4$)$_m$—NR$_5$R$_6$, or

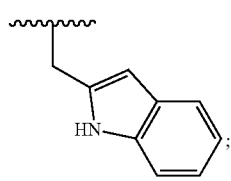 [SMILES: *Cc1cc2ccccc2[nH]1]

m is an integer selected from the group consisting of 1, 2, 3, 4, 5, 6, 7, and 8;

R$_5$ and R$_6$ is independently H or alkyl; and

R$_{10}$ is selected from the group consisting of alkyl, substituted alkyl, cycloalkyl, substituted cycloalkyl, monosaccharide, acylated monosaccharide, aryl, substituted aryl, heteroaryl, and substituted heteroaryl, in an amount effective to treat the cognitive deficit or psychiatric disorder.

In another embodiment, the disclosure provides a method for treating a subject having a cognitive deficit or psychiatric disorder, the method comprising administering to the subject a compound, or a pharmaceutically acceptable salt thereof, having formula (I), wherein X is —CH$_2$—. In another embodiment, X is —O—. In another embodiment, R$_1$ is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In another embodiment, m is 1; each R$_3$ and R$_4$ are independently H, C$_1$-C$_6$ alkyl, aryl or substituted aryl; and R$_{10}$ is selected from the group consisting of alkyl, substituted alkyl, cycloalkyl, substituted cycloalkyl, aryl, substituted aryl, heteroaryl, and substituted heteroaryl.

In another embodiment, the disclosure provides a method for treating a subject having a cognitive deficit or psychiatric disorder, the method comprising administering to the subject a compound, or a pharmaceutically acceptable salt thereof, having formula (II):

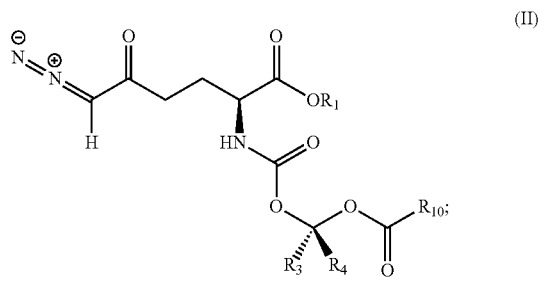

(II)

wherein:

R$_1$ is selected from the group consisting of H and C$_{1-6}$ alkyl;

R$_3$ and R$_4$ are independently selected from the group consisting of H, C$_1$-C$_6$ alkyl, substituted C$_1$-C$_6$ alkyl, aryl, and substituted aryl; and R$_{10}$ is C$_{1-6}$ alkyl.

In another embodiment, the disclosure provides a method for treating a subject having a cognitive deficit or psychiatric disorder, the method comprising administering to the subject a compound, or a pharmaceutically acceptable salt thereof, having formula (II), wherein R$_1$ is selected from the group consisting of methyl, ethyl, and isopropyl. In another embodiment, R$_3$ is H and R$_4$ is selected from the group consisting of methyl and phenyl. In another embodiment, R$_3$ is selected from the group consisting of methyl and phenyl, and R$_4$ is H. In another embodiment, R$_{10}$ is selected from the group consisting of isopropyl and tert-butyl.

In another embodiment, the disclosure provides a method for treating a subject having a cognitive deficit or psychiatric disorder, the method comprising administering to the subject a compound, or a pharmaceutically acceptable salt thereof, selected from the group consisting of:

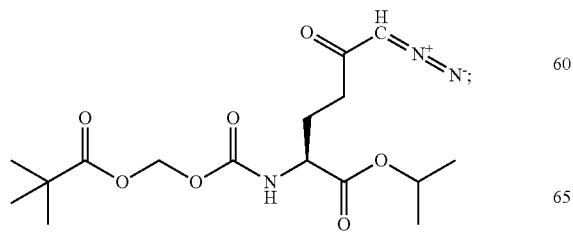

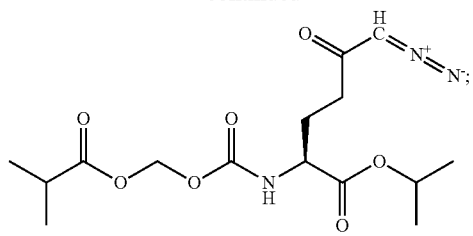

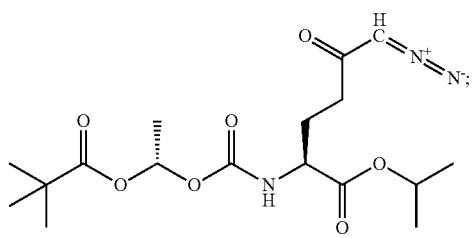

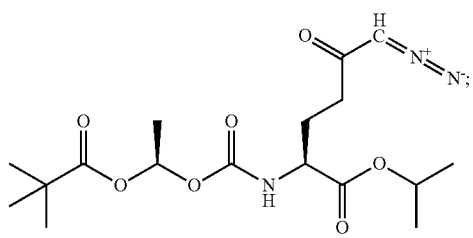

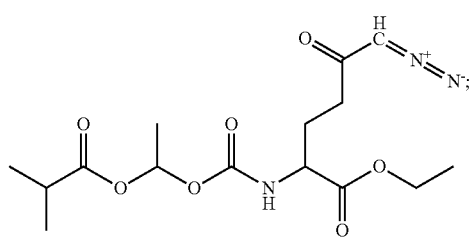

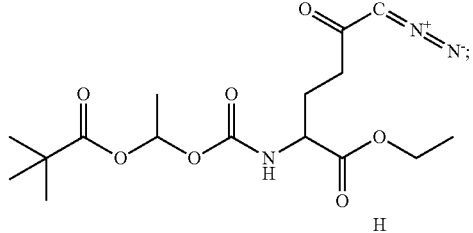

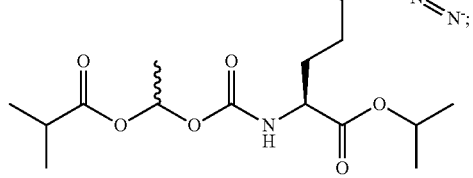

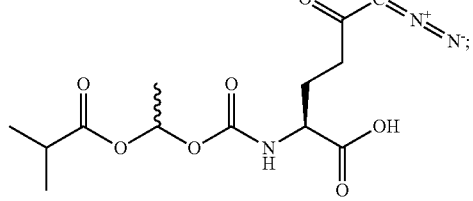

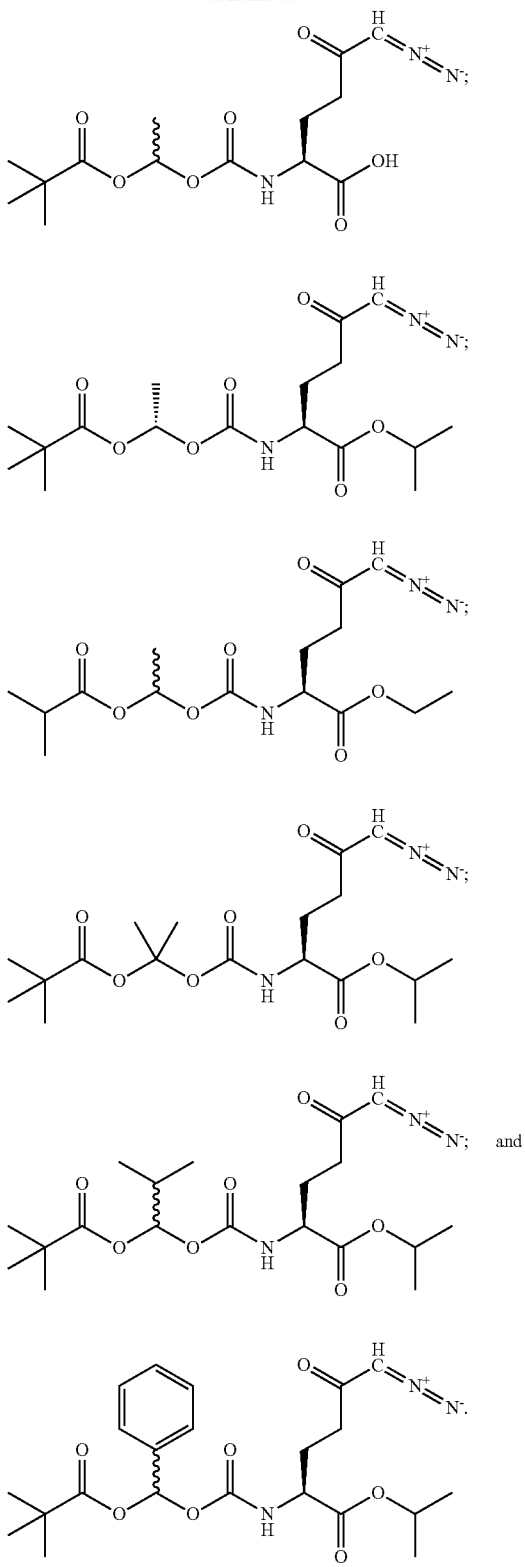

In another embodiment, the disclosure provides a method for treating a subject having a cognitive deficit or psychiatric disorder, the method comprising administering to the subject a compound, or a pharmaceutically acceptable salt thereof, selected from the group consisting of:

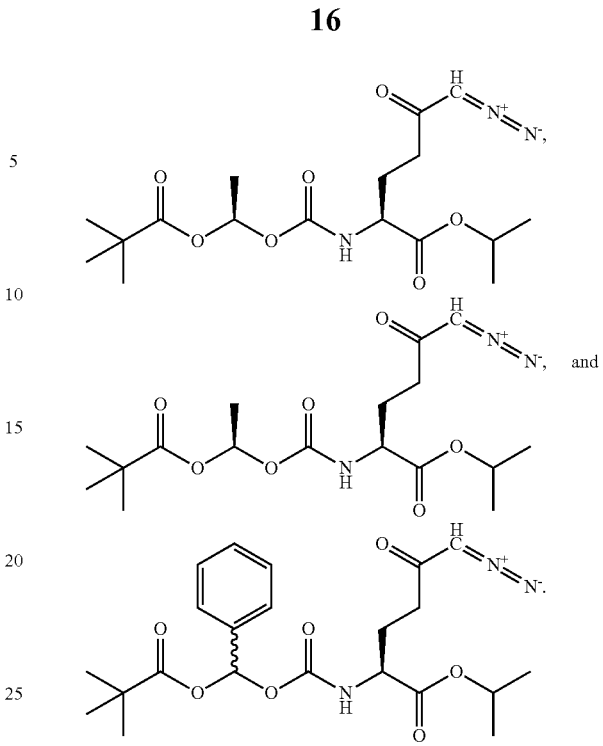

In another embodiment, the disclosure provides a method for treating a subject having a cognitive deficit, the method comprising administering to the subject a compound having formula (I) or formula (II), or a pharmaceutically acceptable salt thereof.

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is characterized by impairment of the mental processes of perception, learning, memory, judgment, and/or reasoning.

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is due to a viral infection. In another embodiment, the cognitive deficit is due to the human immunodeficiency virus (HIV). In another embodiment, the virus is latent.

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is selected from the group consisting of asymptomatic neurocognitive impairment (ANI) and mild neurocognitive disorder (MND).

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is associated with a neurodegenerative disorder.

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is associated with a psychiatric disorder.

In another embodiment, the disclosure provides a method for treating a subject having a cognitive deficit, the method comprising administering to the subject a compound having formula (I) or formula (II), or a pharmaceutically acceptable salt thereof, wherein the cognitive deficit is associated with multiple sclerosis.

In another embodiment, the disclosure provides a method of treating a subject having a psychiatric disorder, the method comprising administering to the subject a compound having formula (I) or formula (II), or a pharmaceutically acceptable salt thereof. In another embodiment, the psychiatric disorder is a mood disorder.

In another embodiment, the disclosure provides a method for treating a subject having a cognitive deficit, the method comprising administering to the subject a compound having formula (I) or formula (II), or a pharmaceutically acceptable salt thereof, wherein the cerebrospinal fluid (CSF)-to-plasma concentration ratio of 6-diazo-5-oxo-L-norleucine (DON) in the subject following administration is about 0.20 to about 5.0. In another embodiment, CSF-to-plasma concentration ratio of DON in the subject following administration is about 0.25 to about 5.0. In another embodiment, CSF-to-plasma concentration of DON in the subject following administration is about 0.30 to about 5.0. In another embodiment, CSF-to-plasma concentration ratio of DON in the subject following administration is about 0.35 to about 5.0. In another embodiment, CSF-to-plasma concentration ratio of DON in the subject following administration is about 0.35 to about 2.0. In another embodiment, CSF-to-plasma concentration ratio of DON in the subject following administration is about 0.35 to about 1.0. In another embodiment, CSF-to-plasma concentration ratio of DON in the subject following administration is about 0.35 to about 0.75. In another embodiment, CSF-to-plasma concentration ratio of DON in the subject following administration is about 0.35 to about 0.50.

The disclosure also provides the following particular embodiments.

Embodiment I

A method for treating a subject having a cognitive deficit, the method comprising administering to the subject at least one glutamine antagonist in an amount effective to treat the cognitive deficit.

Embodiment II

The method of Embodiment 1, wherein the cognitive deficit is characterized by impairment of the mental processes of perception, learning, memory, judgment, and/or reasoning.

Embodiment III

The method of Embodiment 1, wherein the cognitive deficit is due to a viral infection.

Embodiment IV

The method of Embodiment 3, wherein the cognitive deficit is due to the human immunodeficiency virus (HIV).

Embodiment V

The method of Embodiment 4, wherein the virus is latent.

Embodiment VI

The method of Embodiment 1, wherein the cognitive deficit is selected from the group consisting of asymptomatic neurocognitive impairment (ANI), mild neurocognitive disorder (MND), and HIV-associated dementia (HAD).

Embodiment VII

The method of Embodiment 1, wherein the cognitive deficit is associated with a neurodegenerative disorder and/or psychiatric disorder.

Embodiment VIII

The method of Embodiment 1, wherein the cognitive deficit is associated with multiple sclerosis.

Embodiment IX

The method of Embodiment 1, wherein the at least one glutamine antagonist is a glutamine analog.

Embodiment X

The method of Embodiment 1, wherein the at least one glutamine antagonist is:
(i) a glutamine analog;
(ii) a glutamine analog selected from the group consisting of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV);
(iii) a prodrug of a glutamine analog; or
(iv) a prodrug of acivicin, azaserine, DON, and L-DONV.

Embodiment XI

A pharmaceutical composition comprising at least one glutamine antagonist, or a prodrug or analog thereof, in an amount effective to treat a cognitive deficit, and a pharmaceutically acceptable carrier, diluent, or excipient.

Embodiment XII

The method of Embodiment 11, wherein the cognitive deficit is characterized by impairment of the mental processes of perception, learning, memory, judgment, and/or reasoning.

Embodiment XIII

The method of Embodiment 11, wherein the cognitive deficit is due to a viral infection.

Embodiment XIV

The method of Embodiment 13, wherein the cognitive deficit is due to the human immunodeficiency virus (HIV).

Embodiment XV

The method of Embodiment 14, wherein the virus is latent.

Embodiment XVI

The method of Embodiment 11, wherein the cognitive deficit is selected from the group consisting of asymptomatic neurocognitive impairment (ANI), mild neurocognitive disorder (MND), and HIV-associated dementia (HAD).

Embodiment XVII

The method of Embodiment 11, wherein the cognitive deficit is associated with a neurodegenerative disorder and/or psychiatric disorder.

Embodiment XVIII

The method of Embodiment 11, wherein the cognitive deficit is associated with multiple sclerosis.

Embodiment XIX

The method of Embodiment 11, wherein the at least one glutamine antagonist is a glutamine analog.

Embodiment XX

The method of Embodiment 11, wherein the at least one glutamine antagonist is:
(i) a glutamine analog;
(ii) a glutamine analog selected from the group consisting of acivicin (L-(alpha S, 5S)-alpha-amino-3-chloro-4,5-dihydro-5-isoxazoleacetic acid), azaserine, 6-diazo-5-oxo-norleucine (DON), and 5-diazo-4-oxo-L-norvaline (L-DONV);
(iii) a prodrug of a glutamine analog; or
(iv) a prodrug of acivicin, azaserine, DON, and L-DONV As used herein, the term "glutamine antagonist" refers to an agent that blocks or interferes with the synthesis or use of glutamine in a cell, and preferably in a cell that is part of a living organism. When it is said that the glutamine antagonist interferes with the synthesis of glutamine, it is meant that the antagonist acts to reduce the amount or rate of glutamine synthesis to less than the amount or rate that would be experienced in the absence of the glutamine antagonist. When it is said that the glutamine antagonist interferes with the use of glutamine, it is meant that the antagonist acts to inhibit or block a metabolic pathway downstream of glutamine, that is, a pathway in which glutamine acts as a precursor of one or more non-glutamine compounds, or that the antagonist acts to deplete glutamine in a cell or an organism by reacting the glutamine to form a non-glutamine product, or by reversibly or irreversibly binding with glutamine to reduce its availability.

In some embodiments, a glutamine antagonist is a compound that inhibits the synthesis of glutamine. Examples of compounds having this activity include inhibitors of glutamine synthase (EC 6.3.1.2), such as L-methionine-DL-sulfoximine, and phosphinothricin; inhibitors of glutamate synthase (EC 1.4.1.13); inhibitors of amidophosphoribosyltransferase (EC 2.4.2.14); and inhibitors of glutamate dehydrogenase; and mixtures of any two or more of these.

In some embodiments, a glutamine antagonist is a glutamine depleting enzyme. Examples of such enzymes include carbamoyl-phosphate synthase (EC 6.3.5.5), glutamine-pyruvate transaminase (EC 2.6.1.15), glutamine-tRNA ligase (EC 6.1.1.18), glutaminase (EC 3.5.1.2), D-glutaminase (EC 3.5.1.35), glutamine N-acyltransferase (EC2.3.1.68), glutaminase-asparaginase (in particular glutaminase-asparaginase of *Pseudomonas* 7a and *Acinatobacter* sp.), and mixtures of any two or more of these.

In some embodiments, a glutamine antagonist is a compound that reacts with glutamine under intracellular conditions to form a non-glutamine product. An example of a compound having this property is phenylbutyrate (see Darmaun et al., Phenylbutyrate-induce glutamine depletion in humans: effect on leucine metabolism, pp. E801-E807, in Glutamine Depletion and Protein Catabolism, Am. Physiol. Soc. (1998)). Another example of a glutamine antagonist having this characteristic is phenylacetate (see, U.S. Pat. No. 6,362,226), which is incorporated herein by reference in its entirety.

In some embodiments, a glutamine antagonist is a compound that inhibits glutamine uptake by cells. Examples of compounds having this property include alpha-methylaminoisobutyric acid (inhibits GynT plasma membrane glutamine transporter; see, Varoqui et al., *J. Biol. Chem.*, 275(6): 4049-4054 (2000), wortmannin, and LY-294002 (inhibits hepatic glutamine transporter; see, Pawlik et al., *Am. J. Physiol. Gastrointest. Liver Physiol.*, 278:G532-G541 (2000)).

In some embodiments, a glutamine antagonist is a glutamine binding compound that reduces the biological availability of glutamine.

In some embodiments, a glutamine antagonist is a glutamine analog that interferes with a glutamine metabolic pathway. Examples of compounds that can act in this manner include acivicin (L-(alpha S,5S)-alpha-amino-3-chloro-4,5-dihydro-5-isoxazoleacetic acid), DON (6-diazo-5-oxo-L-norleucine), azaserine, azotomycin, chloroketone (L-2-amino-4-oxo-5-chloropentanoic acid), $N^3$-(4-methoxyfumaroyl)-L-2,3-diaminopropanoic acid (FMDP) (inactivates glucosamine-6-phosphate synthase (EC 2.6.1.16), see, Zgòdka et al., *Microbiology.* 147:1955-1959 (2001)), (3S,4R)-3,4-dimethyl-L-glutamine, (3S,4R)-3,4-dimethyl-L-pyroglutamic acid (see, Acevedo et al., *Tetrahedron.*, 57:6353-6359 (2001)), 1,5-N,N'-disubstituted-2-(substituted benzenesulphonyl) glutamamides (see, Srikanth et al., *Bioorganic and Medicinal Chemistry.* (2002)), or a mixture of any two or more of these. In some embodiments, at least one glutamine antagonist is a glutamine analog. In some embodiments, at least one glutamine antagonist is selected from the group consisting of acivicin (L-(alpha S, 5S)-alpha-amino-3-chloro-4,5-dihydro-5-isoxazoleacetic acid), azaserine, and 6-diazo-5-oxo-norleucine (DON).

In some embodiments, at least one glutamine antagonist is a prodrug of a glutamine analog. In some embodiments, at least one glutamine antagonist is a prodrug of acivicin (L-(alpha S, 5S)-alpha-amino-3-chloro-4,5-dihydro-5-isoxazoleacetic acid), azaserine, and 6-diazo-5-oxo-norleucine (DON).

In some aspects, a prodrug of a glutamine antagonist, or a pharmaceutically acceptable salt or ester thereof has a structure of formula (I):

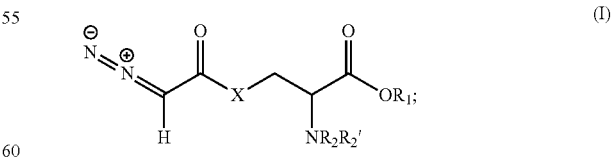

wherein: X is selected from the group consisting of a bond, —O—, and —(CH$_2$)$_n$—, wherein n is an integer selected from the group consisting of 1, 2, 3, 4, 5, 6, 7, and 8; R$_1$ is selected from the group consisting of H and a first prodrug-forming moiety capable of forming a salt or an ester; and R$_2$ is H or a second prodrug-forming moiety capable of forming an amide linkage, a carbamate linkage, a phosphoramidate linkage or a phosphorodiamidate linkage with the nitrogen adjacent to $R_2$; $R_2'$ is selected from the group consisting of H, $C_1$-$C_6$ alkyl, substituted $C_1$-$C_6$ alkyl, or $R_2$ and $R_2'$ together form a ring structure comprising —C(=O)-G-C (=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or $R_1$ and $R_2'$ together form a 4- to 6-membered heterocylic ring comprising the oxygen atom adjacent to $R_1$ and the nitrogen atom adjacent to $R_2'$; provided that the compound has at least one prodrug-forming moiety selected from the group consisting of the first and the second prodrug-forming moieties.

As used herein, the term "amide linkage" comprises a structure represented by the formula:

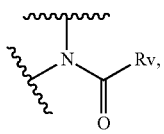

wherein $R_v$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "carbamate linkage" comprises a structure represented by the formula:

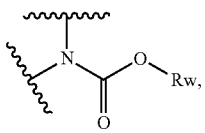

wherein $R_w$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphoramidate linkage" comprises a structure represented by the formula:

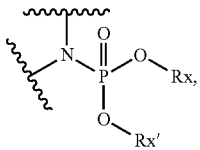

wherein $R_x$ and $R_x'$ are each independently selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphorodiamidate linkage" comprises a structure represented by the formula:

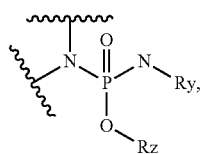

wherein $R_y$ and $R_z$ are each independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, —$(CR_3R_4)_m$-Q-Z, aryl, substituted aryl, alkylamine, substituted alkylamine, heteroaryl, substituted heteroaryl, and

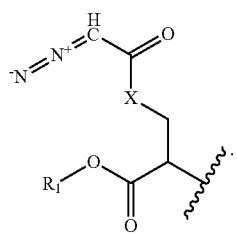

In some embodiments, X is —$CH_2$—, and n is 1.

In other embodiments, X is —O—. In some embodiments, the prodrug compound has both the first prodrug-forming moiety and the second prodrug-forming moiety. In some embodiments, the glutamine analog is a glutamine antagonist, i.e., the prodrug is a prodrug of a glutamine analog that antagonizes a glutamine pathway. Exemplary glutamine antagonists include, without limitation, 6-diazo-5-oxo-norleucine (DON), and aza-serine, and 5-diazo-4-oxo-L-norvaline (L-DONV).

In some embodiments, the presently disclosed subject matter provides a prodrug of DON. In some embodiments, the prodrug of DON has a structure of formula (I). In some embodiments, the presently disclosed subject matter provides a prodrug of L-DONV. In some embodiments, the prodrug of L-DONV has a structure of formula (I). In some embodiments, the presently disclosed subject matter provides a prodrug of azaserine. In some embodiments, the prodrug of azaserine has a structure of formula (I).

In some embodiments, $R_1$ of formula (I) comprises a residue $PRO_1$ of the prodrug-forming moiety, which, together with a basic moiety and the terminal hydroxyl group forms a salt.

In some embodiments, $R_1$ of formula (I) comprises a residue $PRO_1$ of the prodrug-forming moiety, which, together with an alkyl group and the oxygen of an adjoining hydroxyl group forms an ester.

In some embodiments, $R_1$ of formula (I) comprises a residue $PRO_1$ of the prodrug-forming moiety, which, together with an alkyl group and the nitrogen adjoining the $R_2'$ group, forms an azlactone or an oxazolidone.

In some embodiments, $R_1$ of formula (I) is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium. Preferred alkyl group, cycloalkyl group, alkenyl group, alkynyl group, and cycloalkenyl group substituents include alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

In some embodiments, $R_1$ of formula (I) is not H. In some embodiments, $R_1$ of formula (I) is not H when $R_2$ and $R_2'$ are H. In some embodiments, $R_2$ and $R_2'$ of formula (I) are each H when and $R_1$ is not H.

In some embodiments, $R_1$ of formula (I) is selected from the group consisting of a $C_{1-6}$ straight-chain alkyl, a substituted $C_{1-6}$ straight-chain alkyl, a $C_{1-6}$ branched alkyl, a substituted $C_{1-6}$ branched alkyl, tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium.

In some embodiments, $R_1$ of formula (I) is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In some embodiments, $R_1$ of formula (I) is methyl. In some embodiments, $R_1$ of formula (I) is ethyl. In some embodiments, $R_1$ of formula (I) is isopropyl.

In some embodiments, $R_2$ of formula (I) comprises a residue $PRO_2$ of the second prodrug-forming moiety, which, together with a carbonyl, oxy carbonyl, or phosphonyl group and the nitrogen of the adjoining NH, forms an amide, a carbamate, phosphoramidate, or phosphorodiamidate linkage.

In some embodiments, $R_2$ of formula (I) comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

In some embodiments, $R_2$ of formula (I) is selected from the group consisting of H, alkyl, —C(=O)—Ar, —C(=O)—Y—$(CR_3R_4)_m$—Ar, —C(=O)—Y—$(CR_3R_4)_m$—$NR_5R_6$, —P(=O)$OR_7)_n(NHR_9)_o$, —C(=O)—Y—$(CR_3R_4)_m$—Ar—O—C(=O)—$R_8$, —C(=O)—Y—$(CR_3R_4)_m$—Ar—O—$R_8$, —C(=O)—O—$(CR_3R_4)_m$—O—C(=O)—$R_{10}$, —C(=O)—O—$R_9$, —C(=O)—Y—$(CR_3R_4)_m$—Ar—O—C(=O)—Ar, and —C(=O)—Y—$(CR_3R_4)_m$—Ar—$NR_5R_6$; wherein: Y is —O— or a bond; m is an integer selected from the group consisting of 1, 2, 3, 4, 5, 6, 7, and 8; each n and o is an integer from 0 to 2 provided that the sum of n and o is 2; $R_3$ and $R_4$ is independently H, $C_1$-$C_6$ alkyl or substituted $C_1$-$C_6$ alkyl, aryl or substituted aryl, —$(CR_3R_4)_m$—$NR_5R_6$, or

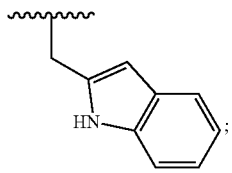 [SMILES: *Cc1cc2ccccc2[nH]1]

each $R_5$ and $R_6$ is independently H, alkyl, —C(=O)—$(CR_3R_4)_m$, —C(=O)—$(NR_5R_6)$H, or —C(=O)—$(CR_3R_4)_m$—$NR_5R_6$; each $R_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, —$(CR_3R_4)_m$-Q-Z, wherein Q is a monosaccharide, aryl, substituted aryl, heteroaryl, substituted heteroaryl, and wherein Z is

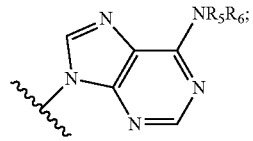

or wherein $R_7$ together with the oxygen atom to which it is attached forms a purine or pyrimidine nucleoside; each $R_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —$(CR_3R_4)_m$—Z, aryl, substituted aryl, heteroaryl, substituted heteroaryl, and

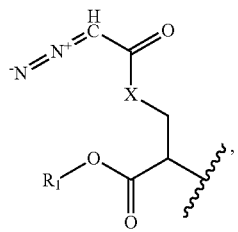

wherein $R_1$ and X are as defined above, provided that $R_1$ is not H;

each $R_8$ is independently alkyl, substituted alkyl, cycloalkyl, substituted cycloalkyl, monosaccharide, acylated monosaccharide, aryl, substituted aryl, heteroaryl, substituted heteroaryl; each $R_{10}$ is independently alkyl, substituted alkyl, cycloalkyl, substituted cycloalkyl, monosaccharide, acylated monosaccharide, aryl, substituted aryl, heteroaryl, substituted heteroaryl; and Ar is aryl, substituted aryl, heteroaryl, or substituted heteroaryl. It should be appreciated that in addition to substitutions on the amino group of Z, one or more substitutions $R_3$, $R_4$, $R_5$, and/or $R_6$ can be made to the 5 or 6 membered rings of Z.

Structures of representative DON prodrugs are provided in Table 1.

TABLE 1

Structures of Representative DON Prodrugs

| IOCB No./ Compound No. | Structure | MW |
|---|---|---|
| Compound 1 (DON) | 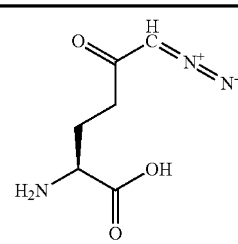 | 171.15

TABLE 1-continued

Structures of Representative DON Prodrugs

| IOCB No./Compound No. | Structure | MW |
|---|---|---|
| Compound 3 | 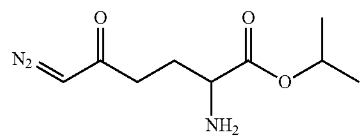 | 213.24 |
| Compound 4 | 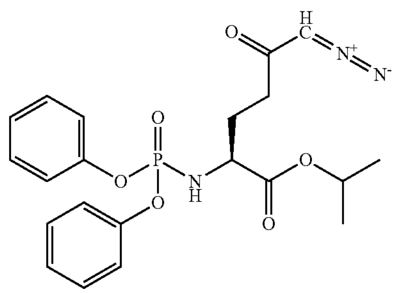 [SMILES: CC(C)OC(=O)[C@H](CCC(=O)C=[N+]=[N-])NP(=O)(Oc1ccccc1)Oc1ccccc1] | 445.41 |
| Compound 6 | 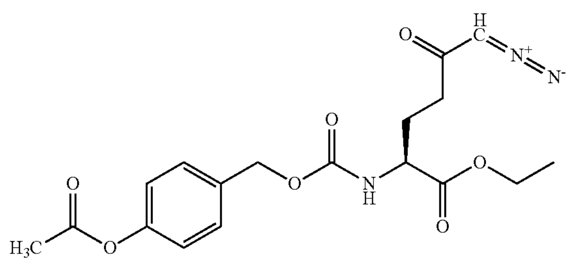 [SMILES: CCOC(=O)[C@H](CCC(=O)C=[N+]=[N-])NC(=O)OCc1ccc(OC(C)=O)cc1] | 391.38 |
| Compound 7 | 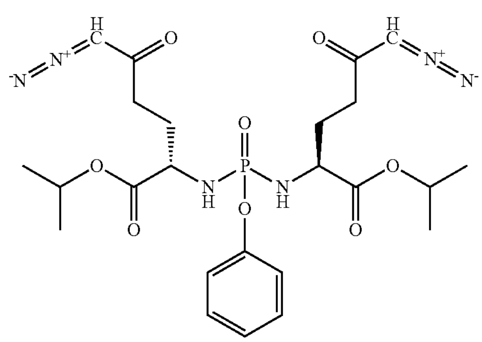 | 564.53 |
| Compound 9 | 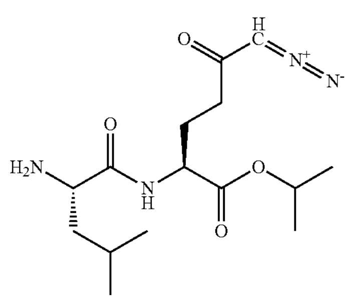 [SMILES: CC(C)C[C@H](N)C(=O)N[C@@H](CCC(=O)C=[N+]=[N-])C(=O)OC(C)C] | 326.39 |

TABLE 1-continued

Structures of Representative DON Prodrugs

| IOCB No./Compound No. | Structure | MW |
|---|---|---|
| Compound 11 | 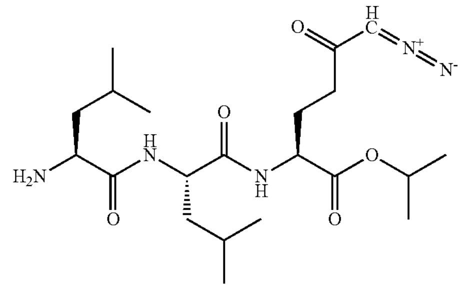 [SMILES: CC(C)C[C@H](NC(=O)[C@@H](N)CC(C)C)C(=O)N[C@@H](CCC(=O)C=[N+]=[N-])C(=O)OC(C)C] | 439.55 |
| Compound 13 | 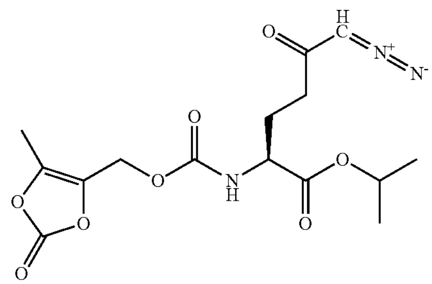 [SMILES: Cc1oc(=O)oc1COC(=O)N[C@@H](CCC(=O)C=[N+]=[N-])C(=O)OC(C)C] | 369.18 |
| Compound 14a # | 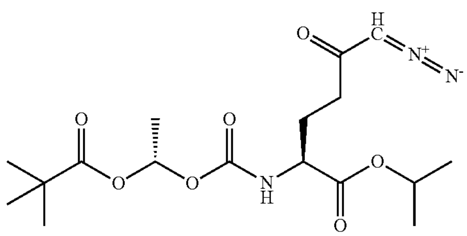 [SMILES: CC(C)OC(=O)[C@H](CCC(=O)C=[N+]=[N-])NC(=O)O[C@@H](C)OC(=O)C(C)(C)C] | 385.41 |
| Compound 14b # | 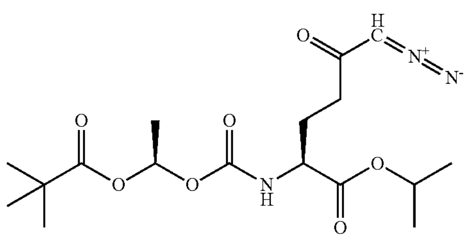 [SMILES: CC(C)OC(=O)[C@H](CCC(=O)C=[N+]=[N-])NC(=O)O[C@H](C)OC(=O)C(C)(C)C] | 385.41 |
| Compound 15 | 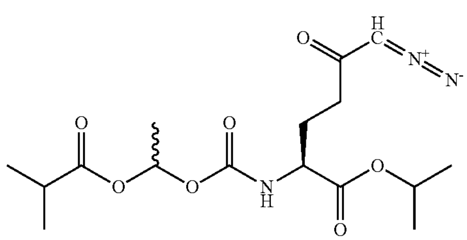 [SMILES: CC(C)OC(=O)[C@H](CCC(=O)C=[N+]=[N-])NC(=O)OC(C)OC(=O)C(C)C] | 371.39 |
| Compound 17 | 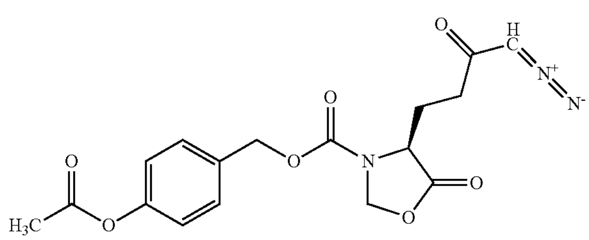 [SMILES: CC(=O)Oc1ccc(COC(=O)N2COC(=O)[C@@H]2CCC(=O)C=[N+]=[N-])cc1] | 375.33 |

TABLE 1-continued
Structures of Representative DON Prodrugs
| IOCB No./ Compound No. | Structure | MW |
|---|---|---|
| Compound 20 | 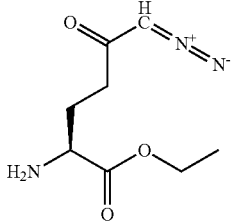 | 199.21 |
| Compound 22 | 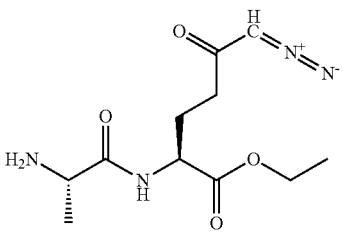 [SMILES: CCOC(=O)[C@H](CCC(=O)C=[N+]=[N-])NC(=O)[C@H](C)N] | 270.28 |
| Compound 23 | 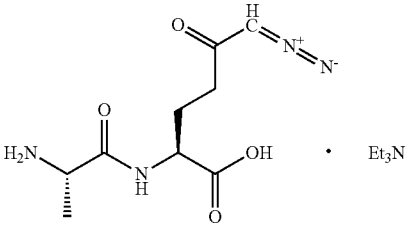 [SMILES: "Et3N" ; C[C@H](N)C(=O)N[C@@H](CCC(=O)C=[N+]=[N-])C(=O)O ; "·"] | 343.42 |
| Compound 25 | 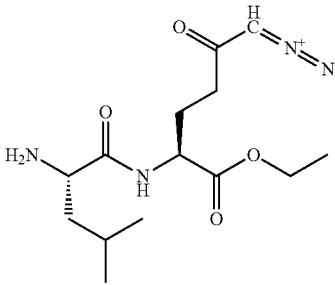 | 312.36 |
| Compound 26 | 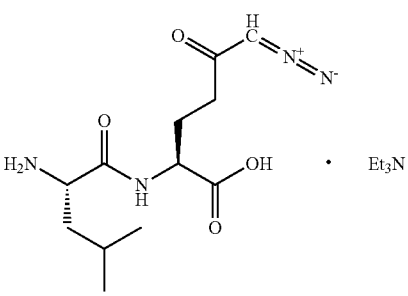 [SMILES: "Et3N" ; CC(C)C[C@H](N)C(=O)N[C@@H](CCC(=O)C=[N+]=[N-])C(=O)O ; "·"] | 385.50 |

TABLE 1-continued

Structures of Representative DON Prodrugs

| IOCB No./ Compound No. | Structure | MW |
|---|---|---|
| Compound 28 | 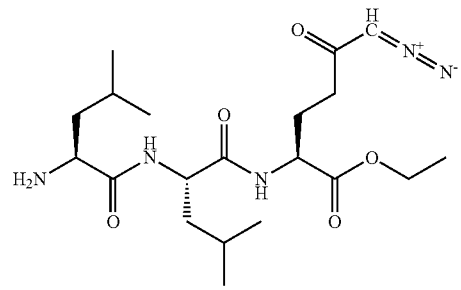 [SMILES: CCOC(=O)[C@H](CCC(=O)C=[N+]=[N-])NC(=O)[C@H](CC(C)C)NC(=O)[C@@H](N)CC(C)C] | 425.52 |
| Compound 29 | 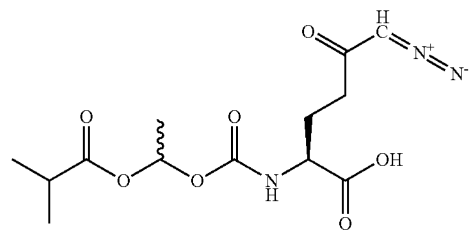 [SMILES: CC(OC(=O)N[C@@H](CCC(=O)C=[N+]=[N-])C(=O)O)OC(=O)C(C)C] | 329.31 |
| Compound 30 | 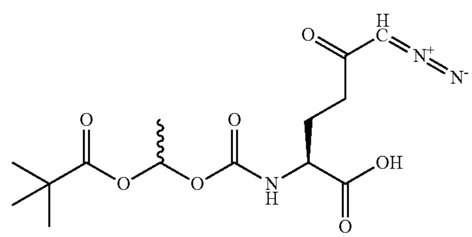 [SMILES: CC(OC(=O)N[C@@H](CCC(=O)C=[N+]=[N-])C(=O)O)OC(=O)C(C)(C)C] | 343.33 |
| Compound 31 | 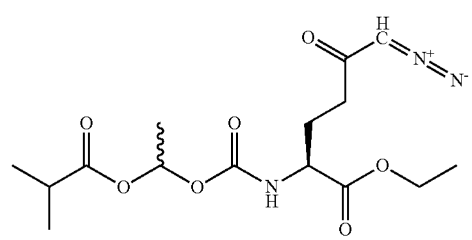 [SMILES: CCOC(=O)[C@H](CCC(=O)C=[N+]=[N-])NC(=O)OC(C)OC(=O)C(C)C] | 357.37 |
| Compound 32 | 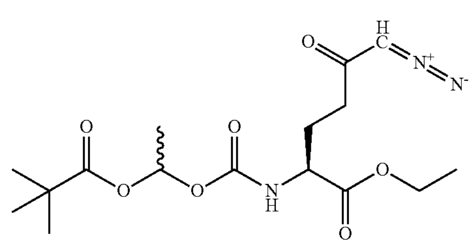 [SMILES: CCOC(=O)[C@H](CCC(=O)C=[N+]=[N-])NC(=O)OC(C)OC(=O)C(C)(C)C] | 371.39 |

TABLE 1-continued

Structures of Representative DON Prodrugs

| IOCB No./Compound No. | Structure | MW |
|---|---|---|
| Compound 34 | (structure) | 385.42 |
| Compound 35 | (structure) | 327.25 |
| Compound 36 | (structure) | 355.30 |
| Compound 38a | (structure) | 399.45 |

TABLE 1-continued

Structures of Representative DON Prodrugs

| IOCB No./ Compound No. | Structure | MW |
|---|---|---|
| Compound 38 | 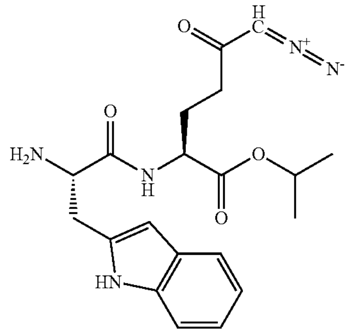 [SMILES: CC(C)OC(=O)[C@H](CCC(=O)C=[N+]=[N-])NC(=O)[C@@H](N)Cc1cc2ccccc2[nH]1] | 399.45 |
| Compound 40 | 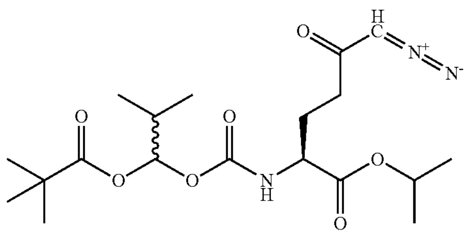 [SMILES: CC(C)OC(=O)[C@H](CCC(=O)C=[N+]=[N-])NC(=O)OC(OC(=O)C(C)(C)C)C(C)C] | 413.47 |
| Compound 42 | 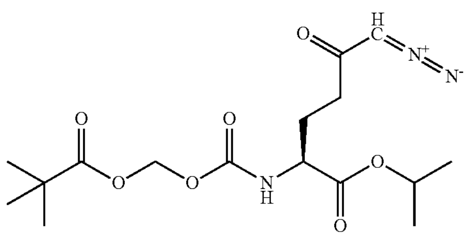 [SMILES: CC(C)OC(=O)[C@H](CCC(=O)C=[N+]=[N-])NC(=O)OCOC(=O)C(C)(C)C] | 371.39 |
| Compound 44 | 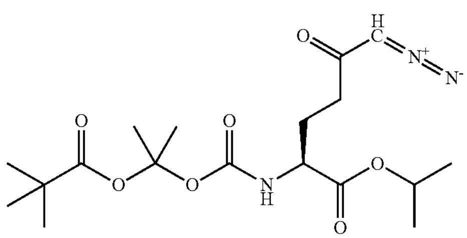 [SMILES: CC(C)OC(=O)[C@H](CCC(=O)C=[N+]=[N-])NC(=O)OC(C)(C)OC(=O)C(C)(C)C] | 2.44 |
| Compound 47 | 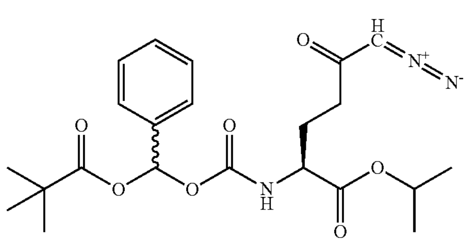 [SMILES: CC(C)OC(=O)[C@H](CCC(=O)C=[N+]=[N-])NC(=O)OC(OC(=O)C(C)(C)C)c1ccccc1] | 447.49 |
| Compound 49 | 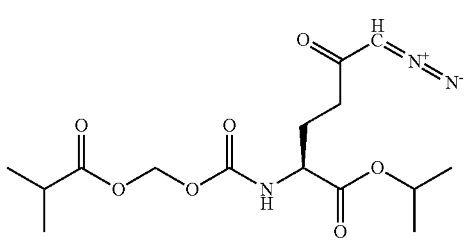 [SMILES: CC(C)OC(=O)[C@H](CCC(=O)C=[N+]=[N-])NC(=O)OCOC(=O)C(C)C] | 357.36 |

TABLE 1-continued

Structures of Representative DON Prodrugs

| IOCB No./Compound No. | Structure | MW |
|---|---|---|
| Compound 51 | 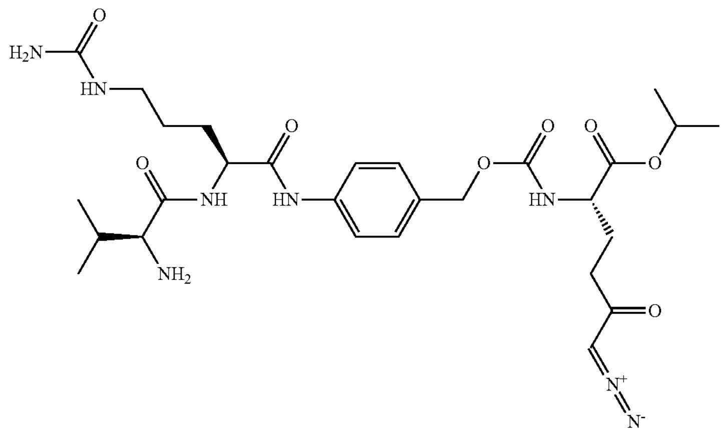 [SMILES: CC(C)OC(=O)[C@H](CCC(=O)C=[N+]=[N-])NC(=O)OCc1ccc(NC(=O)[C@H](CCCNC(N)=O)NC(=O)[C@@H](N)C(C)C)cc1] | 618.69 |
| Compound 52 | 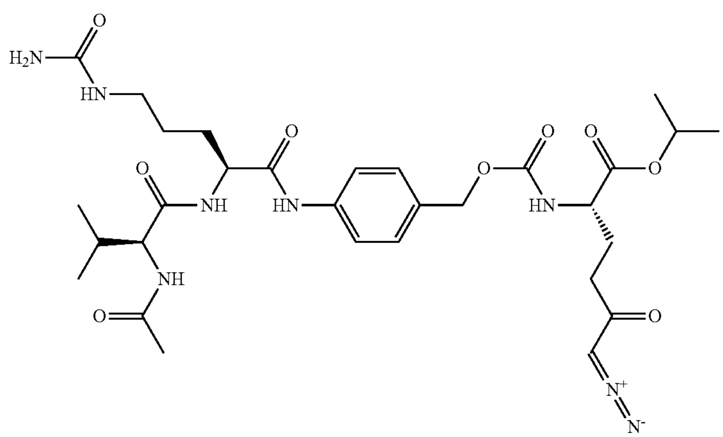 [SMILES: CC(=O)N[C@H](C(=O)N[C@@H](CCCNC(N)=O)C(=O)Nc1ccc(COC(=O)N[C@@H](CCC(=O)C=[N+]=[N-])C(=O)OC(C)C)cc1)C(C)C] | 660.73 |
| Compound 56 | 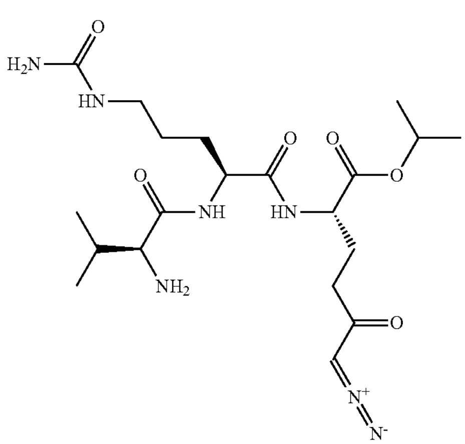 [SMILES: CC(C)OC(=O)[C@H](CCC(=O)C=[N+]=[N-])NC(=O)[C@H](CCCNC(N)=O)NC(=O)[C@@H](N)C(C)C] | 469.54 |

TABLE 1-continued

Structures of Representative DON Prodrugs

| IOCB No./Compound No. | Structure | MW |
|---|---|---|
| Compound 57 | 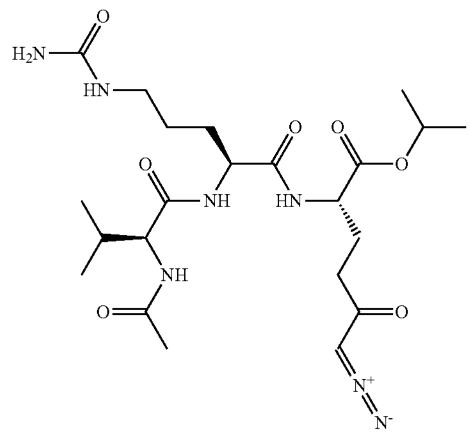 [SMILES: CC(=O)N[C@H](C(=O)N[C@@H](CCCNC(N)=O)C(=O)N[C@@H](CCC(=O)C=[N+]=[N-])C(=O)OC(C)C)C(C)C] | 511.58 |
| Compound 59 | 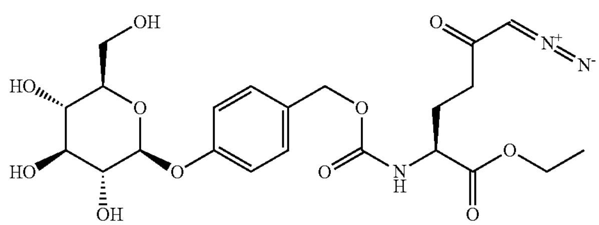 [SMILES: CCOC(=O)[C@H](CCC(=O)C=[N+]=[N-])NC(=O)OCc1ccc(O[C@@H]2O[C@H](CO)[C@@H](O)[C@H](O)[C@H]2O)cc1] | 511.48 |
| Compound 60a | 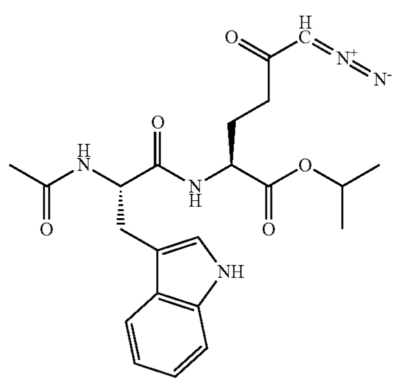 [SMILES: CC(=O)N[C@@H](Cc1c[nH]c2ccccc12)C(=O)N[C@@H](CCC(=O)C=[N+]=[N-])C(=O)OC(C)C] | 464.19 |
| Compound 60 | 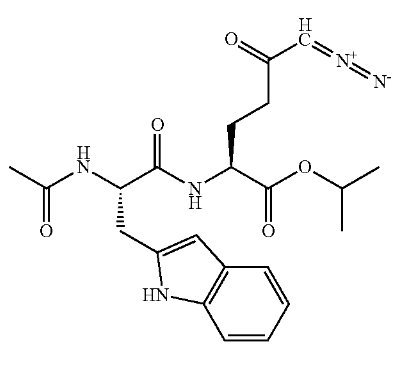 [SMILES: CC(=O)N[C@@H](Cc1cc2ccccc2[nH]1)C(=O)N[C@@H](CCC(=O)C=[N+]=[N-])C(=O)OC(C)C] | 464.19 |

TABLE 1-continued

Structures of Representative DON Prodrugs

| IOCB No./Compound No. | Structure | MW |
|---|---|---|
| A | 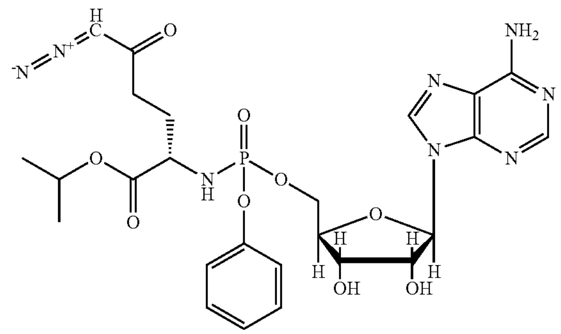 | 618.54 |
| B | 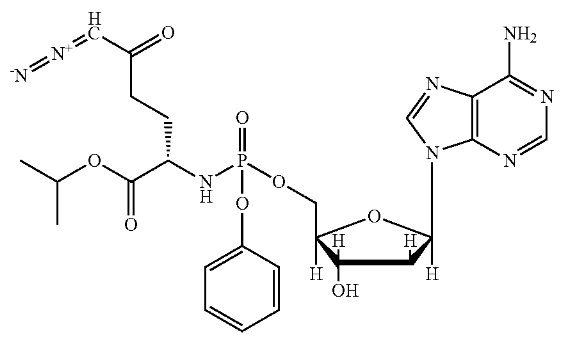 | 602.54 |
| C | 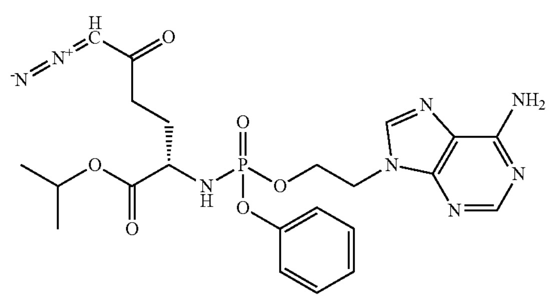 | 530.47 |
| D | 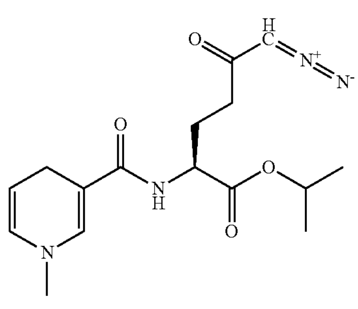 [SMILES: CC(C)OC(=O)[C@H](CCC(=O)C=[N+]=[N-])NC(=O)C1=CN(C)C=CC1] | 334.38 |

TABLE 1-continued

Structures of Representative DON Prodrugs

| IOCB No./ Compound No. | Structure | MW |
|---|---|---|
| E | 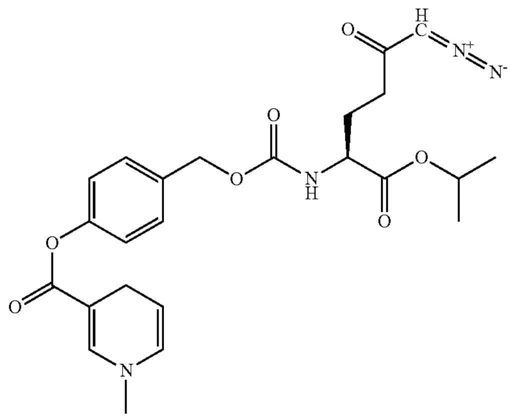 [SMILES: CC(C)OC(=O)[C@H](CCC(=O)C=[N+]=[N-])NC(=O)OCc1ccc(OC(=O)C2=CN(C)C=CC2)cc1] | 484.51 |
| F | 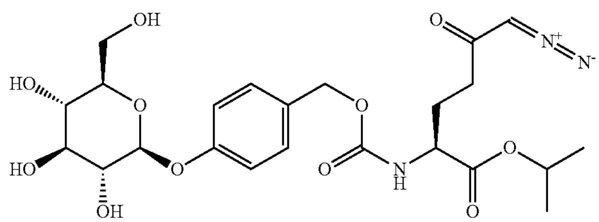 [SMILES: CC(C)OC(=O)[C@H](CCC(=O)C=[N+]=[N-])NC(=O)OCc1ccc(O[C@@H]2O[C@H](CO)[C@@H](O)[C@H](O)[C@H]2O)cc1] | 525.51 |
| G | 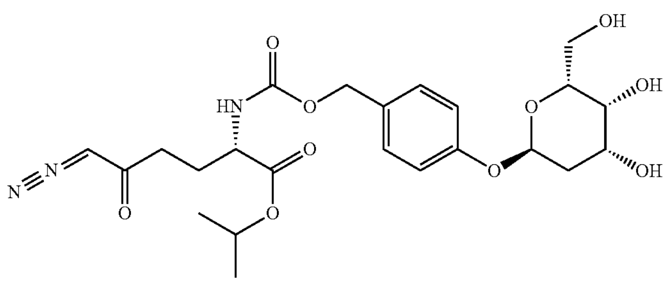 [SMILES: CC(C)OC(=O)[C@H](CCC(=O)C=[N+]=[N-])NC(=O)OCc1ccc(O[C@@H]2C[C@@H](O)[C@@H](O)[C@@H](CO)O2)cc1] | 509.51 |
| LTP 073 | 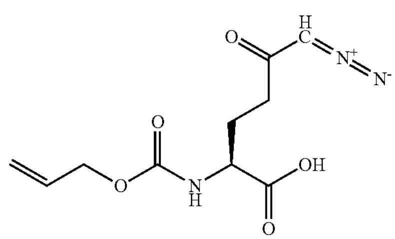 [SMILES: C=CCOC(=O)N[C@@H](CCC(=O)C=[N+]=[N-])C(=O)O] | 255.23 |
| JAM0351 | 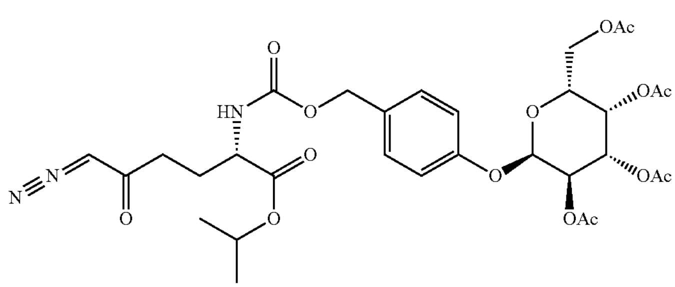 [SMILES: CC(=O)OC[C@H]1O[C@H](Oc2ccc(COC(=O)N[C@@H](CCC(=O)C=[N+]=[N-])C(=O)OC(C)C)cc2)[C@H](OC(C)=O)[C@@H](OC(C)=O)[C@H]1OC(C)=O] | 693.66 |

TABLE 1-continued

Structures of Representative DON Prodrugs

| IOCB No./ Compound No. | Structure | MW |
|---|---|---|
| JAM0359 | 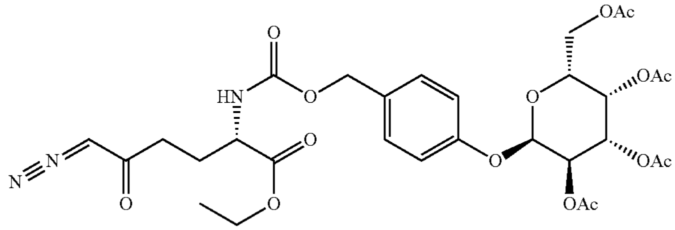 [SMILES: CCOC(=O)[C@H](CCC(=O)C=[N+]=[N-])NC(=O)OCc1ccc(O[C@H]2O[C@H](COC(C)=O)[C@H](OC(C)=O)[C@H](OC(C)=O)[C@H]2OC(C)=O)cc1] | 679.63 |

A diastereomeric mixture of isopropyl (2S)-6-diazo-5-oxo-2-(((1-(pivaloyloxy)ethoxy)carbonyl)amino)hexanoate was prepared and separated by column chromatography to give isopropyl (S)-6-diazo-5-oxo-2-((((S)-1-(pivaloyloxy)ethoxy)carbonyl)amino)hexanoate and isopropyl (S)-6-diazo-5-oxo-2-((((R)-1-(pivaloyloxy)ethoxy)carbonyl)amino)hexanoate. The S,S-isomer was arbitrarily designated compound 14a, and the S,R-isomer was arbitrarily designated compound 14b. The actual stereochemistry of the acetal methyl group was not determined. The diastereoisomer that was arbitrarily designated compound 14b was used in the biological studies described herein. See PCT/US2016/044767 (WO 2017/023774 A1), which is fully incorporated by reference herein.

As described herein, compound 14b demonstrated unexpected stability in human and monkey plasma and achieved an unexpected enhanced CSF/plasma ratio versus DON in monkeys (10 fold). In addition, compound 47 achieved an unexpected enhanced CSF/plasma ratio versus DON in swine (15 fold). Thus, these compounds are uniquely useful for the treatment of cognitive deficits that require enhanced levels of DON in the brain.

In general, the presently disclosed methods result in a decrease in the severity of a condition, disease, or disorder (e.g., a cognitive deficit) in a subject. The term "decrease" is meant to inhibit, suppress, attenuate, diminish, arrest, or stabilize a symptom of the condition, disease, or disorder. As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

The terms "subject" and "patient" are used interchangeably herein. The subject treated by the presently disclosed methods, uses, glutamine antagonists and compositions comprising those glutamine antagonists in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

The terms "decrease," "reduced," "reduction," "decrease," or "inhibit" are all used herein generally to mean a decrease by a statistically significant amount. However, for avoidance of doubt, "reduced," "reduction," "decrease," or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

The terms "increased," "increase," "enhance," or "activate" are all used herein to generally mean an increase by a statically significant amount; for the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Generally, at least one glutamine antagonist described herein can be used in combination with an additional therapeutic agent (e.g., a pharmaceutically active agent, e.g., a drug approved by a regulatory agency). The therapeutic agent may act synergistically with the glutamine antagonist described herein, or they may independently exert their intended effects. The disclosure contemplates any therapeutic agent which a skilled artisan would use in connection with a method, use, or composition described herein. Examples of therapeutic agents contemplated for use in the presently disclosed methods, uses and compositions in combination with the glutamine antagonists include, but are not limited to, antiviral agents, immunotherapeutic agents, anti-inflammatory agents, neuroprotective agents, neuroregenerative agents, neurotrophic factors, stem and progenitor cells used to replace and/or repair endogenous populations of abnormal, harmful, or unhealthy cells, and vaccines.

Exemplary classes of antiviral agents of use herein include, without limitation, antiviral boosters, antiviral combinations, antiviral interferons, chemokine receptor antagonists, integrase strand transfer inhibitors, NNRTIs, NS5A inhibitors, nucleoside reverse transcriptase inhibitors (NRTIs), protease inhibitors, and purine nucleosides.

Examples of antirival boosters of use herein include, without limitation, ritonavir, cobicistat, and combinations thereof.

Examples of antiviral combinations of use herein include, without limitation, abacavir and lamivudine (EPZICOM), cobicistat/elvitegravir/emtricitabine/tenofovir (STRIBILD), emtricitabine/tenofovir (TRUVADA), efavirenz/emtricitabine/tenofovir (ATRIPLA), ledipasvir/sofosbuvir (HARVONI), abacavir/lamivudine/zidovudine (TRIZIVIR), emtricitabine/rilpivirine/tenofovir (COMPLERA), abacavir/dolutegravir/lamivudine (TRIUMEQ), dasabuvir/ombitasvir/paritaprevir/ritonavir (VIEKIRA PAK), elbasvir/grazoprevir (ZEPATIER), lamivudine/zidovudine (COMBIVIR), cobicistat/elvitegravir/emtricitabine/tenofovir alafenamide (GENVOYA), cobicistat/darunavir (PREZCOBIX), emtricitabine/tenofovir, emtricitabine/lopinavir/ritonavir/tenofovir, emtricitabine/nelfinavir/tenofovir, lamivudine/raltegravir (DUTREBIS), atazanavir/cobicistat (EVOTAZ), interferon alfa-2b/ribavirin (REBETRON), ombitasvir/paritaprevir/ritonavir (TECHNIVIE), and combinations thereof.

Examples of antiviral interferons of use herein include, without limitation, peginterferon alfa-2a (PEGASYS), peginterferon alfa-2b (PEGINTRON), peginterferon alfa-2b (SYLATRON), and combinations thereof.

An exemplary chemokine receptor antagonist of use herein is maraviroc (SELZENTRY).

Exemplary integrase strand transfer inhibitors of use herein include, without limitation, raltegravir, dolutegravir, elvitegravir, and combinations thereof.

Exemplary non-nucleoside reverse transcriptase inhibitors (NNRTIs) of use herein include, without limitation, nevirapine, etravirine, efavirenz, rilpivirine, delavirdine, nevirapine and combinations thereof.

An exemplary non-structural protein 5A (NS5A) inhibitor of use herein is daclatasvir (DAKLINZA).

Exemplary nucleoside reverse transcriptase inhibitors (NRTIs) of use herein include, without limitation, entecavir, lamivudine, adefovir, didanosine, tenofovir, abacavir, lamivudine, zidovudine, stavudine, emtricitabine, zalcitabine, telbivudine, didanosine, and combinations thereof.

Exemplary protease inhibitors of use herein include, without limitation, boceprevir, simeprevir, telaprevir, lopinavir/ritonavir (KALETRA), fosamprenavir, darunavir, ritonavir, tipranavir, atazanavir, nelfinavir, amprenavir, indinavir, saquinavir, and combinations thereof.

Exemplary purine nucleoside of use herein include, without limitation, ribavirin, valacyclovir, famciclovir, acyclovir, ganciclovir, valganciclovir, cidofovir and combinations thereof.

Other exemplary antiviral agents of use herein include, without limitation, sofosbuvir, enfuvirtide, enfuvirtide, fomivirsen, and combinations thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with at least one glutamine antagonist described herein include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, "anti-inflammatory agent" refers to an agent that may be used to prevent or reduce an inflammatory response or inflammation in a cell, tissue, organ, or subject. Exemplary anti-inflammatory agents contemplated for use include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Exemplary neuroprotective agents include, without limitation, L-dopa, dopamine agonists (e.g., apomorphine, bromocriptine, pergolide, ropinirole, pramipexole, or cabergoline), adenosine A2a antagonists (Shah et al., Curr. Opin. Drug Discov. Devel. 13:466-80 (2010)); serotonin receptor agonists; continuous-release levodopa (Sinemet CR®, MSD, Israel); continuous duodenal levodopa administration (Duodopa®, Abbott, UK); catechol-O-methyltransferase (COMT) inhibitors (e.g., Stalevo®, Novartis Pharma, USA; entacapone (Comtan®, Novartis Pharma, USA)); tolcapone; coenzyme Q10, and/or MAO-B inhibitors (e.g., Selegiline or Rasagiline). Additional neuroprotective agents are described in, e.g., Hart et al., Mov. Disord. 24: 647-54 (2009).

In some contexts, an agent described herein can be administered with an antigen (e.g., to induce an immune response). In some embodiments, an adjuvant can be used in combination with the antigen.

An agent described herein can also be used in combination with an imaging agent. An agent (e.g., a glutamine antagonist) can be attached to imaging agents for imaging and diagnosis of various diseased organs, tissues or cell types. The agent can be labeled or conjugated a fluorophore or radiotracer for use as an imaging agent. Many appropriate imaging agents are known in the art, as are methods for their attachment to agents (e.g., attaching an imaging agent to a proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase)). An agent may also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection.

The presently disclosed subject matter contemplates the use of at least one glutamine antagonists, alone, or optionally together with one or more additional therapeutic agents described herein. Accordingly, in an aspect the presently disclosed subject matter involves the use of at least one glutamine antagonist for treating a cognitive deficit.

II. Pharmaceutical Compositions Comprising Glutamine Antagonists

The presently disclosed subject matter also contemplates pharmaceutical compositions comprising one or more glutamine antagonists for the treatment of a cognitive deficit. In some embodiments, the presently disclosed methods comprise the use of the presently disclosed glutamine antagonists for the manufacture of a medicament for the treatment of a cognitive deficit.

Accordingly, in some embodiments, the presently disclosed subject matter provides a pharmaceutical composition comprising an effective amount of at least one glutamine antagonist that treats a cognitive deficit, and a pharmaceutically acceptable carrier, diluent, or excipient.

In some embodiments, the glutamine antagonist composition comprises one or more additional therapeutic agents described herein (e.g., antiviral agents, immunotherapeutic agents, anti-inflammatory agents, neuroprotective agents, neuroregenerative agents, neurotrophic factors, stem and progenitor cells used to replace and/or repair endogenous populations of abnormal, harmful, or unhealthy cells, and vaccines). Generally, the presently disclosed compositions (e.g., comprising at least one glutamine antagonist) can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of compositions comprising at least one glutamine antagonist, such that it enters the patient's system and, thus, are subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g., by means of conventional mixing, dissolving, granulating, dragee-making, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al. (1981) *J. Biomed. Mater. Res.* 15:167; Langer (1982), Chem. Tech. 12:98), ethylene vinyl acetate (Langer et al. (1981) *J. Biomed. Mater. Res.* 15:167), or poly-D-(-)-3-hydroxybutyric acid (EP 133,988A). Sustained release compositions also include liposomally entrapped compositions comprising at least one glutamine antagonist which can be prepared by methods known in the art (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485,045 and 4,544,545; and EP 102,324A). Ordinarily, the liposomes are of the small (about 200-800 angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, pre-determined target site.

In another embodiment, the presently disclosed pharmaceutical compositions may comprise PEGylated therapeutics (e.g., PEGylated antibodies). PEGylation is a well established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents, such as toluene, methylene chloride, ethanol and acetone; (d) PEGylated antibody fragments can be concentrated to 200 mg/mL, and the ability to do so opens up formulation and dosing options, such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by sub-cutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one glutamine antagonist. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one glutamine antagonist to allow for the preparation of highly concentrated solutions.

For nasal or transmucosal administration generally, penetrants appropriate to the particular barrier to be permeated are used in the formulation. Such penetrants are generally known in the art.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms, such as described herein or by other conventional methods known to those of skill in the art.

In general, the "effective amount", "amount effective to treat" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like. Generally, the "effective amount" or "amount effective" to treat a cognitive deficit is less than the effective amount needed to treat cancer. It should be appreciated that the amount of at least one glutamine antagonist, or prodrug or analog thereof, effective to treat a cognitive deficit comprises the maximal non-toxic dose that sufficient for improving a particular cognitive deficit in a subject. In some embodiments, the effective amount of at least one glutamine antagonist, or prodrug or analog thereof, is less than 0.1 mg/kg/day.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one glutamine antagonist can be varied so long as the beneficial effects of the combination of these agents are achieved. Accordingly, the phrase "in combination with" refers to the administration of at least one glutamine antagonist, and optionally additional agents either simultaneously, sequentially, or a combination thereof. Therefore, a subject administered a combination of at least one glutamine antagonist, and optionally additional agents can receive at least one glutamine antagonist, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising at least one glutamine antagonist, and optionally additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_aQ_A+Q_bQ_B=\text{Synergy Index (SI)}$$

wherein:

$Q_A$ is the concentration of a component A, acting alone, which produced an end point in relation to component A;

Qa is the concentration of component A, in a mixture, which produced an end point;

QB is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition including at least one glutamine antagonist, and optionally additional agents, alone or in combination with one or more additional therapeutic agents in admixture with a pharmaceutically acceptable excipient.

More particularly, the presently disclosed subject matter provides a pharmaceutical composition comprising at least one glutamine antagonist, and optionally additional agents, and a pharmaceutically acceptable carrier. In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

III. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{14}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

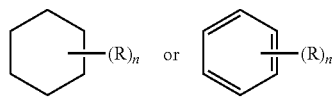

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

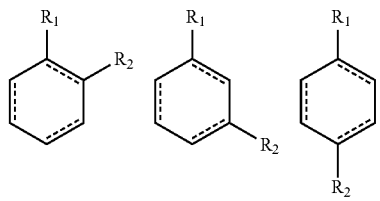

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl," and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —$CO_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_{30}$, —CH(Ph)$_2$, fluoro($C_1$-$C_4$)alkoxo, and fluoro($C_1$-$C_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxy, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms, such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Treatment of Cognitive Deficits

Materials and Methods
  Mice:
  Mice were kept in accordance with guidelines of the Johns Hopkins University Institutional Animal Care and Use Committee. Six week old male C57BL mice were used for the experiments.
  Prophylactic Treatment with DON:
  Six week old C57Bl mice were treated with DON (1 mg/kg) in 0.5 mL saline or saline alone. 24 h after first DON administration, groups of mice (n=8) were infected with EcoHIV/NDK-V5C5 ($2 \times 10^6$ pg p24/mouse) or treated with saline by intraperitoneal inoculation. A second dose of DON was administered 24 h post-infection and then treatment was continued on alternate days until the end of the experiment (including behavioral testing). Thirty days after infection, all mice were subjected to behavioral testing in a radial arm water test measuring learning and memory. Treatments given to the groups of mice were saline, saline+DON, HIV, and HIV+DON.
  Therapeutic Treatment with DON:
  The experimental design was for DON prophylaxis except that mice were infected first and DON administration at 1 mg/kg every other day started on Day 26 after infection.
  Radial Water Maze:
  A water tank (6 ft in diameter; 4 ft high) was divided into six swimming lanes using aluminum dividers. The tank was filled with water at room temperature up to the upper edges of swimming lane dividers. White washable Crayola paint for children (Hallmark) was added to make the water non-transparent. A submerged platform was placed randomly at the end of one of the lanes, where it remains throughout that particular day, but was moved to another random location on subsequent days, insuring that the mouse was using short term memory to locate the platform on that day and not recalling where the platform was on previous days. Several three dimensional visual cues were placed around the tank so the mouse could make an association between the cue and the location of the platform. The memory test was expected to last 5-6 days using male C57Bl mice and 8-12 days using male 129×1 mice; it consisted of five daily trials of 1 min; the trials started at the same time each day. Each memory test was conducted in its entirety by a single designated individual wearing consistently similar protective clothing to avoid distraction of animals. At the start of each trial, the mice were placed in the pool from a randomly chosen arm and the number of errors (entering an arm without the platform) was recorded over a 1 min period. After each error, the mouse was gently pulled back to the start arm for that trial. After each trial, if the mouse did not locate the platform, the investigator guided the mouse to the platform and allowed the mouse to rest on the platform for 20 s. After four trials, the mice were returned to their home cages for 30 min and then administered a memory retention trial. The memory retention trial started in the same arm as trial 4 (the last training trial). A baseline was considered to be established when control mice reached asymptotic performance levels, that is one error or less on trials four and five. The scores for each mouse on the last three trial days were averaged and used for statistical analysis.

Plasma Analysis:

DON was spiked into untreated mouse plasma to generate standards at concentrations from 10 nM to 100 µM at half-log intervals. Butanol with 3N HCl (250 µL) was added to standards and samples (50 µL) and centrifuged at 16,000×g for 5 minutes to precipitate proteins. An aliquot (200 µL) of the supernatant was incubated at 60° C. for 30 minutes to derivatize DON into a more stable and lipophilic analyte as previously described (Alt et al., 2015). After derivatization the samples were dried at 45° C. under a nitrogen stream. Samples were resuspended in 50 µL 70/30 water/acetonitrile, vortexed and centrifuged at 16,000×g. Samples (2 µL) were injected and separated on an Agilent 1290 equipped with a C18 column over a 5.5 minute gradient from 30-70% acetonitrile+0.1% formic acid and quantified on an Agilent 6520 QTOF mass spectrometer. Standards within the quantifiable range were used to generate a standard curve. Samples below the limit of quantification (BLQ) were assigned a value of 0.

Brain analysis: Brain sections were weighed. DON was spiked into untreated mouse brain tissue to generate standards as described above. Butanol with 3N HCl (5 µL/mg) was added to standards and samples and homogenized by pestle followed by centrifugation at 16,000×g. An aliquot (200 µL) of the supernatant was transferred to a new tube and processed as described in the plasma analysis section. Twenty microliters was injected for analysis as described hereinabove.

Glutamate CSF Levels:

CSF samples were derivatized with dabsyl chloride for analysis. To prepare a dabsyl chloride stock, acetone was added to dabsyl chloride to 10 mM concentration, vortexed, water bath sonicated for 10 minutes followed by heating to 60° C. for 10 minutes, vortexing again, centrifugation for 5 minutes at 16,000×g and taking the supernatant. Ten microliter standards of glutamate were prepared in artificial CFS by serial dilution. To each standard and sample, one volume of 0.2 M sodium bicarbonate buffer (pH 9.0 containing 100 µM glutamate-d5 as internal standard) and 2 volumes dabsyl chloride stock was added. Samples were incubated at 60° C. 10 minutes to derivatize. Samples (10 µL) were injected and separated on an Agilent 1290 equipped with a SB-AQ column over a 4 minute gradient from 20-95% acetonitrile+ 0.1% formic acid and quantified on an Agilent 6520 QTOF mass spectrometer. Glutamate was quantifiable to 10 nM.

Statistical Analysis:

Prism software version 5.0 (GraphPad Software) was used for statistical analyses, including unpaired Student's t-test, two-way analysis of variance (ANOVA) and log-rank analysis. A P value less than 0.05 was considered statistically significant.

Results

Effect of DON on HIV Infection and Neuropathogenesis in Mice:

A small animal model of HIV pathogenesis was used in which conventional immunocompetent mice are infected with chimeric HIV, EcoHIV, which carries murine leukemia virus envelope protein gp80 in place of gp120 to permit infection of mouse cells and mice (Potash-2005). HIV-infected mice seroconvert and mount protective CD8 T cell responses that limit virus replication systemically and in brain, but can transmit infectious virus (Potash et al., 2005; Kelschenbach et al., 2012; Hadas et al., 2013). Chronically infected mice carry HIV in T cells, macrophages, and microglial cells in the brain (Kelschenbach et al., 2012; He et al., 2014) and similar to many HIV infected individuals, the animals manifest cognitive disease that can be quantified by measuring animal performance in behavioral tests including water maze and fear conditioning. Two experiment formats were used to test the effect of DON on HIV infection in this system: DON prophylaxis and DON treatment.

Effect of Compound 25 on Reversing EcoHIV-Induced Increases in CSF Glutamate Concentration:

Male C57BL6 mice were sham or EcoHIV-inoculated (4e6 pg p24, i.p.) then randomized to receive vehicle or compound 25 (1.82 mg/kg, i.p. every other day) beginning 15 post-inoculation. On day 33 post-inoculation, all mice were deeply anesthetized with isoflurane 30 minutes post-last dose, and CSF was terminally sampled from the cisterna magna prior to measurement of glutamate concentrations by LC/MS-MS. EcoHIV infection caused increases in CSFS glutamate that were normalized by compound 25 treatment. Excluding values >2SD from mean, n=4-5/group. Analysis by two-way ANOVA followed by post-hoc Fisher's LSD, *p<0.05, ***p<0.001. Data are presented as the mean+ SEM.

FIG. 1A, FIG. 1B, and FIG. 1C show that prophylactic treatment of mice with DON prevents development of HIV-induced cognitive impairment.

FIG. 2A, FIG. 2B, and FIG. 2C show that DON treatment of EcoHIV-infected mice with demonstrable cognitive impairment completely abrogates (reverses) cognitive disease.

FIG. 3 shows that DON treatment reversed HIV-mediated down-modulation of STX1A and NRGN in correlation with abrogation of cognitive defect of EcoHIV-infected mice.

FIG. 4A, FIG. 4B, and FIG. 4C show that micromolar DON levels were observed in plasma, CSF and basal ganglia in mice treated in the behavioral experiments. Mouse samples were analyzed for DON using LC-MS/MS 15 minutes post administration. DON was quantifiable in all samples provided. Fifteen minutes after dosing, DON averaged around 2.5-3 µM in plasma, and 0.3-0.5 uM in brain tissue and CSF. No significant difference was observed between mice infected with PBS and EcoHIV.

FIG. 5A shows glutamate in CFS from mice treated with DON as quantified via LC/MS. There was a trend for glutamate levels to be higher in EcoHIV mice versus PBS mice. In addition, DON tended to decrease the glutamate in the EcoHIV mice; however, no significant differences were found among the treatment groups by one-way ANOVA analysis.

FIG. 5B shows that compound 25 significantly reversed EcoHIV-induced increases in CSF glutamate concentration in the EcoHIV mice.

Discussion

Using the prototype glutamine antagonist DON, it is shown for the first time, at doses less than that used for its anticancer efficacy, that DON can selectively abrogate cognitive deficits, for example, cognitive deficits in the EcoHIV model of neuroAIDs. The presently disclosed subject matter demonstrates the use of glutamine antagonists (or their prodrugs or analogs) for the treatment of cognitive deficits, such as asymptomatic neurocognitive impairment (ANI), mild neurocognitive disorder (MND), and severe HIV-associated dementia (HAD).

Example 2

Exemplary DON Prodrug Reverses Cognition Deficits in the Experimental Autoimmune Encephalomyelitis (EAE) Murine Model of Multiple Sclerosis Methods Background;

It is well known that EAE is an animal model of brain inflammation, and in particular is the most commonly accepted experimental model for the human inflammatory demyelinating disease, multiple sclerosis. As shown in FIG. 6, a previous study demonstrated that DON administered i.p. q.a.d at a dose of 1.6 mg/kg from the time of immunization attenuates EAE (Shijie, et al., 2009), but lower doses were ineffective. No other studies on DON in EAE have been reported.

Prevention Study:

C57BL/6 mice immunized with MOG 35-55 to induce EAE (Rahn, et al., 2012; Hollinger, et al., 2016). Mice administered Vehicle or an exemplary DON prodrug (1 mg/kg equivalent) p.o. q.d. from day of immunization, monitored for body weight and EAE disease score.

Treatment/Cognition Study:

C57BL/6 mice immunized with MOG 35-55 to induce EAE (Rahn, et al., 2012; Hollinger, et al., 2016). Mice administered Vehicle or DON prodrug (1 mg/kq equivalent) p.o. q.a.d. from appearance of disease symptoms (EAE score ≥1). Mice monitored daily for body weight and EAE disease score. Mice tested for cognition in the Barnes maze (4 trials per day over 4 consecutive days) (Rahn, et al., 2012; Hollinger, et al., 2016) >8 wks after treatment began, when disease/disability scores had normalized between groups so that cognitive scores could be compared (P<0.99).

Summary:

Similar to a past report using DON, we found that our exemplary DON prodrug prevented EAE-induced clinical scores. Specifically, as shown in FIG. 7, the DON prodrug completely prevents the development of physical signs of EAE. The magnitude of the therapeutic effect, however, was greater using our prodrug. We extended these findings to show that our exemplary DON prodrug reduced EAE-induced clinical scores using a treatment paradigm in which the drug was not administered until the onset of physical signs of EAE (FIG. 8A and FIG. 8B). We also report for the first time that the exemplary DON prodrug reverses EAE-induced cognitive deficits as measured by performance in the Barnes maze (FIG. 9, FIG. 10A and FIG. 10B). These data suggest that DON prodrugs can be used to treat or prevent cognitive deficits in subjects suffering from multiple sclerosis.

Example 3

DON Attenuates Cognitive Deficits

Methods

Compounds:

Lipopolysaccharide (LPS; 0111:B4, Lot 115M4090V) was obtained from Sigma-Aldrich and dissolved in ice cold filtered phosphate buffered saline (PBS) on the day of administration. Compound 9 was synthesized by our laboratory and dissolved in 3% ethanol in HEPES-buffered saline (50 mM) on the day of administration.

Animals:

Studies were conducted according to protocol #MO16M27 approved by the Animal Care and Use Committee at Johns Hopkins University. Male C57BL/6 mice were obtained from Envigo (Envigo RMS Division, Indianapolis, Ind.) at 9 weeks old and maintained on a 12 hour light-dark cycle with ad libitum access to food and water. Mice were allowed three days to habituate to the facility prior to fear conditioning and testing.

Fear Conditioning:

Fear conditioning and testing were performed in sound-attenuating chambers equipped with a metal grid floor to deliver calibrated inescapable footshocks. Fear conditioning (Day 1) consisted of a 2 minute habituation period followed by three 20 second 80 dB 2 kHz tones co-terminating in 0.4 mA footshocks separated by 1 minute interstimulus intervals. One day later (Day 2), each mouse was randomized into one of four treatment groups (PBS/Vehicle, PBS/9, LPS/Vehicle, LPS/9) and co-administered either LPS (0.3 mg/kg, i.p.) or filtered PBS with either 9 (1.9 mg/kg, i.p.) or Vehicle. Four hours later, each mouse was exposed to a reactivation session in which they were placed back in the fear conditioning context for 15 minutes. One day later (Day 3), each mouse underwent a test for fear memory reconsolidation by being placed again in the fear conditioning context for 10 minutes. For each session, time spent freezing was determined using automated motion detection software (CleverSys) and converted to percentages.

Data Analysis:

Freezing percentages during the reconsolidation test were grouped by treatment into 2 minute bins. Between group differences were determined by repeated measure two-way ANOVA and post hoc Dunnett's test with significance defined as p<0.05.

Results

LPS administration at a dose (0.3 mg/kg, i.p.) known to increase peripheral and brain markers of inflammation impaired the reconsolidation of contextual fear memory. Mice that received LPS/Vehicle exhibited reduced freezing during the reconsolidation test. This effect was attenuated by co-administration of 9 (1.9 mg/kg, i.p.) (effect of time [$F(4,144)=8.49$, $p<0.0001$]).

Conclusion

Similar to its reported effects on conditioned fear acquisition and consolidation (Pugh, et al., 1998; Thomson, et al., 2005), the present study demonstrates that acute peripheral administration of LPS also impairs reconsolidation of fear memory. The cellular mechanisms that subserve reconsolidation have yet to be fully delineated, but early work suggests that this process shares several of the same molecular mediators with initial consolidation and is likely dependent on functional glutamatergic signaling (Li, et al., 2013; McGaugh, 2000; Suzuki, et al., 2004). Peripheral LPS administration induces pro-inflammatory cytokine release in the brain that perturbs glutamatergic signaling through various mechanisms (Potter, et al., 2013; Lee, et al., 2015), ultimately impairing the maintenance of glutamate-dependent memory. Co-administration of 9 with LPS may act via one or both of these mechanisms to attenuate subsequent impairment of memory reconsolidation.

Example 4

Compound 14b Enhanced CSF Delivery of DON in Monkey

Method
  Compound:
  Compound 14b was dissolved in 50 mM HEPES buffered saline containing 5% ethanol and 5% tween on the date of administration.
  Monkey:
  Monkey studies were conducted according to protocol (#PR15M298) approved by the Animal Care and Use Committee at Johns Hopkins University. Two female pigtail monkeys (approximately 3.5 kg, non-drug naive) were adjacently housed in stainless steel cages on a social interaction rack (contains 4 cages, each 32.5" wide×28" deep×32" high) maintaining temperature of 64-84° F., humidity of 30-70% with alternating 14-10 hour light/dark cycle as per the USDA Animal Welfare Act (9 CFR, Parts 1, 2, and 3). Food was provided daily in amounts appropriate for the size and age of the animals and RO purified water provided ad libitum through an in-cage lixit valve. Food enrichment was provided Monday through Friday.
  Treatment:
  Prior to drug administration, macaques were sedated with ketamine given as an intramuscular injection prior to test article administration. Sedation was maintained through blood and cerebrospinal fluid (CSF) sample collections with ketamine at a starting rate of 15 mg/kg with additional doses of 20-30 mg during the first hour. At subsequent time points ketamine was given at 10-15 mg/kg. DON (50 mM HEPES buffered saline) and compound 14b (50 mM HEPES buffered saline containing 5% ethanol and 5% tween) were administered (1.6 and 3.6 mg/kg equivalent dose of DON) to the animals at a dosing volume of 1 mL/kg intravenously. CSF sample (target of 50 µL) was obtained by percutaneous puncture of the cisterna magna at 30 min post dose. Blood samples (1 mL) were collected at 15 min, 30 min, 1 h, 2 h, 4 h, and 6 h post dose by percutaneous puncture of a peripheral vein. Samples were processed for plasma (centrifuged at a temperature of 4° C., at 3,000 g, for 10 minutes). All samples were maintained chilled on ice throughout processing. Samples were collected in microcentrifuge tubes, flash frozen, and placed in a freezer set to maintain −80° C. until LC/MS analysis.
  Data Analysis:
  DON was extracted from samples (50 mg) with 250 µL methanol containing glutamate-$d_5$ (10 µM ISTD) by vortexing in low retention tubes. Samples were centrifuged at 16,000 g for 5 minutes to precipitate proteins. Supernatants (200 µL) were moved to new tubes and dried at 45° C. under vacuum for 1 hour. To each tube, 50 µL of 0.2 M sodium bicarbonate buffer (pH 9.0) and 100 µL of 10 mM dabsyl chloride in acetone was added. After vortexing, samples were incubated at 60° C. for 15 minutes to derivatize. Samples (2 µL) were injected and separated on an Agilent 1290 equipped with an Agilent Eclipse plus C18 RRHD 2.1×100 mm column over a 2.5 minute gradient from 20-95% acetonitrile+0.1% formic acid and quantified on an Agilent 6520 QTOF mass spectrometer. Calibration curves over the range of 0.005-17.1 µg/mL in plasma and CSF for DON were constructed from the peak area ratio of the analyte to the internal standard using linear regression with a weighting factor of 1/(nominal concentration). Correlation coefficient of greater than 0.99 was obtained in all analytical runs. The mean predicted relative standard deviation for back calculated concentrations of the standards and QC's for all analytes were within the range of 85 to 115%, except for the lowest concentration which was within the range of 80 to 120% with an overall accuracy and precision of 6.7% and 6.6% respectively.
  Results
  The pharmacokinetics of DON and compound 14b in monkeys were evaluated. In pigtail macaques, i.v. administration of DON (1.6 mg/kg) and compound 14b (3.6 mg/kg; 1.6 mg/kg DON equivalent) demonstrated significantly different DON plasma profiles (FIG. 12A). DON administration provided high plasma exposures with AUC0-t of 42.7 nmol*h/mL. In contrast, compound 14b administration delivered ~7 fold lower plasma exposure of DON with AUC0-t of 5.71 nmol*h/mL. The opposite observation was seen in the CSF where enhanced DON levels were observed after compound 14b administration. In the CSF at 30 min post dose, DON administration resulted in 0.33 nmol/g DON while compound 14b delivered 1.43 nmol/g DON. When comparing plasma to CSF ratio at 30 min, compound 14b demonstrated unexpected 10-fold enhancement of DON CSF delivery versus DON (FIG. 12B).

Example 5

Compounds 14b and 47 Enhanced CSF Delivery of DON in Swine

Method

Compound:

Compound 47 was dissolved in a sterile saline containing 5% ethanol and 5% Tween 80 on the date of administration.

Swine:

Swine studies were conducted under a protocol approved by the Johns Hopkins Animal Care and Use Committee. Adult, female Göttingen×Yucutan miniature swine (Massachusetts General Hospital, MA) were housed in Johns Hopkins University facilities accredited by the Association for Assessment and Accreditation of Laboratory Animal Care International in compliance with the Animal Welfare Act, Animal Welfare Regulations, and the Public Health Service Policy on the Humane Care and Use of Laboratory Animals. Animals were maintained on a 14-h light and 10-h dark schedule, provided ad libitum water and a commercial miniswine diet (Teklad, Madison, Wis.) with environmental enrichment (fruit/vegetables) twice daily.

DON and Compounds 14b and 47 Treatment:

Animals were individually housed while on study in order to monitor behavior and clinical health following drug administration. Whole blood for drug pharmacokinetic evaluation was collected from a dual lumen central venous catheter (CVC) implanted in the external jugular vein prior to study initiation. Animals were anesthetized with a combination of ketamine hydrochloride (20-30 mg/kg, i.m.) and xylazine (2 mg/kg, i.m.), intubated, and maintained under isoflurane (1-2%) inhalant anesthesia. A temporary peripheral saphenous vein catheter was placed in the hind limb to allow for anatomical separation of drug infusion and whole blood sampling via CVC. DON and compounds 14b and 47 were dissolved in a sterile saline solution containing 5% ethanol and 5% Tween 80 prior to i.v. infusion via saphenous vein catheter over 1 hour (1 ml/min) for a final dose of 1.6 mg/kg or molar equivalent administered at 1 ml/kg (n=1/dose). Blood samples (1 mL) were taken from CVC at predose, 5, 15, 30, 45, and 60 min. Plasma was separated by low speed centrifugation at 3000 g for 10 min at 4° C. CSF was obtained from the cisterna magna using a 3.5 in×22 gauge spinal needle (Becton Dickinson Health Care, Franklin Lakes, N.J., USA) at 60 min post-dose. All samples were flash frozen upon harvest and stored at −80 C until bioanalysis.

Data Analysis:

Quantitation of DON in plasma, CSF, and brain homogenate by LC-MS/MS was performed. Briefly, DON was extracted from plasma, CSF, and brain samples with methanol containing glutamate-$d_5$ (10 μM ISTD) by vortexing followed by centrifugation 16000 g for 5 min. Supernatants were aliquoted and dried at 45° C. for under vacuum for 1 h. Sodium bicarbonate buffer (0.2M, pH 9.0) and dabsyl chloride (10 mM) in acetone were added to each tube, mixed, and incubated for 15 min at 60° C. to derivatize. Samples were then injected and separated on an Agilent 1290 equipped with an Agilent Eclipse plus C18 RRHD 2.1×100 mm column over a 2.5 min gradient from 20 to 95% acetonitrile+0.1% formic acid and quantified on an Agilent 6520 QTOF mass spectrometer. Peak area ratio of the analyte to the internal standard was plotted against a 14 standard curve to yield DON concentrations for each sample.

Result

The pharmacokinetic of DON, compound 14b and compound 47 were evaluated in swine. IV administration of compounds 14b and 47 (1.6 mg/kg DON equivalent dose) resulted in 3-5-fold lower DON plasma exposures relative to an equimolar dose of DON (FIG. 13A). Plasma $AUC_{0-t}$ for DON and compounds 14b and 47 were 29.9, 8.00 and 5.70 nmol·h/mL, respectively. The opposite trend occurred in CSF, where compounds 14b and 47 delivered substantially higher amounts of DON to the CSF (FIG. 13B), resulting in unexpected increased CSF-to-plasma ratios (FIG. 13C).

Example 6

Compound 25 Ameliorates Social Avoidance Behavior Induced by Chronic Social Defeat Stress (CSDS)

Method

Compound:

Compound 25 was synthesized by our laboratory. For all pharmacokinetic and efficacy studies, compound 25 was administered per oral (p.o.) at a dose of 1.82 mg/kg (1 mg/kg DON equivalent) in 50 mM HEPES-buffered saline.

Mice:

Male 7- to 8-week-old C57BL/6J (C57) mice (25-30 g; Jackson Laboratory, Bar Harbor, Me.) and 4- to 6-month-old CD-1 retired breeders (35-45 g; Charles River Laboratories, Wilmington, Mass.) were used for all experiments. Mice were housed on a reversed 12-h light/dark cycle, and maintained in a humidity- and temperature-controlled room with water and food available ad libitum. CD-1 mice were singly housed except during social defeats. C57 mice were group housed before starting CSDS and singly housed after CSDS. Behavioral experiments were conducted during the dark cycle. All studies were conducted with approved protocols from the Johns Hopkins University Institutional Animal Care and Use Committee and were in accordance with the NIH guidelines for the Care and Use of Laboratory Animals.

Treatment and Results:

Mice were exposed to CSDS and subsequently administered compound 25 or vehicle every other day for 12 days (FIG. 14A). To examine the effect of compound 25 treatment on behavioral phenotypes induced by CSDS, we first tested the mice in the three-chambered social approach test, where the social approach of a mouse toward a stranger mouse trapped in a wire cage was measured. Control mice exhibited significant preference for exploring a stranger mouse (stranger 1) relative to an empty cage, as measured by the total amount of time spent in each chamber and time spent sniffing each cage (two-tailed Student's t test, p=0.0025, FIG. 14B; p=0.0007, FIG. 14C). Consistent with previous reports, CSDS resulted in a social avoidance phenotype (Anacker et al, 2016; Hodes et al, 2014; Wook Koo et al, 2016); mice in the CSDS group did not show preference for exploring the stranger mouse relative to the empty cage (two-tailed Student's t test, p=0.1523, FIG. 14B; p=0.1189, FIG. 14C). Chronic treatment of Compound 25 normalized observed social behaviors in mice subjected to CSDS (two-tailed Student's t test, p=0.0036, FIG. 14B; p=0.0035, FIG. 14C), while having no effect on sociability in control mice (two-tailed Student's t test, p=0.0005, FIG. 14B; p=0.0058, FIG. 14C). These results suggest that compound 25 can rescue CSDS-induced sociability deficit.

Example 7

DON Prevented Cognitive Decline in the EcoHIV-Infected Mouse Model of HAND

Method

Figure 15A:
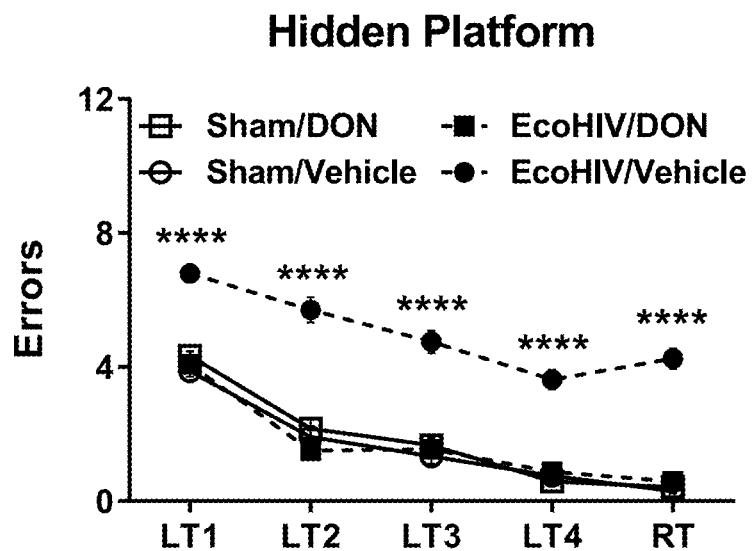
Figure 15B:
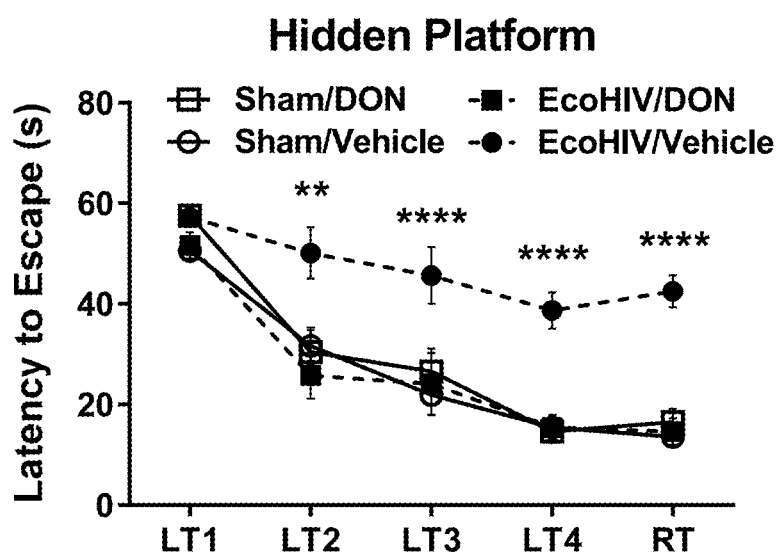
Figure 15C:
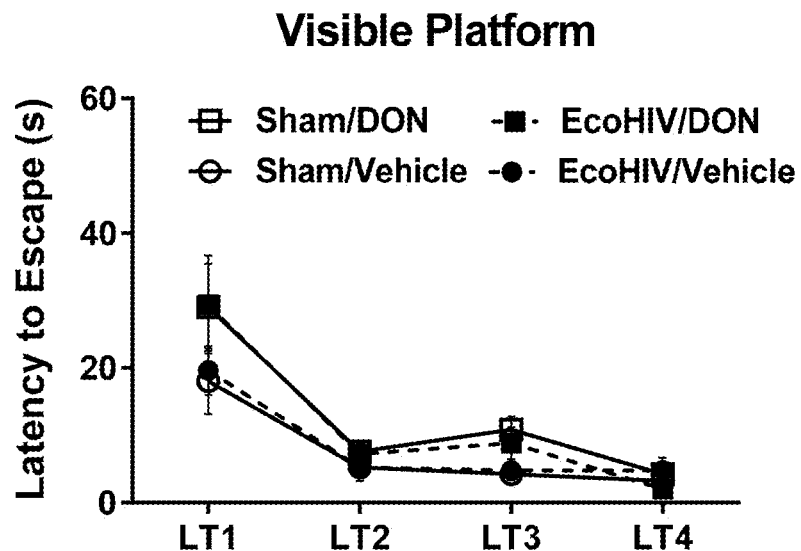
Figure 15D:
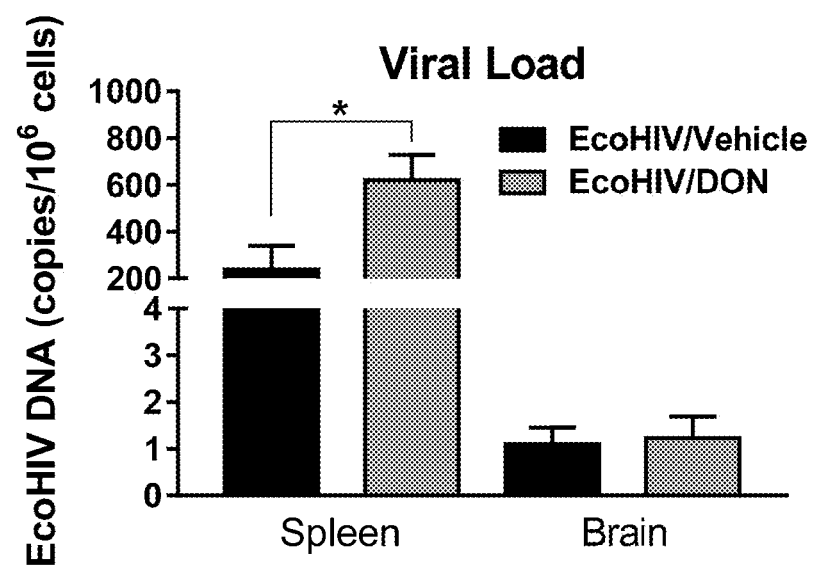

Treatment and Results:

Similar to HAND patients, mice inoculated with EcoHIV exhibited impaired spatial learning and memory as measured by radial arm water maze (RAWM) 30 days post-infection (FIG. 15A). EcoHIV infection resulted in a significant increase in the number of errors (FIG. 15A) and latency to escape (FIG. 15B) onto a hidden platform in the maze. DON treatment (1 mg/kg, i.p., q.o.d.) beginning one day prior to EcoHIV or sham inoculation, and continued throughout the infection period and RAWM testing, fully normalized cognitive performance as measured by both errors (main effect of treatment [F(3,140)=261.8, p<0.0001], trial [F(4,140)=146.2, p<0.0001], interaction [F(12,140)=1.93, p=0.0355]) and latency to escape (main effect of treatment [F(3,140)=37.00, p<0.0001], trial [F(4,140)=56.03, p<0.0001], interaction [F(12,140)=1.832, p=0.0484]). Neither EcoHIV infection nor DON treatment affected latency to escape to a visible platform (FIG. 15C; main effect of trial [F(3,112)=34.44, p<0.0001]) indicating no impairment in visual or motor function. Additionally, no mice exhibited overt signs of toxicity (i.e. diarrhea, weight loss). The EcoHIV-infected mice exhibited measurable viral loads in the spleen and brain (FIG. 15D). DON treatment actually caused an increase in peripheral viral load (t(14)=2.58, p=0.022) likely due to the well described 14-mediated inhibition of T cell activity/proliferation 61, which is known to be required for endogenous suppression of EcoHIV replication. Therefore, despite enabling a modest increase in EcoHIV replication, DON still prevented cognitive decline, suggesting its mechanism of action to be secondary to the infection itself. These findings suggest that glutaminase inhibition through DON delivery to the CNS prior to or during HIV infection may prevent the development of cognitive impairment in HAND patients.

Unexpectedly, we have discovered that DON prevented the spacial memory deficits in an animal model of HAND. We have also shown that DON prodrugs provide enhanced CNS delivery. Therefore, DON prodrugs are useful for the treating of HAND in individuals infected by HIV.

Example 8

Compound 25 Ameliorates Anhedonia-Like Behavior Induced by CSDS

Method
Sucrose Preference Test:
The sucrose preference test was performed according to a previously described protocol (Cao et al, 2013; Roybal et al, 2007). The mice were singly caged before the test. On day 1, their normal water bottles were replaced with two 50 ml tubes (bottle 'A' and bottle 'B') fitted with bottle stoppers containing two-balled sipper tubes. The position of bottles A and B were switched daily to avoid a side bias, and the fluid consumed from each bottle was measured daily. During days 1 and 2, bottles A and B were filled with normal drinking water (W/W). During days 3 and 4, both bottles were filled with a solution of 1.5% sucrose dissolved in drinking water (S/S). On days 5-8, bottle A contained 1.5% sucrose, and bottle B contained drinking water (S/S). Sucrose preference on each day for each mouse was calculated as 100%×(Vol A/(Vol A+Vol B)) and averaged across the days for a given condition (W/W, S/S, or S/W). The average of total fluid consumption was also calculated as (Vol A+Vol B).

Treatment and Results:
Mice subjected to CSDS have repeatedly been shown to exhibit reduced sucrose preference, an effect associated with stress-induced anhedonia (Krishnan et al, 2007). To examine the effect of compound 25 treatment on anhedonia-like behavior, control and CSDS mice were subjected to an 8-day sucrose preference test. Among all groups of mice, there were no differences of fluid consumption between bottles A and B when filled with either normal drinking water (W/W, days 1 and 2) or 1.5% sucrose solution (S/S, days 3 and 4), suggesting that there was no side preference of solution consumption during test days 1-4. On days 5-8, control mice showed significant preference for the sucrose solution when compared with water consumption (two-tailed Student's t test, p<0.01). Three-way repeated measures ANOVA revealed a CSDS×drug treatment interaction on the sucrose preference on days 5-8 (F(1,29)=5.873, p=0.022). In agreement with previous studies (Krishnan et al, 2007), post-hoc tests indicated that mice in the CSDS group exhibited decreased sucrose solution consumption compared with those in controls (p=0.0028, 0.0155, and 0.0132 for days 6-8, respectively), with no differences in total fluid intake, suggesting decreased sucrose preference induced by CSDS. Treatment with compound 25 markedly restored sucrose consumption in the CSDS group (p=0.0039, 0.0003, 0.0016, and 0.0018 for days 5-8, respectively, FIG. 16), whereas no change was observed in controls (p=0.7687, 0.9933, 0.9866, and 0.9871 for days 5-8, respectively), suggesting that compound 25 can rescue the anhedonia-like behavior phenotype induced by CSDS.

Example 9

Compound Synthesis and Characterization

Representative compounds of the disclosure can be prepared as described in PCT/US2016/044767 (WO 2017/023774 A1), which is fully incorporated by reference herein.

Scheme 1.

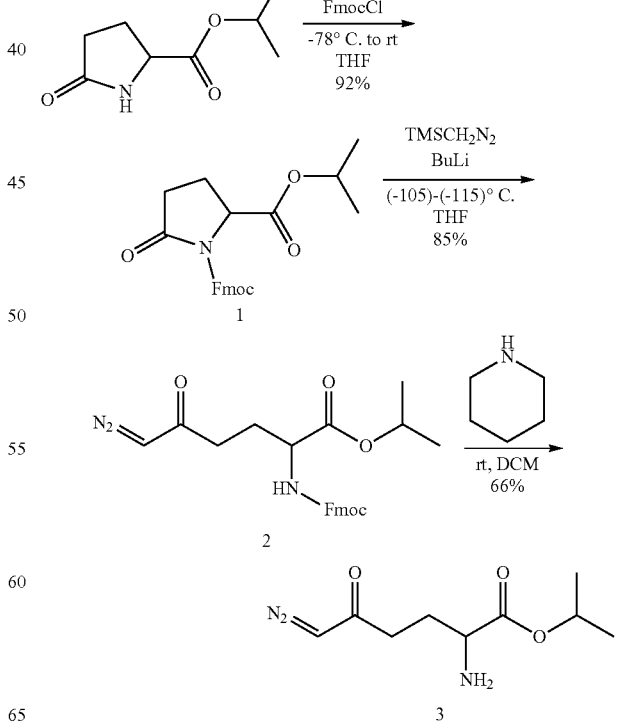

Scheme 2
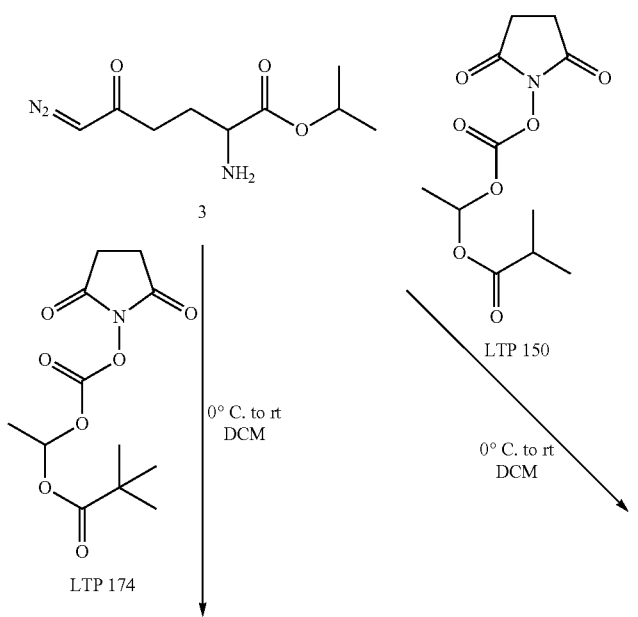
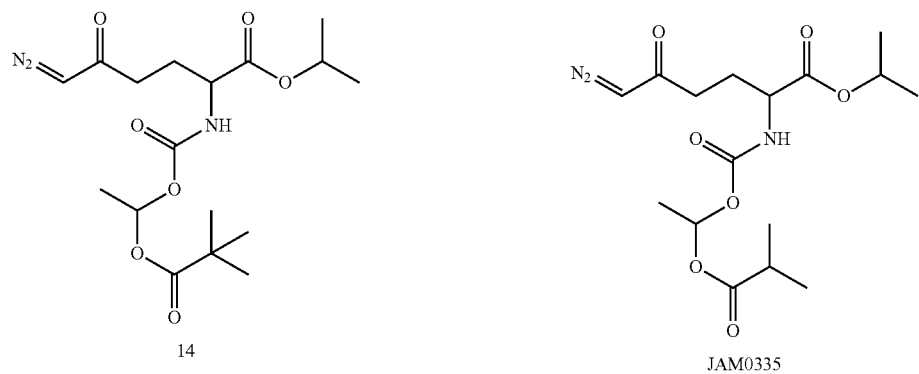
Scheme 3
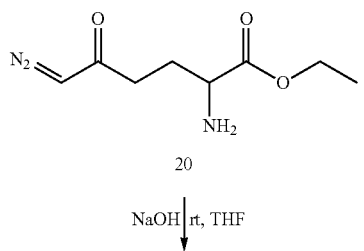
NaOH | rt, THF

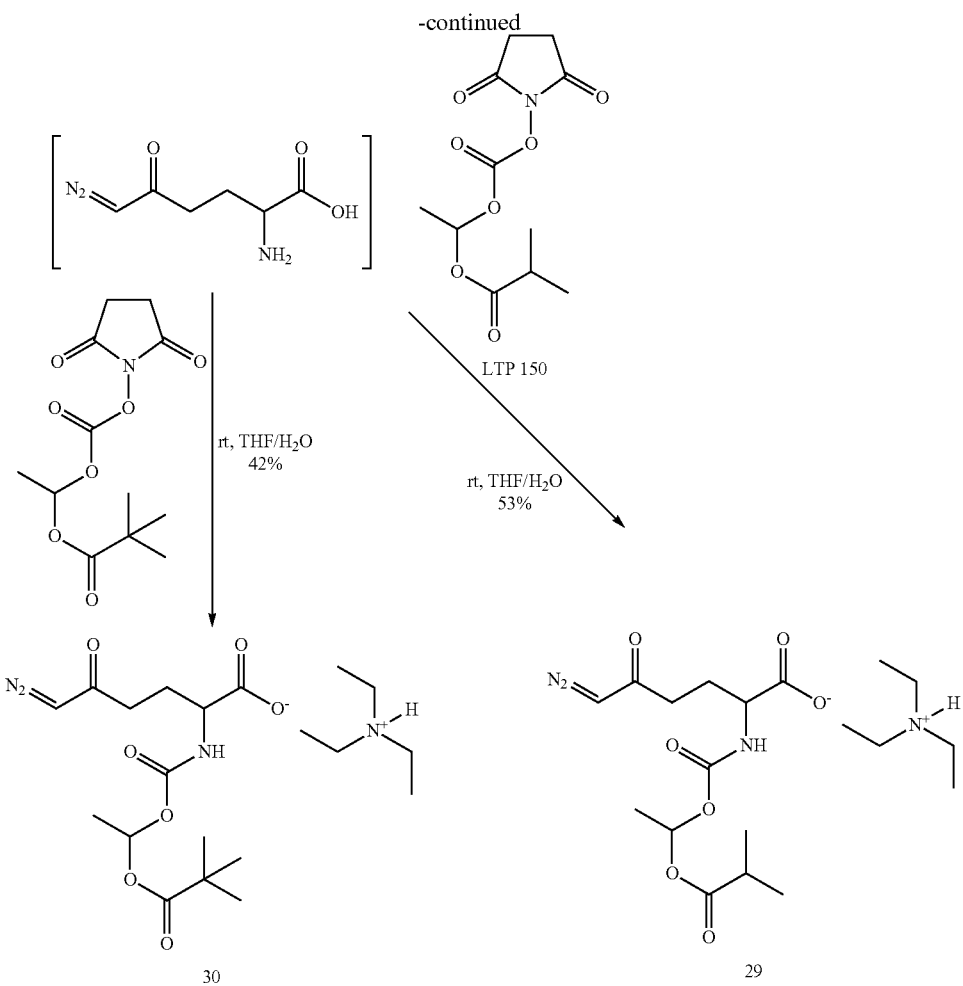

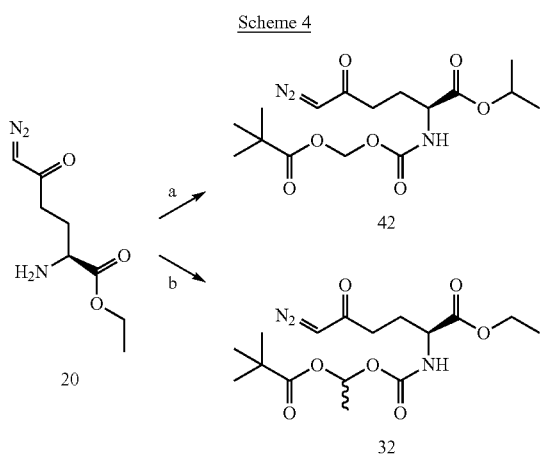

Scheme 4

Reagents and conditions: (a) POM—NHS, DCM, 40% (b) Me—POM—NHS, DCM, 68%.

REFERENCES

Anacker C., et al., Neuroanatomic Differences Associated With Stress Susceptibility and Resilience. Biological psychiatry, 2016. 79(10): p. 840-49.

Antinori, A., et al., Updated research nosology for HIV-associated neurocognitive disorders. Neurology, 2007. 69(18): p. 1789-1799.

Bojabad, A., et al., Significant effects of antiretroviral therapy on global gene expression in brain tissues of patients with HIV-1-associated neurocognitive disorders. PLoS Pathog., 2011. 7(9): p. e1002213.

Cao, X, et al., Astrocyte-derived ATP modulates depressive-like behaviors. Nature medicine, (2013) 19(6): p. 773-777. Chang, L., et al., Persistent brain abnormalities in antiretroviral-naive HIV patients 3 months after HAART. Antivir. Ther., 2003. 8(1): p. 17-26.

Dickens, A. M., et al., CSF Metabolomics Implicate Bioenergetic Adaptation as a Neural Mechanism Regulating Shifts in the Cognitive States of HIV-Infected Subjects. AIDS (Article in press), 2015.

Ellis, R I, D. Langford, and E. Masliah, HIV and antiretroviral therapy in the brain: neuronal injury and repair. Nat. Rev. Neurosci., 2007. 8(1): p. 33-44.

Everall, I., et al., Cliniconeuropathologic correlates of human immunodeficiency virus in the era of antiretroviral therapy. J. Neurovirol., 2009. 15(5-6): p. 360-370.

Gelman, B. B., et al., The National NeuroAIDS Tissue Consortium brain gene array: two types of HIV-associated neurocognitive impairment. PLoS One, 2012. 7(9): p. e46178.

Harezlak, J., et al., Persistence of HIV-associated cognitive impairment, inflammation, and neuronal injury in era of highly active antiretroviral treatment. AIDS, 2011. 25(5): p. 625-633.

Heaton, R. K., et al., HIV-associated neurocognitive disorders before and during the era of combination antiretroviral therapy: differences in rates, nature, and predictors. J. Neurovirol., 2011. 17(1): p. 3-16.

Heaton, R. K., et al., HIV-associated neurocognitive disorders persist in the era of potent antiretroviral therapy: CHARTER Study. Neurology, 2008. 75(23): p. 2087-96.

Hollinger, K. R., et al., Dose-dependent inhibition of GCPII to prevent and treat cognitive impairment in the EAE model of multiple sclerosis. Brain Res., 1635:105-12, 2016.

Hodes G E, et al., Individual differences in the peripheral immune system promote resilience versus susceptibility to social stress. Proceedings of the National Academy of Sciences of the United States of America, 2014. 111(45): p. 16136-41.

Kaul, M., et al., HIV-1 infection and AIDS: consequences for the central nervous system. Cell Death Differ., 2005. 12 Suppl 1: p. 878-892.

Krishnan V., et al., Molecular adaptations underlying susceptibility and resistance to social defeat in brain reward regions. Cell, 2007 131(2): p 391-404.

Lee, C. F.; Lo, Y. C.; Cheng, C. H.; Furtmuller, G. J.; Oh, B.; Andrade-Oliveira, V.; Thomas, A. G.; Bowman, C. E.; Slusher, B. S.; Wolfgang, M. J.; Brandacher, G.; Powell, J. D. Preventing Allograft Rejection by Targeting Immune Metabolism. *Cell Rep* 2015, 13, 760-70.

Lentz, M. R., et al., Changes in MRS neuronal markers and T cell phenotypes observed during early HIV infection. Neurology, 2009. 72(17): p. 1465-1472.

Li, Y.; Meloni, E. G.; Carlezon, W. A., Jr.; Milad, M. R.; Pitman, R. K.; Nader, K.; Bolshakov, V. Y. Learning and reconsolidation implicate different synaptic mechanisms. *Proc Natl Acad Sci USA* 2013, 110, 4798-803.

McArthur, J. C., et al., Human immunodeficiency virus-associated neurocognitive disorders: Mind the gap. Ann. Neurol., 2010. 67(6): p. 699-714.

McGaugh, J. L. Memory—a century of consolidation. *Science* 2000, 287, 248-51.

Potter, M. C.; Figuera-Losada, M.; Rojas, C.; Slusher, B. S. Targeting the glutamatergic system for the treatment of HIV-associated neurocognitive disorders. *J Neuroimmune Pharmacol* 2013, 8, 594-607.

Pugh, C. R.; Kumagawa, K.; Fleshner, M.; Watkins, L. R.; Maier, S. F.; Rudy, J. W. Selective effects of peripheral lipopolysaccharide administration on contextual and auditory-cue fear conditioning. *Brain Behav Immun* 1998, 12, 212-29.

Rahn, K. A., et al., Inhibition of glutamate carboxypeptidase II (GCPII) activity as a treatment for cognitive impairment in multiple sclerosis. PNAS, 109(49):20101-6, 2012.

Robertson, K. R., et al., The prevalence and incidence of neurocognitive impairment in the HAART era. AIDS, 2007. 21(14): p. 1915-1921.

Roybal K. et al., Mania-like behavior induced by disruption of CLOCK. Proceedings of the National Academy of Sciences of the United States of America, 2007. 104(15): p. 6406-6411.

Sailasuta, N., et al., Change in brain magnetic resonance spectroscopy after treatment during acute HIV infection. PLoS One, 2012. 7(11): p. e49272.

Shiji, J. et al., Blockade of glutamate release from microglia attenuates experimental autoimmune encephalomyelitis in mice. Tohoku J. Exp. Med., 217:87-91, 2009.

Simioni, S., et al., Cognitive dysfunction in HIV patients despite long-standing suppression of viremia. AIDS, 2010. 24(9): p. 1243-1250.

Suzuki, A.; Josselyn, S. A.; Frankland, P. W.; Masushige, S.; Silva, A. J.; Kida, S. Memory reconsolidation and extinction have distinct temporal and biochemical signatures. *J Neurosci* 2004, 24, 4787-95.

Thomson, L. M.; Sutherland, R. J. Systemic administration of lipopolysaccharide and interleukin-1beta have different effects on memory consolidation. *Brain Res Bull* 2005, 67, 24-9.

Wook Koo J., et al., Essential Role of Mesolimbic Brain-Derived Neurotrophic Factor in Chronic Social Stress-Induced Depressive Behaviors. Biological psychiatry, 2016. 80(6): p. 469-478.

Zink, M. C., Translational research models and novel adjunctive therapies for neuroAIDS. J Neuroimmune Pharmacol, 2007. 2(1): p. 14-9.

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a subject having a cognitive deficit, the method comprising administering to the subject a compound having formula (II):

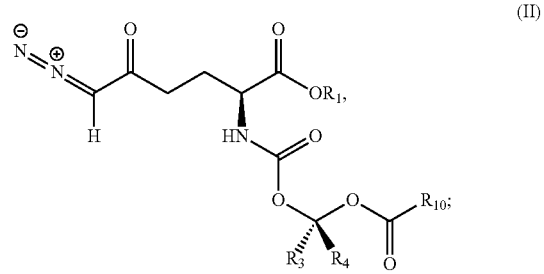

or a pharmaceutically acceptable salt thereof;

wherein:

$R_1$ is selected from the group consisting of H and $C_{1-6}$ alkyl;

R$_3$ and R$_4$ are independently selected from the group consisting of H, C$_1$-C$_6$ alkyl, substituted C$_1$-C$_6$ alkyl, aryl, and substituted aryl; and R$_{10}$ is C$_{1-6}$ alkyl, in an amount effective to treat the cognitive deficit.

2. The method of claim 1, wherein R$_1$ is selected from the group consisting of methyl, ethyl, and isopropyl.

3. The method of claim 1, wherein R$_3$ is H and R$_4$ is selected from the group consisting of methyl and phenyl.

4. The method of claim 1, wherein R$_{10}$ is selected from the group consisting of isopropyl and tert-butyl.

5. The method of claim 1, wherein the compound having formula (II) is selected from the group consisting of:

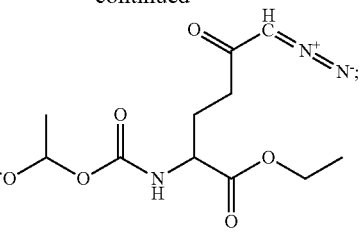
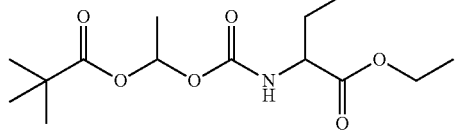
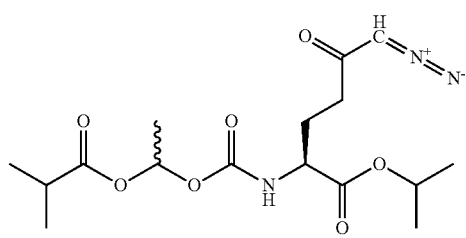
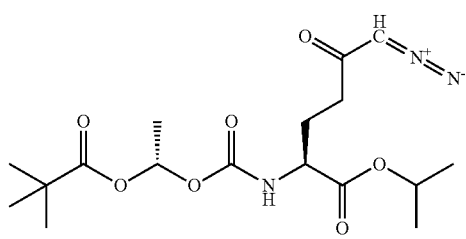
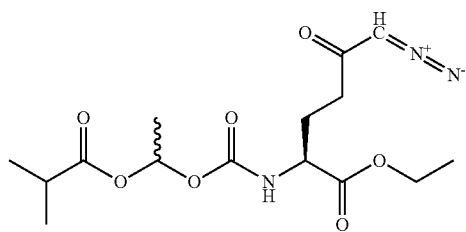
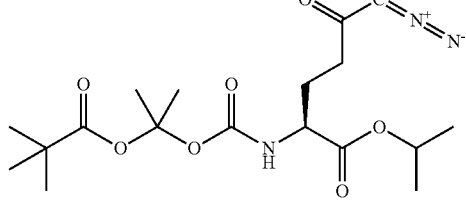
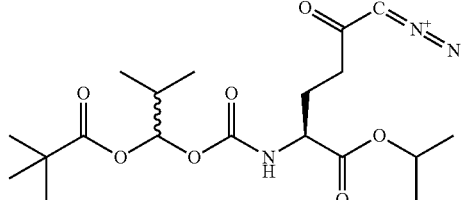
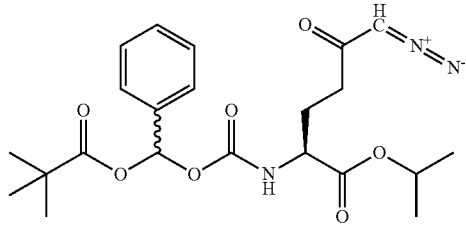

6. The method of claim 5, wherein the compound having formula (I) is selected from the group consisting of:

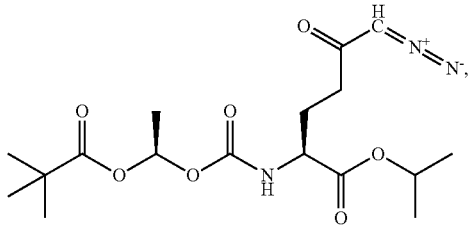

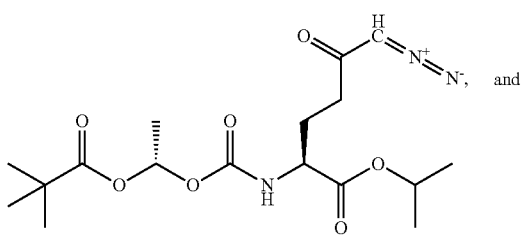 and

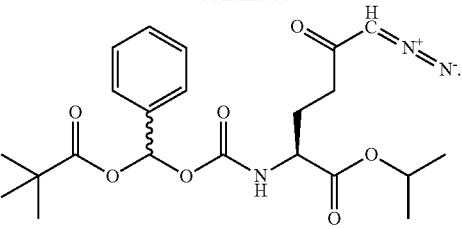

7. The method of claim 1, wherein the cognitive deficit is characterized by impairment of the mental processes of perception, learning, memory, judgment, and/or reasoning.

8. The method of claim 1, wherein the cognitive deficit is due to a viral infection.

9. The method of claim 8, wherein the cognitive deficit is due to the human immunodeficiency virus (HIV).

10. The method of claim 9, wherein the virus is latent.

11. The method of claim 1, wherein the cognitive deficit is selected from the group consisting of asymptomatic neurocognitive impairment (ANI) and mild neurocognitive disorder (MND).

12. The method of claim 1, wherein the cognitive deficit is associated with a neurodegenerative disorder.

13. The method of claim 1, wherein the cognitive deficit is associated with multiple sclerosis.

* * * * *